(12) United States Patent
Tang et al.

(10) Patent No.: US 9,109,155 B2
(45) Date of Patent: Aug. 18, 2015

(54) HETEROCYCLE-FUNCTIONALIZED LUMINOGENS EXHIBITING AGGREGATION-INDUCED EMISSION

(71) Applicants: THE HONG KONG UNIVERSITY OF SCIENCE AND TECHNOLOGY, Kowloon, Hong Kong (CN); National University of Singapore, Singapore (SG)

(72) Inventors: Benzhong Tang, Hong Kong (CN); Wing Yip Lam, Hong Kong (CN); Na Zhao, Hong Kong (CN); Min Li, Hong Kong (CN); Bin Liu, Singapore (SG); Haibin Shi, Singapore (SG); Dan Ding, Singapore (SG)

(73) Assignees: The Hong Kong University of Science and Technology, Kowloon, Hong Kong (CN); National University of Singapore, Singapore (SG)

( * ) Notice: Subject to any disclaimer, the term of this patent is extended or adjusted under 35 U.S.C. 154(b) by 82 days.

(21) Appl. No.: 13/902,120

(22) Filed: May 24, 2013

(65) Prior Publication Data

US 2014/0348753 A1     Nov. 27, 2014

(51) Int. Cl.
| | |
|---|---|
| *A61B 5/00* | (2006.01) |
| *A61B 8/00* | (2006.01) |
| *A61B 10/00* | (2006.01) |
| *C09K 11/06* | (2006.01) |
| *C12Q 1/37* | (2006.01) |
| *A61K 9/00* | (2006.01) |

(52) U.S. Cl.
CPC . *C09K 11/06* (2013.01); *C12Q 1/37* (2013.01); *A61K 9/0019* (2013.01); *G01N 2333/96469* (2013.01)

(58) Field of Classification Search
USPC .......................................................... 424/9.6
See application file for complete search history.

(56) References Cited

FOREIGN PATENT DOCUMENTS

WO   WO 2009091334 A1 *  7/2009 .............. C08F 10/00

OTHER PUBLICATIONS

Zhao, Na, et al. "Benzothiazolium-functionalized tetraphenylethene: an AIE luminogen with tunable solid-state emission", Chem. Commun., vol. 48, pp. 8637-8639, (2012).

* cited by examiner

*Primary Examiner* — Michael G Hartley
*Assistant Examiner* — Melissa Perreira
(74) *Attorney, Agent, or Firm* — Nath, Goldberg & Meyer; Joshua B. Goldberg

(57) ABSTRACT

The development of a series of fluorescent materials including heterocycle-functionalized luminogens with aggregation-induced/enhanced emission (AIE/AEE), long wavelength emission, and high solid state fluorescence quantum efficiency is contemplated. The described fluorescent materials are promising candidates in selective luminescence-based chemosensor for $Hg^{2+}$ or ATP, fluorescent staining for mitochondria in living cells with high photostability, stimuli-responsive luminescent materials, and materials for optical waveguides. In addition, these heterocycle-functionalized luminogens are particularly useful as fluorescent labels for biopolymers such as peptides, antibodies, or nucleic acids, making them useful as AIE-active biocompatible probes for clinical cancer imaging and diagnostics.

22 Claims, 41 Drawing Sheets

HETEROCYCLE-FUNCTIONALIZED LUMINOGENS EXHIBITING AGGREGATION-INDUCED EMISSION

RELATED INVENTOR DISCLOSURES

The present patent application was previously disclosed in "Benzothiazolium-functionalized tetraphenylethene: an AIE luminogen with tunable solid-state emission," CHEM. COMMUN., 2012, 48, 8637-39 (2012), which was published on Jul. 11, 2012. This disclosure was made by the inventors hereof and is incorporated by reference herein in its entirety.

TECHNICAL FIELD

The presently described subject matter relates to heterocycle-functionalized luminogens exhibiting aggregation-induced/enhanced emission (AIE/AEE) and long wavelength emission.

BACKGROUND

Recently, the development of new organic luminescent materials in the solid or aggregate state has attracted more attention due to their wide applications in the fields of electronics (*Adv. Mater.*, 2011, 23, 926-952; *Chem. Sci.*, 2011, 2, 2402; *Chem. Rev.* 2007, 107, 1011), optics (*Adv. Mater.*, 2012, 24, 1703-1708), storage mediums (*Adv. Mater.*, 2012, 24, 1255-1261), and biological sciences (*Chem. Sci.*, 2012, 3, 984).

However, aggregation-caused quenching (ACQ) is a common problem for traditional luminescent dyes when their molecules are aggregated due to energy transfer and the formation of excimers and exciplexes. To mitigate the ACQ effect, various chemical (*Chem. Commun.*, 2008, 1501. *Chem. Commun.*, 2008, 217), physical, and engineering (*Langmuir,* 2006, 22, 4799. Macromolecules 2003, 36, 5285) approaches and processes have been developed. These attempts, however, have only resulted in limited success. The difficulty lies in the fact that aggregate formation is an intrinsic process when luminogenic molecules are located in close vicinity in the condensed phase. Accordingly, there is a great need in the art for a system where light emission is enhanced, rather than quenched, by aggregation.

In 2001, the present inventors developed such a system, in which luminogen aggregation played a constructive, instead of a destructive, role in the light emitting process. The inventors also observed a novel phenomenon and coined the term "aggregation-induced emission" (AIE) since the non-luminescent molecules were induced to emit by aggregate formation. For example, a series of propeller-like, non-emissive molecules, such as silole and tetraphenylethene (TPE), were induced to emit intensely by aggregate formation (*Chem. Commun.* 2001, 1740; *J. Mater. Chem.* 2001, 11, 2974; *Chem. Commun.* 2009, 4332; *Appl. Phys. Lett.* 2007, 91, 011111.). After this discovery, the present inventors discovered a large number of molecules bearing this novel property. In addition, through a series of designed experiments, and theoretical calculations, the present inventors identified restriction of intramolecular rotation (IMR) as the main cause for the AIE effect (*J. Phys. Chem. B* 2005, 109, 10061; *J. Am. Chem. Soc.* 2005, 127, 6335).

Since then, various kinds of AIE dye have been widely developed and applied in many fields: OLEDs (*J. Mater. Chem.*, 2011, 21, 7210-7216; *J. Mater. Chem.*, 2012, 22, 11018-11021), bio-probes (*J. Am. Chem. Soc.*, 2012, 134, 9569-9572), chemosensors (*J. Am. Chem. Soc.*, 2010, 132, 13951-13953; *J. Am. Chem. Soc.*, 2011, 133, 18775-18784), and cell imaging (*Adv. Mater.*, 2011, 23, 3298-3202).

However, most AIE dyes prepared so far emit blue or green light determined by their nature of structure (*Chem. Commun.*, 2012, 48, 416; *Chem. Commun.*, 2012, 48, 7880; *Chem. Sci.*, 2012; *J. Mater. Chem.*, 2012, 22, 12001), which limits the application of AIE dye, especially in the field of bioscience. The development of a new AIE dye emitting at a long wavelength is especially needed because it may tolerate little interference between optical self-absorption and autofluorescence from the background (*Chem. Commun.*, 2012, 48, 6073-6084). As is known in the art, to achieve long wavelength emission, the dye molecules are generally constructed from merged planar rings with extended conjugation or that possess strong dipoles coming from electron-donating and accepting groups (ICT process) (*Org. Lett.*, 2008, 10, 4175-4178). However, extending conjugation may be difficult from a synthesis standpoint. Moreover, the emission stemming from the ICT process is always weaker for traditional luminescent dyes in aqueous media due to the effect of polarity for ICT emission (*Chem. Rev.*, 2003, 103, 3899-4032; *J. Phys. Chem. C*, 2009, 113, 15845-15853). This is unfavorable in the bio-environment.

Accordingly, there is a great need for the development of AIE luminogens that can emit long wavelength fluorescence.

SUMMARY

The present subject matter generally relates to cationic light-emitting materials comprising heterocycle-functionalized luminogens prepared via attachment of the heterocycle unit to the AIE unit through vinyl functionality. These cationic light-emitting materials exhibit long wavelength emission and aggregation-induced emission.

Specifically, the present subject matter is directed to a cationic fluorescent luminogen exhibiting aggregation-induced/enhanced emission (AIE/AEE) comprising one or more heterocycle units; wherein the luminogen comprises a chemical structure selected from the group consisting of:

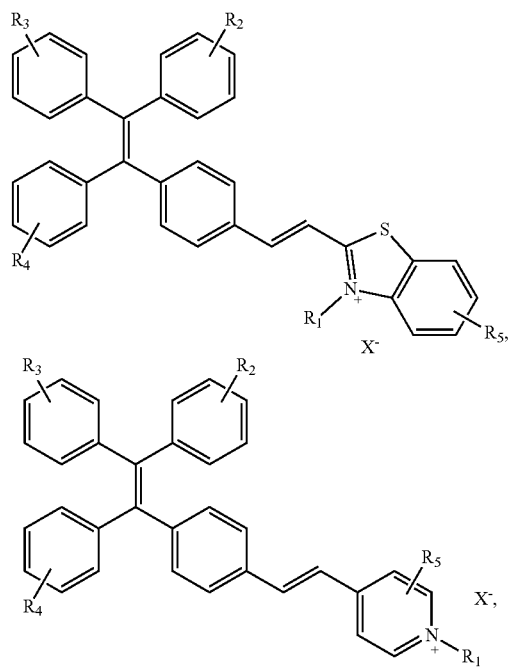

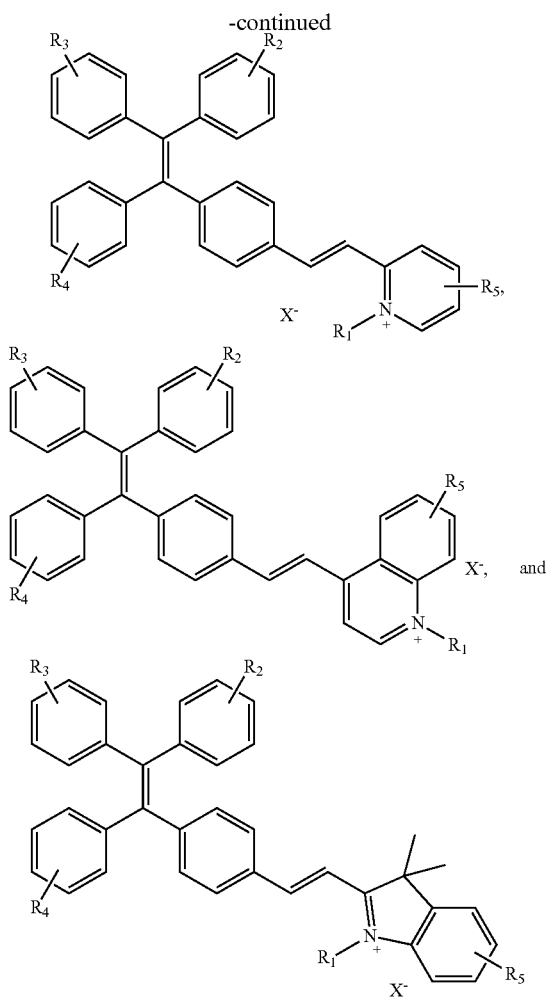

-continued wherein each $R_1$, $R_2$, $R_3$, $R_4$, and $R_5$ is independently selected from the group consisting of H, alkyl, unsaturated alkyl, heteroalkyl, cycloalkyl, heterocycloalkyl, aryl, heteroaryl, $C_nH_{2n+1}$, $C_{10}H_7$, $C_{12}H_9$, $OC_6H_5$, $OC_{10}H_7$, $OC_{12}H_9$, $C_nH_{2n}COOH$, $C_nH_{2n}OH$, $C_nH_{2n}CHO$, $C_nH_{2n}COOC_4O_2N$, $C_nH_{2n}NCS$, $C_nH_{2n}N_3$, $C_nH_{2n}NH_2$, $C_nH_{2n}SH$, $C_nH_{2n}Cl$, $C_nH_{2n}Br$, and $C_nH_{2n}I$; n=0 to 20; and X is a monovalent counterion.

In one embodiment, the luminogen has a long wave fluorescence emission. In another embodiment, X is a monovalent counterion selected from the group consisting of I, Cl, Br, $PF_6$, $ClO_4$, $BF_4$, $BPh_4$, and $CH_3PhSO_3$. In another embodiment, the luminescent materials with AIE/AEE characteristics are dispersed in an aqueous solution. The present subject matter also relates to changing the behavior of luminogen from aggregation-caused quenching (ACQ) to aggregation-induced emission (AIE) through changing the counterions.

In addition, the present subject matter relates to using the luminogen as fluorescent dye to label mitochondria in living cells. In a similar embodiment, the luminogen is used as a "turn-on" fluorescent sensor for $Hg^{2+}$ and/or ATP. The luminogen can also be used as a fluorescent label for biomolecules including peptides, antibodies, and nucleic acids. In addition, the luminogen can be used as an optical waveguide material and mechanochromic fluorescent material.

In another embodiment, the luminogen is used as a probe for caspase activity. In one instance, the luminogen is used as a specific probe for caspase-3 and/or caspase-7 activity. In another instance, the luminogen is used as a probe for apoptosis imaging in live cells. In a related embodiment, the luminogen is used for in vitro and in vivo screening of drugs that can induce cell apoptosis.

In a different embodiment, the present subject matter relates to a method of detecting caspase activity comprising contacting a solution containing cells with caspase enzymes with the luminogen and detecting fluorescence. In one instance the caspase activity is caspase-3 and caspase-7 activity and the caspase enzymes are caspase-3 and caspase-7 enzymes. In another instance, the luminogen is specifically cleaved by the caspase enzymes, including the caspase-3 and caspase-7 enzymes.

In another embodiment, the present subject matter is related to labeling mitochondria in cells comprising contacting one or more live cells with the luminogen. In a related embodiment, the present subject matter is directed to detecting $Hg^{2+}$ comprising contacting a solution comprising $Hg^{2+}$ with the luminogen. Likewise, the present subject matter is also related to a method of detecting ATP comprising contacting a solution comprising ATP with the luminogen.

In addition, the present subject matter is also related to in vivo monitoring of cell apoptosis comprising injecting a subject with the luminogen and detecting fluorescence. Finally, the present subject matter is related to in vitro monitoring of cell apoptosis comprising injecting a sample containing caspase enzymes with the luminogen and detecting fluorescence.

BRIEF DESCRIPTION OF THE DRAWINGS

Various embodiments will be described in detail with reference to the accompanying drawings.

FIG. 18 also shows the photluminescence responses of the TPEBe-I (20 μM) to various metal ions in the aqueous buffer. Black bars represent the addition of different metal ion (2 mM) to solution of the TPEBe-I. Red bars represent the subsequent addition of 2 mM Hg$^{2+}$ to the solution. λ$_{ex}$=480 nm. λ$_{em}$=640 nm.

FIGS. 46a-46c show normal MCF-7 cells treated with Ac-DEVD-PyTPE (5 μM, 1% DMSO) for 2 h.

FIGS. 46d-46f show apoptotic MCF-7 cells treated with Ac-DEVD-PyTPE (5 μM, 1% DMSO) and caspase-3 antibody. STS (3 μM) was used to induce cell apoptosis. Red=probe fluorescence; Green=immunofluorescence signal generated from anti-caspase-3 primary antibody and a FITC labeled secondary antibody.

FIG. 46g-46i show apoptotic MCF-7 cells treated with Ac-DEVD-PyTPE (5 μM, 1% DMSO) and Annexin V-Alexa Fluor. Green=fluorescence signal from Annexin V-Alexa Fluor.

FIG. Ma shows the changes of UV-Vis spectra of TPEBe-I in the aqueous solution with 1% DMSO in the presence of different concentrations of ATP (0-600 μM).

FIG. 51b shows a plot of (A–$A_0$)/$A_0$ value versus concentration of ATP in the aqueous solution with 1% DMSO. $A_0$=absorbance at 420 nm in absence of ATP.

FIG. 52a shows the changes of photoluminescence spectra of TPEBe-I in the aqueous solution with 1% DMSO in the presence of different concentrations of ATP (0-600 μM).

FIG. 52b shows a plot of (I–$I_0$)/$I_0$ value versus concentration of ATP in the aqueous solution with 1% DMSO. $I_0$=PL intensity at 620 nm in absence of ATP. Inset in B: plot of (I–$I_0$)/$I_0$ value versus concentration of ATP from 0 to 20 μM.

FIG. 53a shows photoluminescence responses of the TPEBe-I (20 μM) to various nucleotide in the aqueous solution with 1% DMSO.

FIG. 53b shows a plot of (I–$I_0$)/$I_0$ value versus concentration of various nucleotides in the aqueous solution with 1% DMSO. $I_0$=photoluminescence intensity at 620 nm in absence of nucleotide. Inset: Photographs of TPBBe-I in aqueous solution with 1% DMSO with various nucleotides (600 μM) taken under 365 nm UV illumination.

FIG. Ma shows a bright field image of TPEBe-I (20 μM) in aqueous solution with 1% DMSO in the absence of ATP; the scale bar represents 100 μm.

FIG. 54b shows a fluorescent image of TPEBe-I (20 μM) in aqueous solution with 1% DMSO in the absence of ATP; the scale bar represents 100 μm.

FIG. 54c shows a bright field image of TPEBe-I (20 μM) after addition of ATP (600 μM); the scale bar represents 100 μm.

FIG. 54d shows a fluorescent image of TPEBe-I (20 μM) after addition of ATP (600 μM); the scale bar represents 100 μm.

Figure 55:
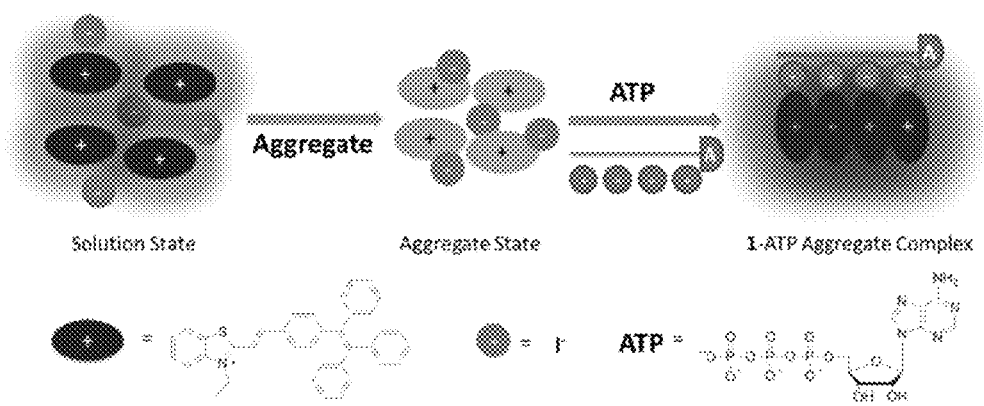

FIG. 55 shows a schematic illustration of the mechanism for detecting ATP.

DETAILED DESCRIPTION

Definitions

All technical and scientific terms used herein have the same meanings as commonly understood by someone ordinarily skilled in the art to which the present subject matter belongs.

The following definitions are provided for clarity.

The phrase "π-conjugated fluorophore" as used herein refers to any fluorophore covalently bonded with alternating single and double bonds in an organic compound.

The term "$\lambda_{ex}$" as used herein refers to excitation wavelength.

The phrase "aggregation caused quenching" or "ACQ" as used herein refers to the phenomenon wherein the aggregation of π-conjugated fluorophores significantly decreases the fluorescence intensity of the fluorophores. The aggregate formation is said to "quench" light emission of the fluorophores.

The phrase "aggregation-induced/enhanced emission" or "AIE/AEE" as used herein refers to the phenomenon manifested by compounds exhibiting significant enhancement of light-emission upon aggregation in the amorphous or crystalline (solid) states whereas they exhibit weak or almost no emission in dilute solutions.

The term "alkyl" as used herein refers to a branched or unbranched hydrocarbon chain comprising a designated number of carbon atoms. For example, a $C_1$-$C_6$ straight or branched alkyl hydrocarbon chain contains 1 to 6 carbon atoms, and includes but is not limited to methyl, ethyl, propyl, iso-propyl, butyl, iso-butyl, tert-butyl, n-pentyl, n-hexyl, and the like. In one embodiment, the "alkyl" chain may be unsubstituted or is substituted by one or more substituents. It is also contemplated as with the scope of the present subject matter that "alkyl" may also refer to a hydrocarbon chain wherein any of the carbon atoms of the alkyl are optionally replaced with O, NH, S, or $SO_2$. For example, carbon 2 of n-pentyl can be replaced with O to form propyloxymethyl.

The term "alkoxy group" refers to an alkyl group singularly bonded to an oxygen atom. The range of alkoxy groups is great, the simplest being methoxy ($CH_3O$—).

The term "aryl" refers to an aromatic carbocyclic group having a single ring, for example a phenyl ring; multiple rings, for example biphenyl; or multiple condensed rings in which at least one ring is aromatic, for example naphthyl, 1,2,3,4-tetrahydronaphthyl, anthryl, or phenanthryl, which can be unsubstituted or substituted with one or more other substituents.

The term "biomacromolecule" as used herein refers to a very large molecule, such as a protein, nucleic acid, or polysaccharide of biological origin.

The term "cycloalkyl" as used herein refers to an organic cyclic substituent comprising a designated number of carbon atoms. For example, a $C_3$-$C_8$ cycloalkyl contains three to eight carbon atoms forming a three, four, five, six, seven, or eight-membered ring, including, for example, a cyclopropyl, cyclobutyl, cyclopentyl, cyclohexyl, cycloheptyl, or cyclooctyl ring, and the like. In one embodiment, the "cycloalkyl" may be unsubstituted or is substituted by one or more substituents.

The term "DEVD" as used herein refers to the Asp-Glu-Val-Asp peptide sequence which can be selectively and specifically cleaved by caspase-3/caspase-7.

The term "DEVD-AFC" as used herein refers to a (7-amino-4-trifluoromethylcoumarin)-derived caspase substrate, which is widely used for the fluorimetric detection of various caspase activities.

The term "DIEA" as used herein refers to N,N-Diisopropylethylamine, or Hünig's base. DIPEA, or DIEA, is an organic compound and an amine. It is used in organic chemistry as a base.

The term "DMF" as used herein refers to dimethylformamide, which is an organic compound with the formula $(CH_3)_2NC(O)H$. It is a common solvent for chemical reactions.

The term "EDTA" as used herein refers to ethylenediaminetetraacetic acid. It is a polyamino carboxylic acid and a colorless, water-soluble solid.

The phrase "emission intensity" as used herein refers to the magnitude of fluorescence/phosphorescence normally obtained from a fluorescence spectrometer or a fluorescence microscopy measurement.

The term "fluorophore" as used herein refers to a fluorescent chemical compound that can re-emit light upon light excitation. Fluorophores typically contain several combined aromatic groups, or plane or cyclic molecules with several π bonds. Fluorophores can be used as tracers in fluids, dyes for staining certain structures, substrates of enzymes, or probes or indicators. Fluorophores absorb light energy of a specific wavelength and re-emit light at a longer wavelength. The absorbed wavelengths, energy transfer efficiency, and time before emission depend on both the fluorophore structure and its chemical environment, as the molecule in its excited state interacts with surrounding molecules.

The phrase "fluorescence resonance energy transfer" or "FRET" as used herein refers to a mechanism describing energy transfer between two chromophores. A donor chromophore, initially in its electronic excited state, may transfer energy to an acceptor chromophore through nonradiative dipole-dipole coupling. The efficiency of this energy transfer is inversely proportional to the sixth power of the distance between donor and acceptor making FRET extremely sensitive to small distances.

The term "Fmoc" as used herein refers to a 9-Fluorenylmethyloxycarbonyl group, which is a protective group for amines. It can be removed by a base, such as piperidine.

The term "HBTU" as used herein refers to O-Benzotriazole-N,N,N',N'-tetramethyl-uronium-hexafluoro-phosphate, which is commonly used for coupling reaction between acids and amines.

The term "heteroaryl" as used herein refers to a heterocycle in which at least one ring is aromatic. A heterocycle is a saturated, unsaturated, or aromatic carbocyclic group having a single ring, multiple rings, or multiple condensed rings, and having at least one hetero atom such as nitrogen, oxygen, or sulfur within at least one of the rings. A heteroaryl can also encompass a heteroalkyl or heterocycloakyl. In one embodiment, the "heteroaryl" may be unsubstituted or is substituted by one or more substituents.

The term "HOBt" as used herein refers to hydroxybenzotriazole, which is an organic compound that is a derivative of benzotriazole. It is mainly used to suppress racemization and improve the efficiency of peptide synthesis.

The term "luminogen" as used herein refers to a chemical compound that manifests luminescence.

The term "nanoparticle" as used herein refers to any microscopic particle or particle population having a mean diameter of about 100 or less nanometers (nm); less than about 90 nm; less than about 80 nm; less than about 70 nm; less than about 60 nm; less than about 50 nm; or having a mean diameter of from 1 nm to less than 100 nm; from 10 nm to less than 100 nm; from 20 nm to less than 100 nm; from 30 nm to less than 100 nm; from 40 nm to less than 100 nm; from 50 nm to less than 100 nm; from 10 nm to 90 nm; from 20 nm to 80 nm; or having a mean diameter of from 30 nm to 70 nm. In an embodiment, greater than 99% of the nanoparticles of a nanoparticle population have a mean diameter falling within a described range; greater than about 90% of the microparticles have a mean diameter falling within a described range; greater than about 80% of the microparticles have a mean diameter falling within a described range; greater than about 70% of the microparticles have a mean diameter falling within a described range; greater than about 60% of the microparticles have a mean diameter falling within a described range; greater than about 50% of the microparticles have a mean diameter falling within a described range; greater than about 40% of the microparticles have a mean diameter falling within a described range; greater than about 30% of the microparticles have a mean diameter falling within a described range; greater than about 20% of the microparticles have a mean diameter falling within a described range; or greater than about 10% of the microparticles have a mean diameter falling within a described range.

The term "NHS" as used herein refers to N-hydroxysuccinimide, which is commonly used in organic chemistry or biochemistry as an activating reagent for carboxylic acids.

The phrase "peptide-conjugated fluorophore" as used herein refers to a fluorophore covalently connected with an interested peptide substrate.

The term "STS" as used herein refers to staurosporine, an anti-cancer treatment drug, which can induce cell apoptosis.

The term "TFA" as used herein refers to trifluoroacetic acid, a strong carboxylic acid widely used in organic chemistry.

The term "TIS" as used herein refers to triisopropylsilane, which is an organic compound. It is sometimes used for the peptide cleavage from resin in solid-phase synthesis.

The phrase "unsaturated alkyl" as used herein refers to a branched or unbranched unsaturated hydrocarbon chain comprising a designated number of carbon atoms, and may also be referred to as an "alkenyl" or "alkynyl." For example, a $C_2$-$C_6$ straight or branched alkenyl hydrocarbon chain contains 2 to 6 carbon atoms having at least one double bond, and includes but is not limited to ethenyl, propenyl, iso-propenyl, butenyl, iso-butenyl, tert-butenyl, n-pentenyl, n-hexenyl, and the like. It is also contemplated as within the scope of the present subject matter that "unsaturated alkyl" may also refer to an unsaturated hydrocarbon chain wherein any of the carbon atoms of said unsaturated alkyl are optionally replaced with O, NH, S, or $SO_2$. For example, carbon 2 of 4-pentene can be replaced with O to form (2-propene)oxymethyl. In one embodiment, the "unsaturated alkyl" may be unsubstituted or is substituted by one or more substituents.

The term "a" or "an" as used herein includes the singular and the plural, unless specifically stated otherwise. Therefore, the term "a," "an," or "at least one" can be used interchangeably in this application.

Throughout the application, descriptions of various embodiments use the term "comprising;" however, it will be understood by one of skill in the art, that in some specific instances, an embodiment can alternatively be described using the language "consisting essentially of" or "consisting of."

For the purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter is directed to a cationic fluorescent luminogen exhibiting aggregation-induced/enhanced emission (AIE/AEE) comprising one or more heterocycle units; wherein the luminogen comprises a chemical structure selected from the group consisting of:

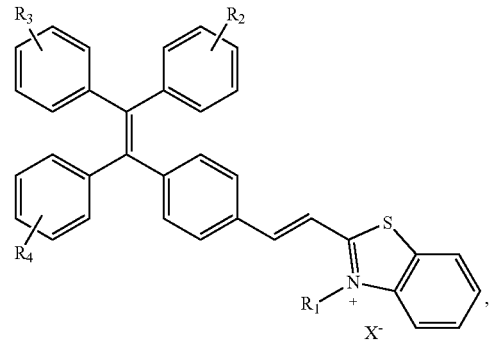

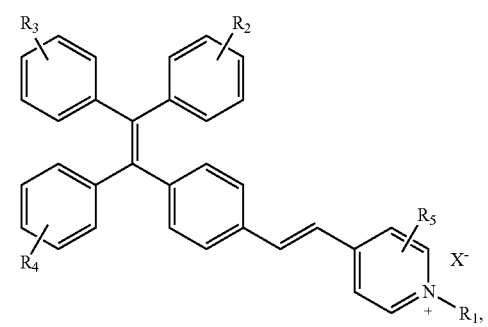

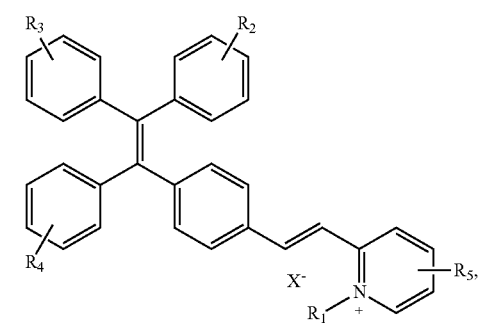

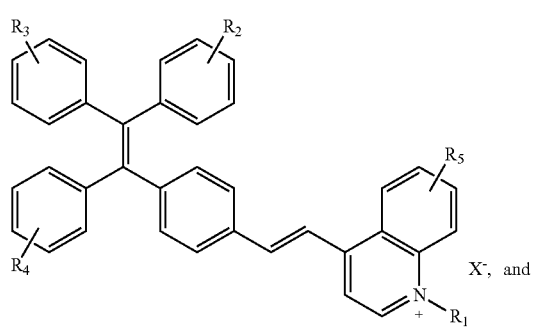

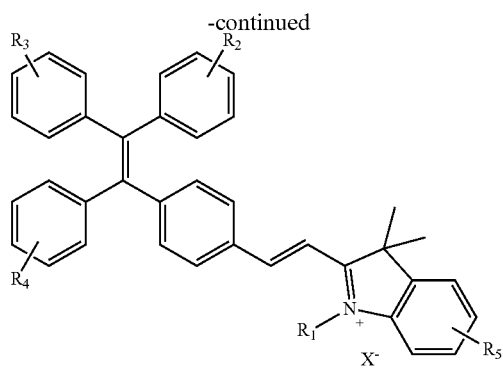

wherein each $R_1$, $R_2$, $R_3$, $R_4$, and $R_5$ is independently selected from the group consisting of H, alkyl, unsaturated alkyl, heteroalkyl, cycloalkyl, heterocycloalkyl, aryl, heteroaryl, $C_nH_{2n+1}$, $C_{10}H_7$, $C_{12}H_9$, $OC_6H_5$, $OC_{10}H_7$, $OC_{12}H_9$, $C_nH_{2n}COOH$, $C_nH_{2n}OH$, $C_nH_{2n}CHO$, $C_nH_{2n}COOC_4O_2N$, $C_nH_{2n}NCS$, $C_nH_{2n}N_3$, $C_nH_{2n}NH_2$, $C_nH_{2n}SH$, $C_nH_{2n}Cl$, $C_nH_{2n}Br$, and $C_nH_{2n}I$; n=0 to 20; and X is a monovalent counterion.

In one embodiment, the luminogen has a long wave fluorescence emission. In another embodiment, X is a monovalent counterion selected from the group consisting of I, Cl, Br, $PF_6$, $ClO_4$, $BF_4$, $BPh_4$, and $CH_3PhSO_3$. In another embodiment, the luminescent materials with AIE/AEE characteristics are dispersed in an aqueous solution. The present subject matter also relates to changing the behavior of luminogen from aggregation-caused quenching (ACQ) to aggregation-induced emission (AIE) through changing the counterions.

The present subject matter also relates to luminescent materials possessing strong, distinct fluorescence in both their crystalline and amorphous states. In another embodiment, the present subject matter relates to the emission of AIE-active luminogens that can be repeatedly changed between two distinguished emission colors by grinding-fuming and grinding-heating processes. In a further embodiment, the present subject matter relates to the emission changes of luminogens through grinding-fuming and grinding-heating processes that are due to the morphological change between crystalline and amorphous states. In another embodiment, the present subject matter relates to AIE/AEE luminogens with excellent optical waveguide behavior.

In a further embodiment, the present subject matter relates to AIE material as a fluorescent staining for mitochondria with high photostability. In another embodiment, the present subject matter relates to luminescent materials that can label a biopolymer.

In another embodiment, the present subject matter relates to luminescent materials that work as selective and sensitive fluorescent chemosensors for detection of $Hg^{2+}$ in aqueous solution. The present subject matter also relates to a thin film of luminescent materials which shows a turn-on switch for $Hg^{2+}$ in aqueous solution. Likewise, the present subject matter also relates to AIE/AEE luminogens that work as selective and sensitive fluorescent chemosensors for detection of ATP in aqueous solution.

In a further embodiment, the present subject matter relates to in vitro and in vivo imaging of cell apoptosis using a bioprobe labeled with heterocycle-functionalized tetraphenylethene (TPE) derivatives.

In one embodiment, the present subject matter relates to three luminogens, TPEBe-I, TPEBe-$ClO_4$, and TPEBe-$PF_6$, the chemical structures of which are shown below. All these luminogens are soluble in common organic solvents, such as THF, toluene, DCM, and chloroform, but are insoluble in water.

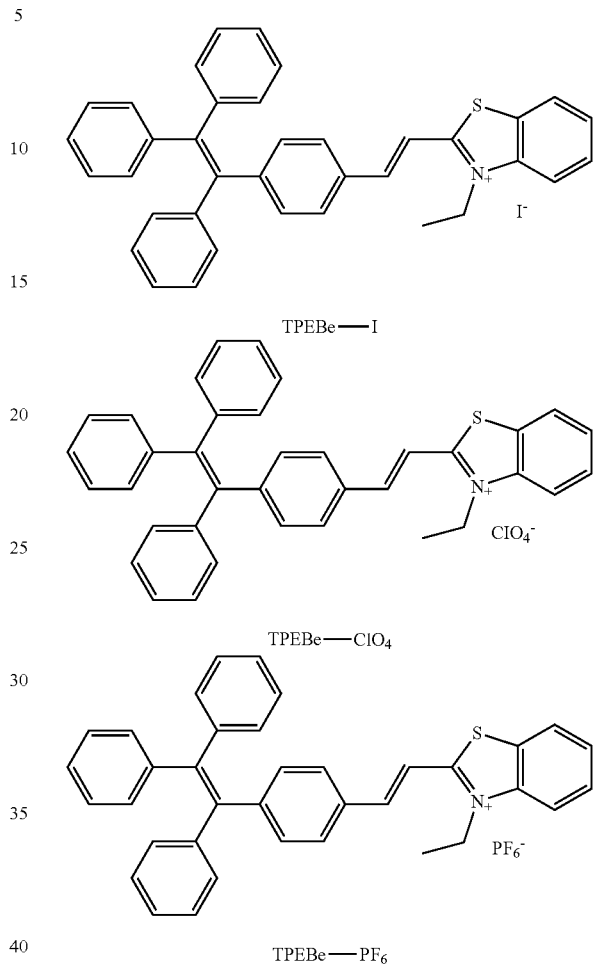

Each of TPEBe-I, TPEBe-$ClO_4$, and TPEBe-$PF_6$ were synthesized via a multistep reaction shown in the reaction scheme below.

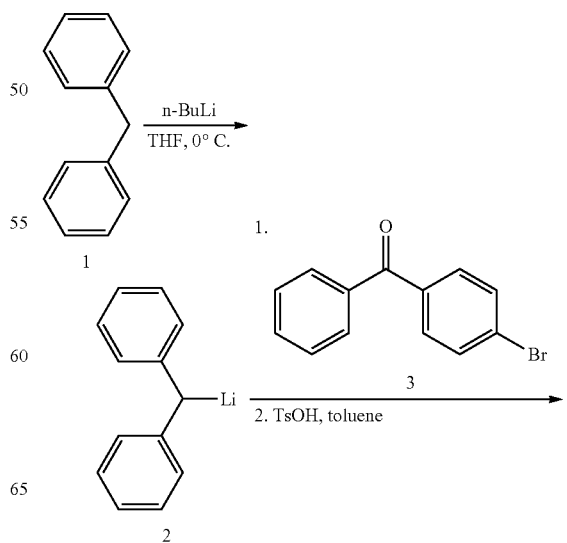

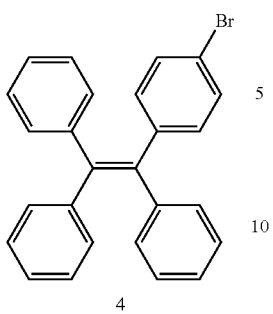

4

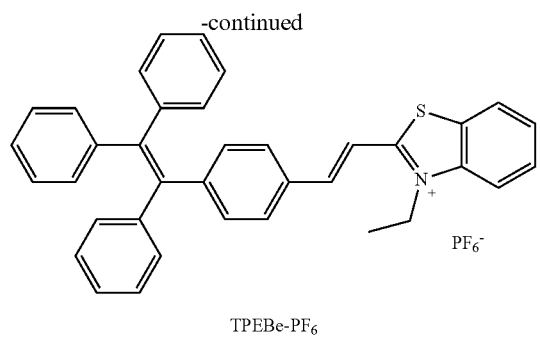

5

TPEBe-PF$_6$

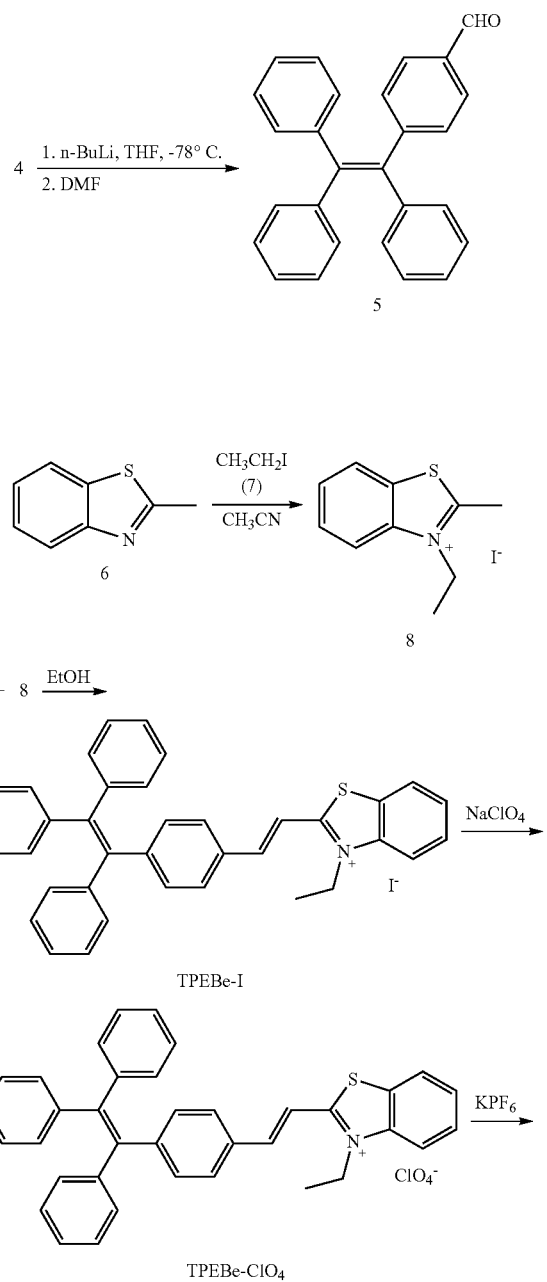

Figure 1:
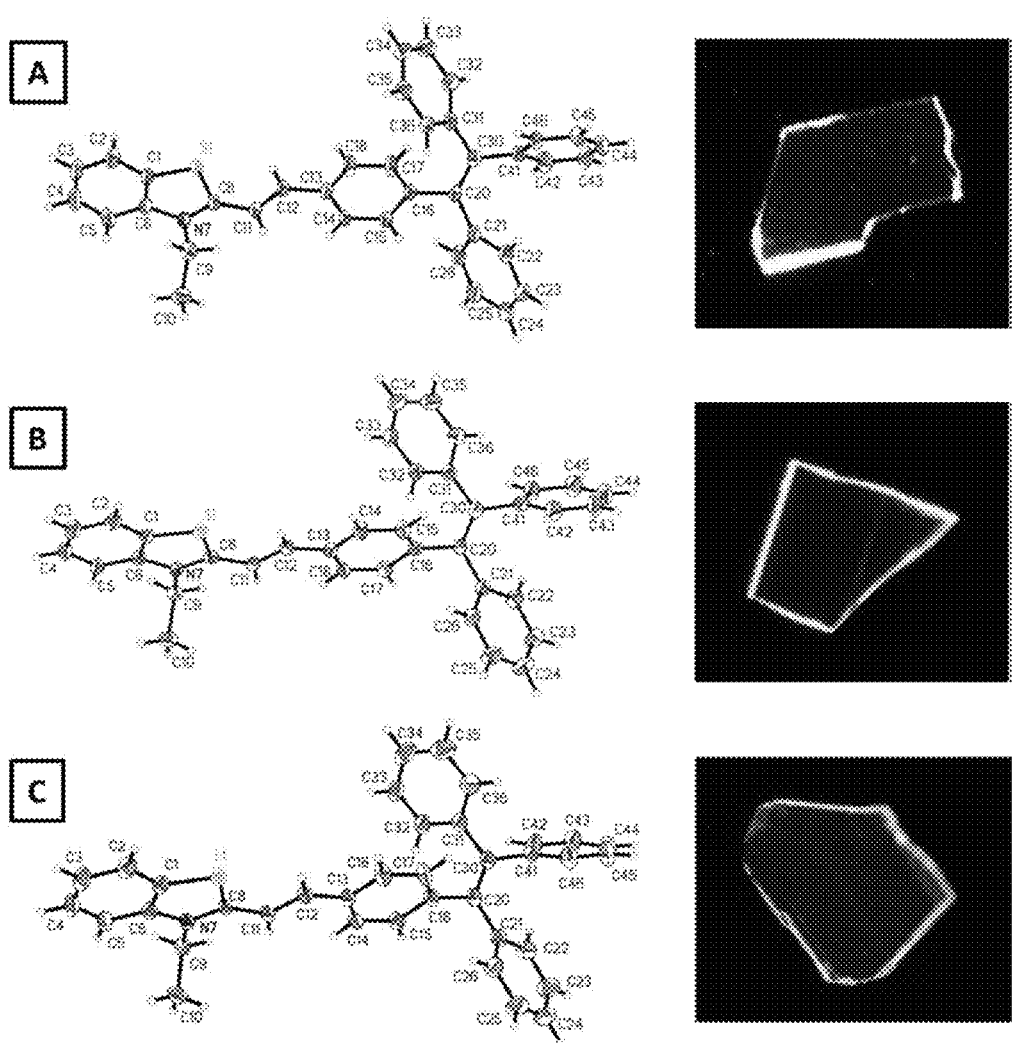
FIG. 1a shows ORTEP drawings of TPEBe-$PF_6$. Inset: fluorescent images of the crystals taken under UV irradiation on a fluorescence microscope.
FIG. 1b shows ORTEP drawings of TPEBe-$PF_6$.2/3 THF. Inset: fluorescent images of the crystals taken under UV irradiation on a fluorescence microscope.
FIG. 1c shows ORTEP drawings of TPEBe-$PF_6$.EtOAc. Inset: fluorescent images of the crystals taken under UV irradiation on a fluorescence microscope.
Figure 2:
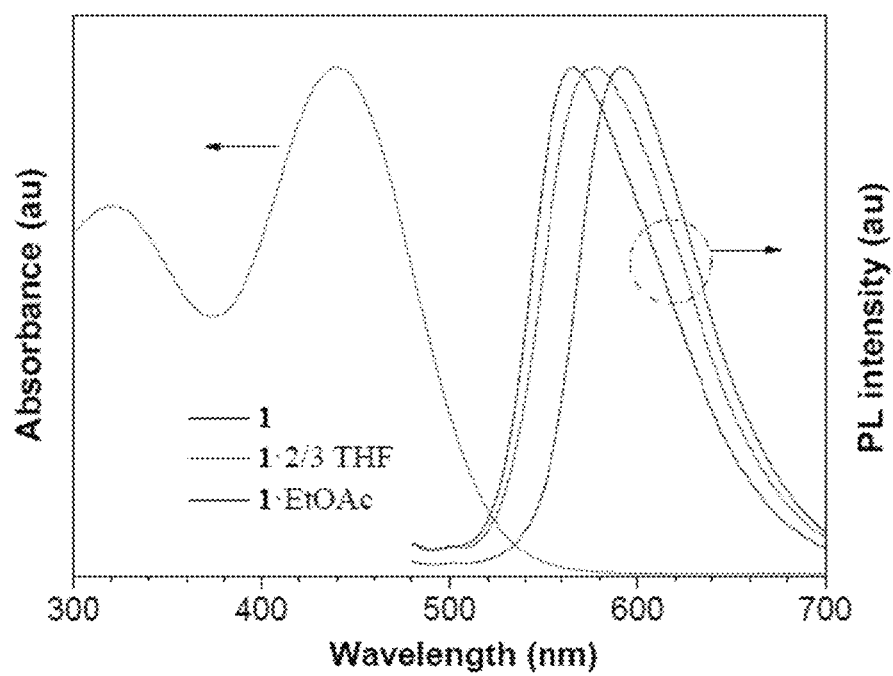
FIG. 2 shows an absorption spectrum of TPEBe-$PF_6$ in THF solution and a photoluminescence spectra of crystals of TPEBe-$PF_6$, TPEBe-$PF_6$.2/3 THF, and TPEBe-$PF_6$.EtOAc.

One embodiment of the present subject matter relates to crystals of TPEBe-PF$_6$, which were obtained by slow evaporation of its DCM/ethanol, THF/hexane, and DCM/ethyl acetate (EtOAc) mixtures. ORTEP drawings of the crystals of TPEBe-PF$_6$ are shown in FIG. 1. The crystals grown from different solvent mixtures emit at different wavelengths with different efficiencies (FIG. 2).

Due to the propeller-shaped TPE unit, all the crystals have a highly twisted conformation. The torsion angles (θ1) between the bridged phenyl ring and the vinyl core of TPE in crystals of TPEBe-PF$_6$, TPEBe-PF$_6$.2/3 THF, and TPEBe-PF$_6$.EtOAc are 70.42, 70.37 and 67.94, respectively, suggesting that the molecular conjugation is in the order of TPEBe-PF$_6$<TPEBe-PF$_6$.2/3 THF<TPEBe-PF$_6$.EtOAc. This agrees well with their observed emission maximum, in which crystals of 1.EtOAc are the redder emitters.

Figure 3:
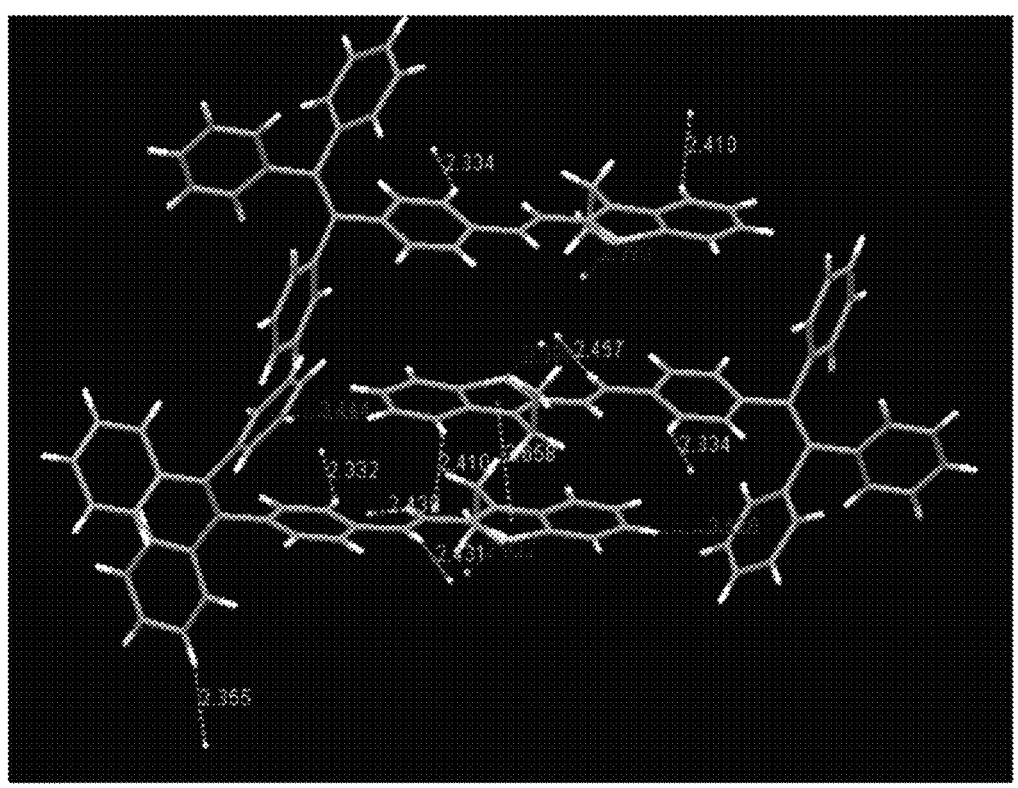
FIG. 3 shows C—H . . . π (red line), π . . . π (pink), C—H . . . F (green line) and S . . . F (purple) interactions in TPEBe-$PF_6$. Anions are omitted for clarity.
Figure 4:
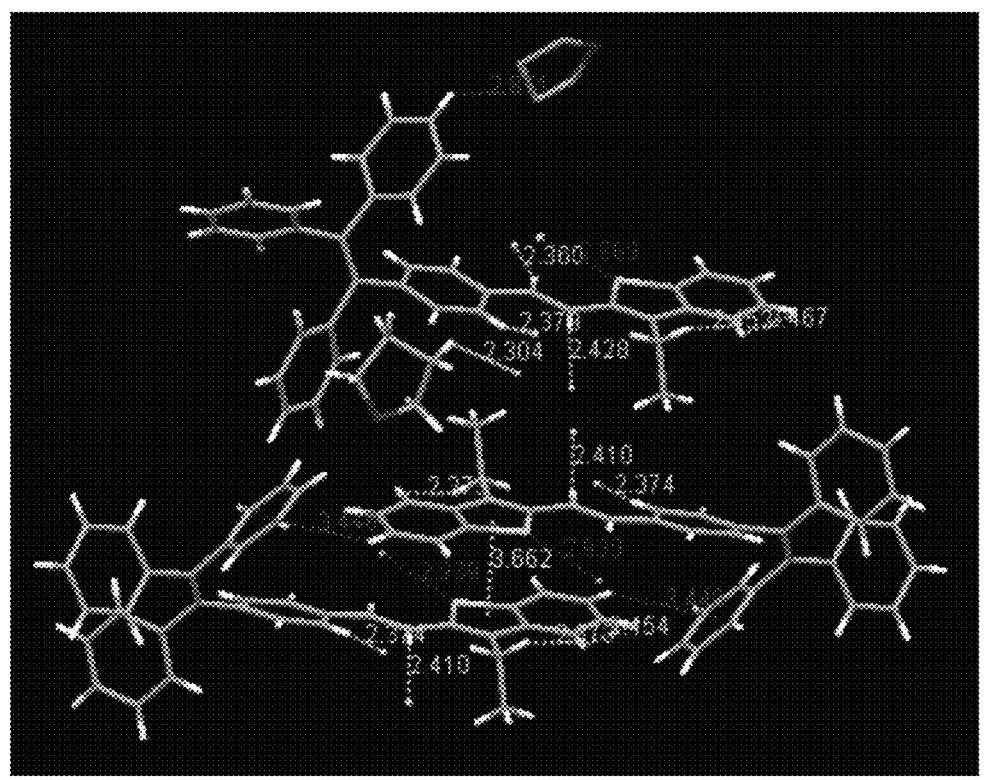
FIG. 4 shows C—H . . . π (red line), π . . . π (pink), C—H . . . F (green line) and S . . . F (purple) interactions in TPEBe-$PF_6$.2/3 THF. Anions are omitted for clarity.
Figure 5:
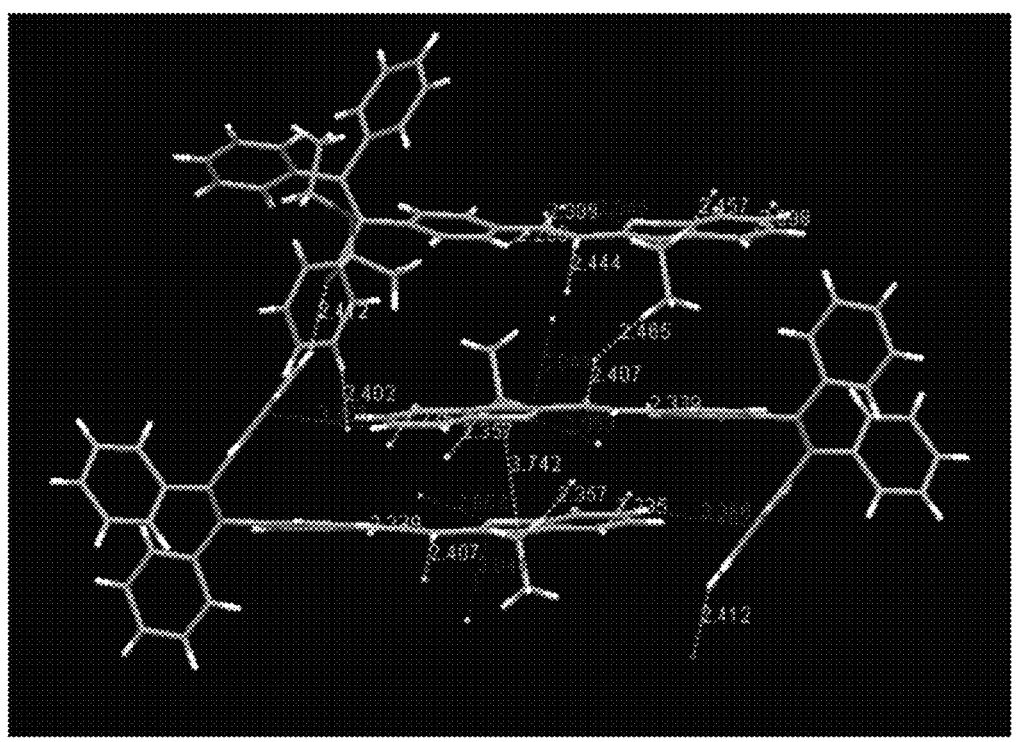
FIG. 5 shows C—H . . . π (red line), π . . . π (pink), C—H . . . F (green line), C—H . . . O (yellow line) and S . . . F (purple) interactions in TPEBe-$PF_6$.EtOAc. Anions are omitted for clarity.

Except weak π . . . π stacking interaction between the benzothiazolium units, multiple C—H . . . π and C—H . . . F hydrogen bonds and S . . . F interaction are observed in all crystals. Additional C—H . . . π and C—H . . . O hydrogen bonds due to interactions with the solvent molecules are also found in crystals of TPEBe-PF$_6$.2/3THF and TPEBe-PF$_6$.EtOAc (FIGS. 3, 4, and 5). These multiple bonds and interactions help further rigidify the molecular conformation, which reduces the energy loss through nonradiative rotational relaxation channel, and thus, enhances the emission efficiency of TPEBe-PF$_6$.2/3 THF and TPEBe-PF$_6$.EtOAc.

Figure 6:
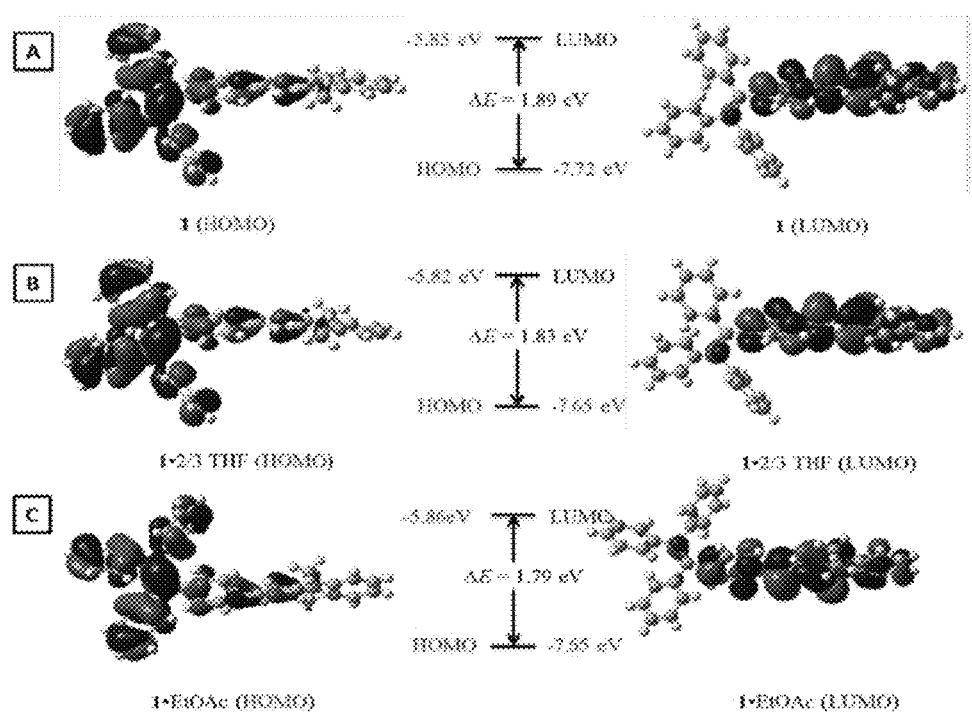
FIG. 6a shows molecular orbital amplitude plots of HOMO and LUMO energy levels of crystals of TPEBe-$PF_6$ calculated using B3LYP/6-31G(d) basis set.
FIG. 6b shows molecular orbital amplitude plots of HOMO and LUMO energy levels of crystals of TPEBe-$PF_6$.2/3THF calculated using B3LYP/6-31G(d) basis set.
FIG. 6c shows molecular orbital amplitude plots of HOMO and LUMO energy levels of crystals of TPEBe-$PF_6$.EtOAc calculated using B3LYP/6-31G(d) basis set.

As shown in FIG. 6, the HOMO and LUMO energy levels of the crystals were calculated using the 3LYP/6-31G* basis set. The HOMO of all crystals is dominated by the orbitals from the TPE unit, while the orbitals from the benzothiazolium component contribute mainly the LUMO energy levels. The energy band gaps of TPEBe-PF$_6$, TPEBe-PF$_6$.2/3 THF and TPEBe-PF$_6$.EtOAc are calculated to be 1.89, 1.83 and 1.79 eV, respectively, nicely correlating with their different emission colors. Clearly, the crystal emission of TPEBe-PF$_6$ can be tuned readily by solvent molecules, which is extraordinary, if not unprecedented in the AIE system.

Figure 7:
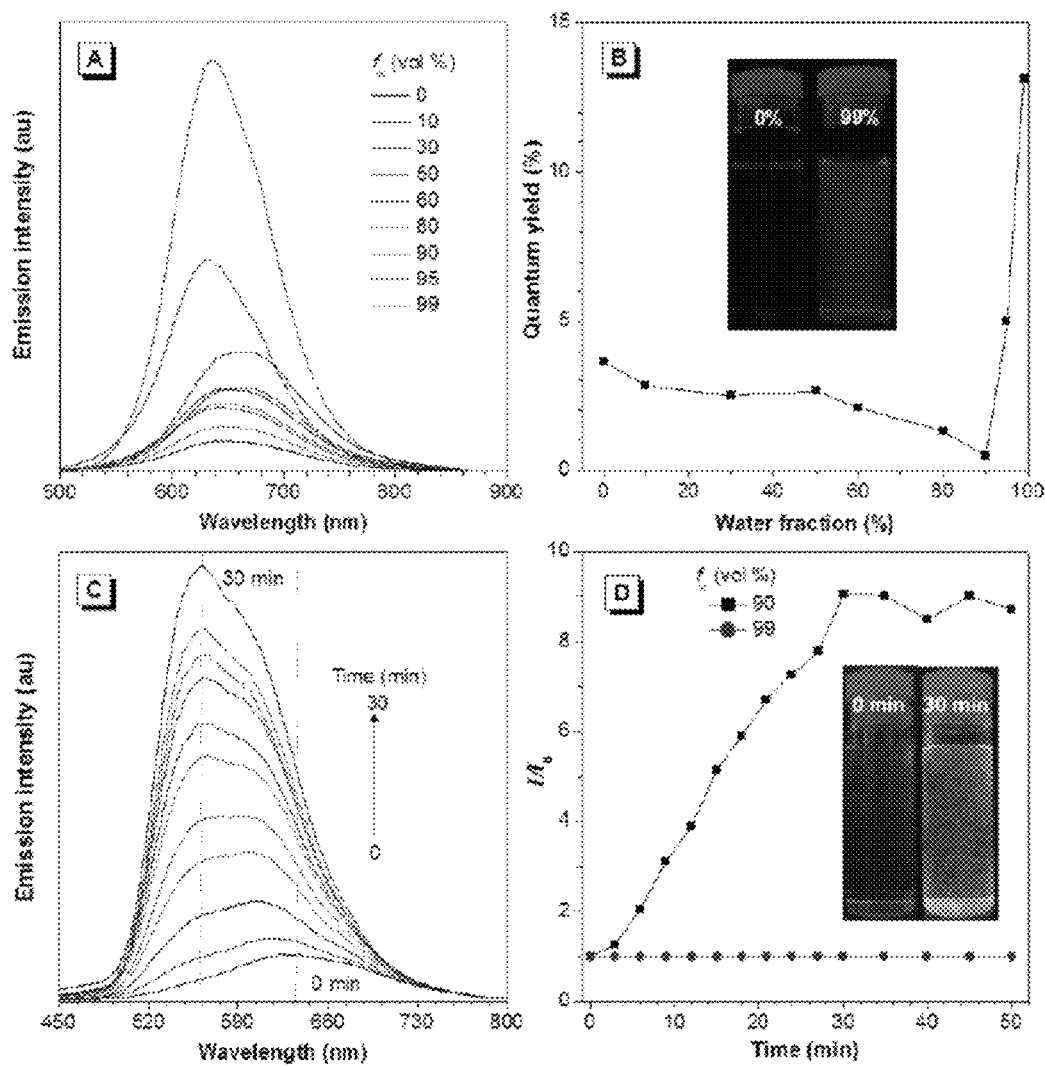
FIG. 7a shows a photoluminescence spectra of TPEBe-$PF_6$ in THF and THF/water mixtures with different water fractions ($f_w$).
FIG. 7b shows plots of fluorescence quantum yields versus the composition of the aqueous mixtures of TPEBe-PF$_6$. Inset: photograph of TPEBe-PF$_6$ in THF/water mixtures at f$_w$ values of 0 and 90 vol %.
FIG. 7c shows the change in the photoluminesnce spectrum of TPEBe-PF$_6$ in 90% aqueous mixtures over time from 0 to 30 min.
FIG. 7d shows the plot of I/I$_0$ value versus time in THF/water mixtures of TPEBe-PF$_6$ at 90 and 99% water content. 1=emission intensity in pure THF solution. Solution concentration: 20 μM; excitation wavelength: 425 nm. Inset: photograph of TPEBe-PF$_6$ in a 90% aqueous mixture at different time intervals (0 and 30 min) taken under 365 nm UV illumination.

In an embodiment, the TPEBe-PF$_6$ luminogen absorbs at 440 nm in diluted THF solution (FIG. 2) due to the intramolecular charge transfer (ICT) from the electron-donating TPE unit to the electron-accepting benzothiazolium unit. Similar to TPE, the TPEBe-PF$_6$ luminogen emits faint photoluminescence at 663 nm with a fluorescence quantum yield (O$_F$) of 3.66% when its diluted solution is photoexcited (FIG. 7a).

When a small amount of water is added to the THF solution, the emission intensity as well as the Φ$_F$ value becomes lower, presumably due to the ICT effect. The higher the water content, the lower is the light emission and the Φ$_F$ value because the solution polarity becomes progressively higher. Interestingly, at a water fraction greater than 90%, the mixture emits even more intensely and efficiently than that of pure THF solution. At 99% water content, the $\Phi_F$ value is 13.12%, which is over 3-fold higher than that in pure THF solution. Therefore, TPEBe-PF$_6$ is clearly AIE-active.

It is believed that restriction of intramolecular rotation (RIR) is the main cause for the AIE phenomenon, which blocks the nonradiative relaxation channel and populates radiative excitons. Since TPEBe-PF$_6$ is not soluble in water, its molecules must have been aggregated in aqueous mixtures with high water fractions. However, at a water fraction less than or equal to 90%, the ICT effect still dominates. Afterwards, the RIR process prevails, which turns TPEBe-PF$_6$ into a strong emitter.

Figure 8:
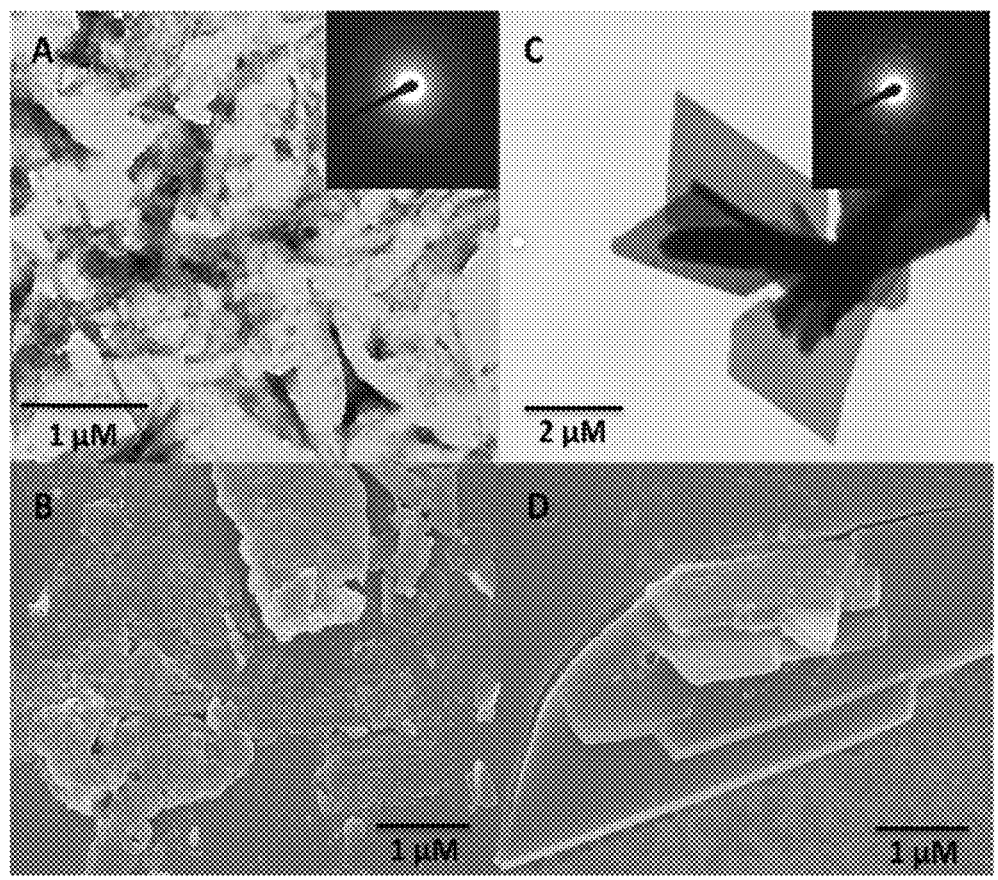
FIG. 8a shows a TEM image of amorphous aggregates of TPEBe-PF$_6$ formed in a 90% aqueous mixture before the solution stood at room temperature for 30 min. Inset: ED patterns of the amorphous aggregates.
FIG. 8b shows a SEM image of amorphous aggregates of TPEBe-PF$_6$ formed in a 90% aqueous mixture before the solution stood at room temperature for 30 min.
FIG. 8c shows a TEM image of crystalline aggregates of TPEBe-PF$_6$ formed in a 90% aqueous mixture after the solution stood at room temperature for 30 min. Inset: ED patterns of the crystalline aggregates.
FIG. 8d shows a SEM image of crystalline aggregates of TPEBe-PF$_6$ formed in a 90% aqueous mixture after the solution stood at room temperature for 30 min.

In yet another embodiment, the emission intensity and color of a freshly prepared 90% aqueous mixture change when standing at room temperature with time. As depicted in FIG. 7c, the photoluminescence spectrum is initially peaked at 644 nm, which shifts progressively to 566 nm, accompanied with a remarkable increase in emission intensity. In contrast, this phenomenon was not observed in the 99% aqueous mixture (FIG. 7d). The ultimate emission maximum is close to that of crystals, implying that the aggregates crystallize over time. This is supported by the TEM and SEM images and ED patterns shown in FIG. 8.

The aggregates formed in the 90% aqueous mixture seem to possess a more loose structure than those in the THF/water mixture with a 99% water fraction. This provides a freer volume for the molecules to reorient and pack into a more ordered fashion. The unusual blue-shift observed in the crystalline phase, on the other hand, may be due to the conformation twisting of the aromatic rings of TPEBe-PF$_6$ in order to fit into the crystalline lattice. Without such constraint, the molecules in the amorphous phase may assume a more planer conformation, and therefore, show a redder emission.

Figure 9:
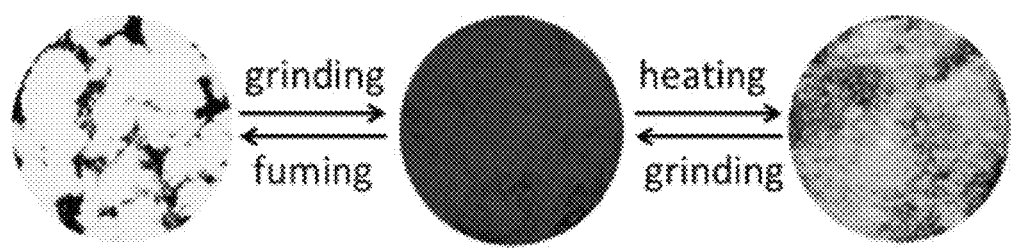
FIG. 9 shows switching the solid-state emission of TPEBe-PF$_6$ by repeated grinding-fuming and grinding-heating processes. The photographs were taken under 365 nm UV irradiation.
Figure 10:
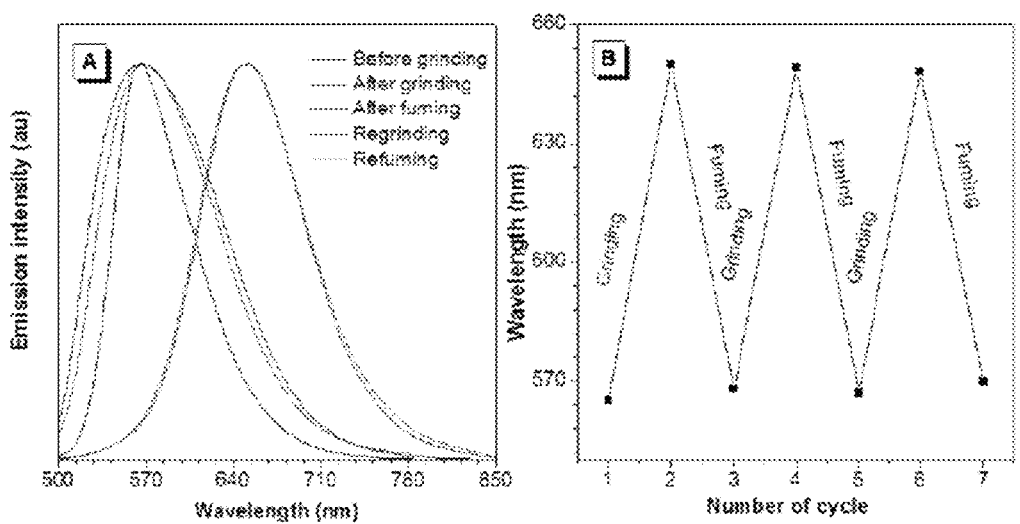
FIG. 10a shows a change in the photoluminescence spectrum of TPEBe-PF$_6$ by grinding-fuming process.
FIG. 10b shows repeated switching of the solid-state fluorescence of TPEBe-PF$_6$ by repeated grinding and fuming cycles.
Figure 11:
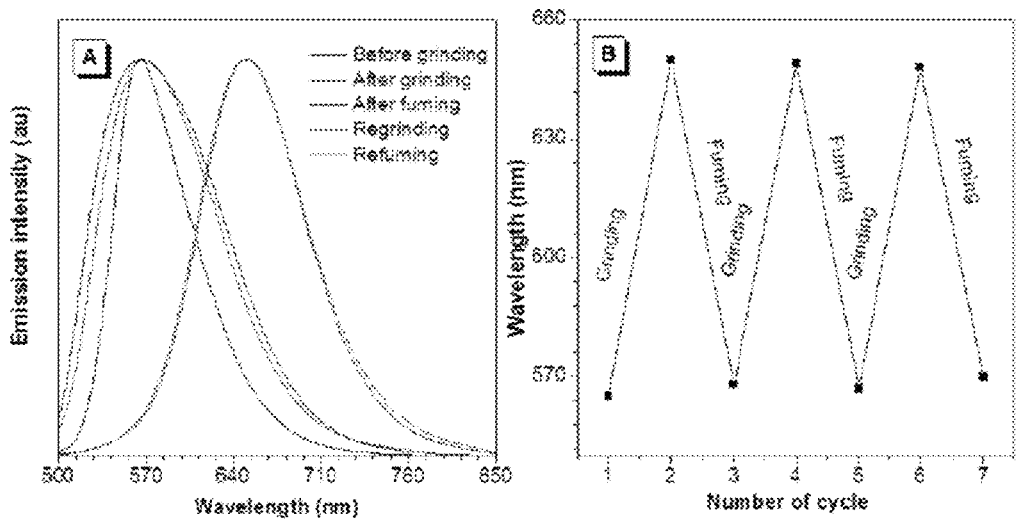
FIG. 11a shows a change in the photoluminescence spectrum of TPEBe-PF$_6$ by grinding-heating process at 150° C. for 10 min.
FIG. 11b shows repeated switching of the solid-state fluorescence of TPEBe-PF$_6$ by repeated grinding and heating cycles.

In one embodiment, after gentle grinding using a pestle or a mortar, red powders are formed, which show red photoluminescence at 650 nm (FIGS. 9 and 10a). After fuming with acetone vapor for 10 min, the initial (yellow) appearance reappears (FIG. 10a). The conversion between yellow and red emission colours can be repeated many times without fatigue, as these stimuli are nondestructive (FIG. 10b). On the other hand, heating the ground sample at 150° C. for 10 min changes its colour from red to orange (FIGS. 9 and 11a). Again, such switching is reversible and suffers little wavelength-shift after many cycles (FIG. 11b).

Figure 12:
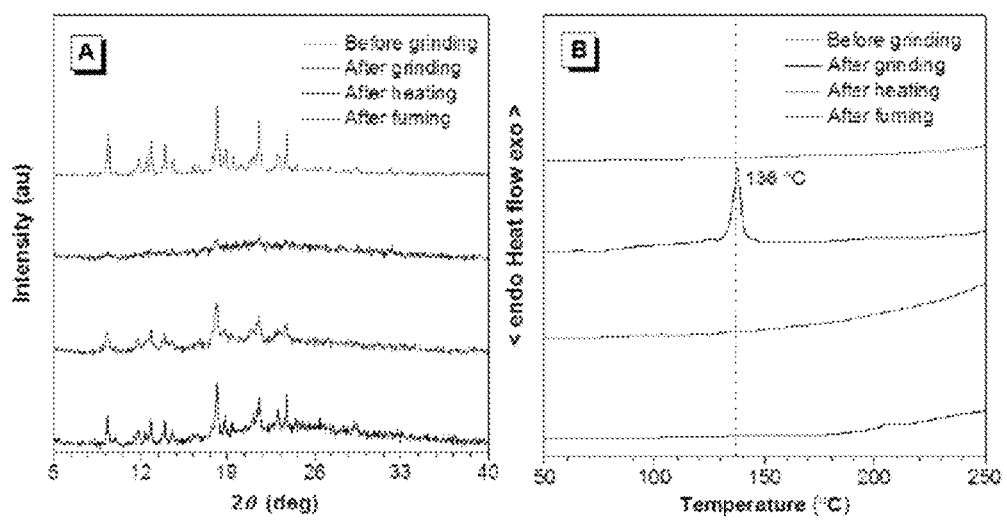
FIG. 12a shows XRD diffractograms of TPEBe-PF$_6$ at different aggregated phases recorded at a heating rate of 10° C./min.
FIG. 12b shows DSC thermograms of TPEBe-PF$_6$ at different aggregated phases recorded at a heating rate of 10° C./min.

TPEBe-PF$_6$ was analyzed at different aggregated states by powder X-ray diffraction (XRD). The XRD diffractogram of the untreated sample exhibits many sharp diffraction peaks, indicative of its crystalline nature (FIG. 12a). On the contrary, the ground sample is amorphous as its diffractogram exhibits only a big, diffuse halo. When the red powders are thermal-treated or fumigated with solvent vapor, sharp diffraction peaks emerge again. This suggests that the amorphous powders crystallize upon solvent fumigation or thermal treatment. Therefore, the mechanochromism observed in TPEBe-PF$_6$ is associated with the morphology change from the crystalline to amorphous state and vice versa. It is noteworthy that the fumed sample shows much sharper peaks than the thermal-treated one, implying the stronger effect of solvent fumigation on the crystallization of TPEBe-PF$_6$ than the thermal process. This also explains why the red amorphous powders cannot be completely recovered into yellow-emissive crystals by the latter method.

TPEBe-PF$_6$ was analyzed by differential scanning calorimetry (DSC). The DSC curve of crystals of TPEBe-PF$_6$ recorded during the heating scan is basically a straight line parallel to the abscissa (FIG. 12b). On the contrary, an endothermic peak at 138° C. is detected in the ground sample. Thermogravimetric analysis shows that TPEBe-PF$_6$ exhibits a 5% weight loss at 280° C. Therefore the peak at 138° C. should not stem from the decomposition of the molecule or its glass-transition temperature as such thermal transition involves only a small enthalpy change. Instead, it is more likely to be associated with the crystallization of the luminogen. No signals were detected in thermal-treated and fumed samples, as they are crystalline.

Figure 13:
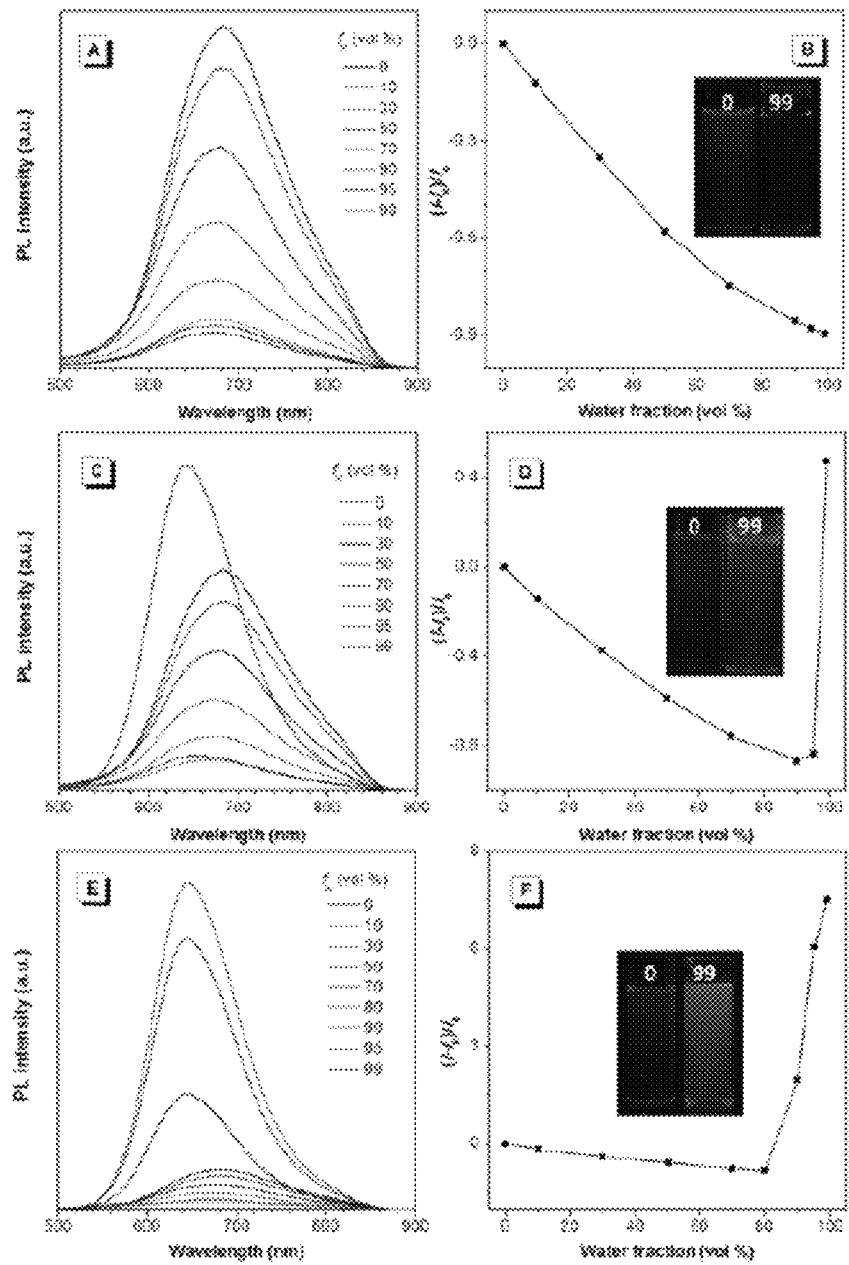
FIG. 13a shows a photoluminescence spectrum of TPEBe-I in DMSO and DMSO/water mixtures with different water fractions (f$_w$).
FIG. 13b shows a plot of (I−I$_0$)/I$_0$ versus the composition of the aqueous mixtures of TPEBe-I. I$_0$=emission intensity in pure DMSO solution. Solution concentration: 20 μM; excitation wavelength: 420 nm. Inset: photograph of TPEBe-I in DMSO/water mixtures with f$_w$ values of 0 and 99 vol %.
FIG. 13c shows a photoluminescence spectrum of TPEBe-ClO$_4$ in DMSO and DMSO/water mixtures with different water fractions (f$_w$).
FIG. 13d shows a plot of (I−I$_0$)/I$_0$ versus the composition of the aqueous mixtures of TPEBe-ClO$_4$. I$_0$=emission intensity in pure DMSO solution. Solution concentration: 20 μM; excitation wavelength: 420 nm. Inset: photograph of TPEBe-ClO$_4$ in DMSO/water mixtures with f$_w$ values of 0 and 99 vol %.
FIG. 13e shows a photoluminescence spectrum of TPEBe-PF$_6$ in DMSO and DMSO/water mixtures with different water fractions (f$_w$).
FIG. 13f shows a plot of (I−I$_0$)/I$_0$ versus the composition of the aqueous mixtures of TPEBe-PF$_6$. I$_0$=emission intensity in pure DMSO solution. Solution concentration: 20 μM; excitation wavelength: 420 nm. Inset: photograph of TPEBe-PF$_6$ in DMSO/water mixtures with f$_w$ values of 0 and 99 vol %.

In another embodiment, as shown in FIG. 13, TPEBe-I, TPEBe-ClO$_4$, and TPEBe-PF$_6$ luminogens show moderate emission in DMSO solution with a similar fluorescence quantum yield ($\Phi_F$) of about 2.00% when its diluted solution is photoexcited at 420 nm. This is due to the intramolecular charge transfer (ICT) from the electron-donating TPE group to the electron-accepting benzothiazolium unit. Moderate emission is generated by the partial rotation of the phenyl group in the TPE unit. Increasing the water fraction in the DMSO solution results in decreased emission for all luminogens at the beginning, presumably due to the effect of polarity for the ICT process. The higher the water content, the lower is the light emission because the solution polarity becomes higher progressively. Interestingly, when the water fraction is more than 90%, the emission continues to decrease for TPEBe-I (FIGS. 13a and 13b). In sharp contrast, both TPEBe-ClO$_4$ and TPEBe-PF$_6$ exhibit the reversed trend of emission change (FIGS. 13c-13f). In the 99% aqueous mixture, the TPEBe-I become nearly non-emissive in comparison to the pure DMSO solution, while the emission color also turns from red to dark under 365 nm UV illumination (Inset in FIG. 13b). Nevertheless, both TPEBe-ClO$_4$ and TPEBe-PF$_6$ emit a more intense bright red color under 365 nm UV illumination (Insets in FIGS. 13d and 13f).

Figure 14:
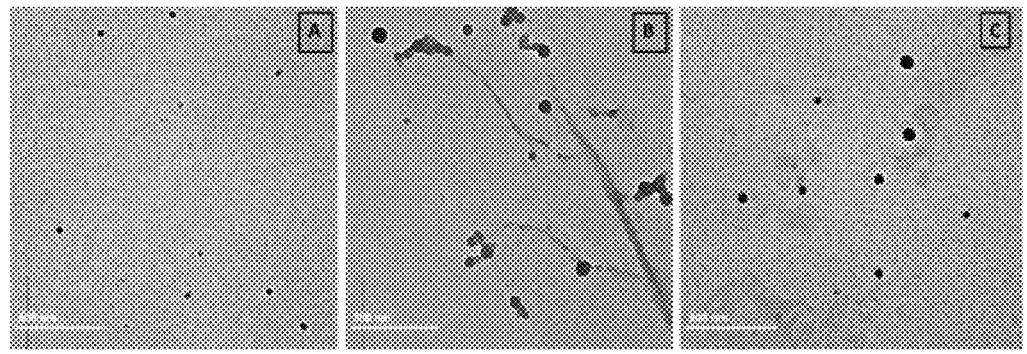
FIG. 14a shows a TEM image of TPEBe-I in a 99% aqueous mixture.
FIG. 14b shows a TEM image of TPEBe-ClO$_4$ in a 99% aqueous mixture.
FIG. 14c shows a TEM image of TPEBe-PF$_6$ in a 99% aqueous mixture.
Figure 15:
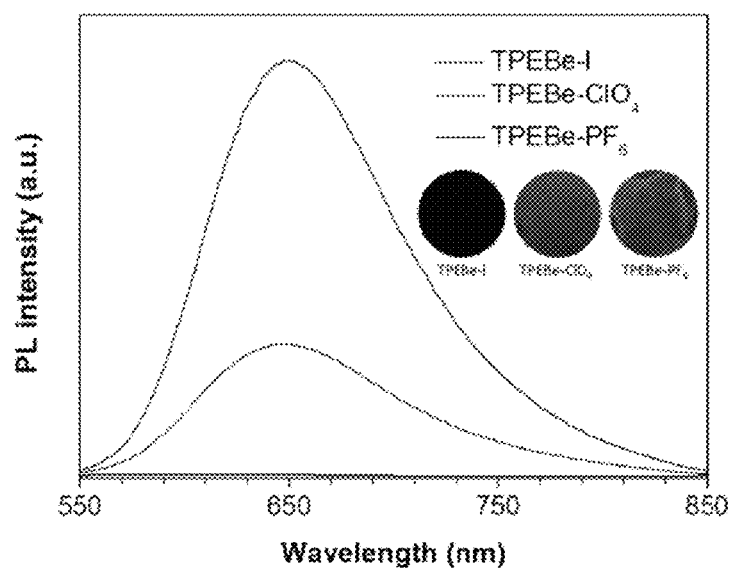
FIG. 15 shows a photoluminescence spectra of TPEBe-I, TPEBe-ClO$_4$, and TPEBe-PF$_6$ in solid film. Inset: Photographs of TPEBe-I, TPEBe-ClO$_4$, and TPEBe-PF$_6$ in solid film taken under 365 nm UV illumination.

In another embodiment, the luminogens aggregate in mixtures with large amounts of water due to their poor solubility in water. TEM images, shown in FIG. 14, demonstrate the existence of nanoparticles having an average size of ca. 50-100 nm in the 99% aqueous mixture, indicating that all molecules aggregated into nanoparticles. The photoluminescence spectra of the luminogens are shown in FIG. 15. The quantum yield of TPEBe-I in the amorphous solid state was measured at approximately 0%, whereas that of TPEBe-ClO$_4$ and TPEBe-PF$_6$ was measured at 25.69% and 26.45%, respectively. Iodine ions are well-known as effective quenchers of fluorescence. This is due to their heavy atom effect, which accelerates the rate of intersystem crossing in luminogen material. TPEBe-I molecules exist in the solution state in the form of solvent separated ion pairs; thus the quenching effect of iodine ions is disabled. The quenching effect of iodine ions, however, is aroused in the condensed phase due to the formation of close contact ion pairs. Consequently, nearly no emission is observed for TPEBe-I in the aggregate or solid state. Evidently, the TPEBe-I exhibits ACQ. The emission of the luminogen is not affected in the solution state when the counterions are changed into ClO$_4$ or PF$_6$. However, the quenching effect from the iodine ions is eliminated and the TPEBe-ClO$_4$ and TPEBe-PF$_6$ luminogens display their intrinsic AIE behaviour in the condensed phase.

This displacement strategy of counterions provides a simple and novel method for changing the ACQ behaviour of a luminogen to AIE behavior. Furthermore, various sizes of counterions can interact with the cationic ClO$_4$ and PF$_6$ ions, which gives rise to a diverse emission efficiency of the corresponding luminogens in the solid state. Accordingly, the present subject matter is also related to adjusting the emission efficiency of a luminogen by adjusting the counterion in the condensed phase.

Figure 16:
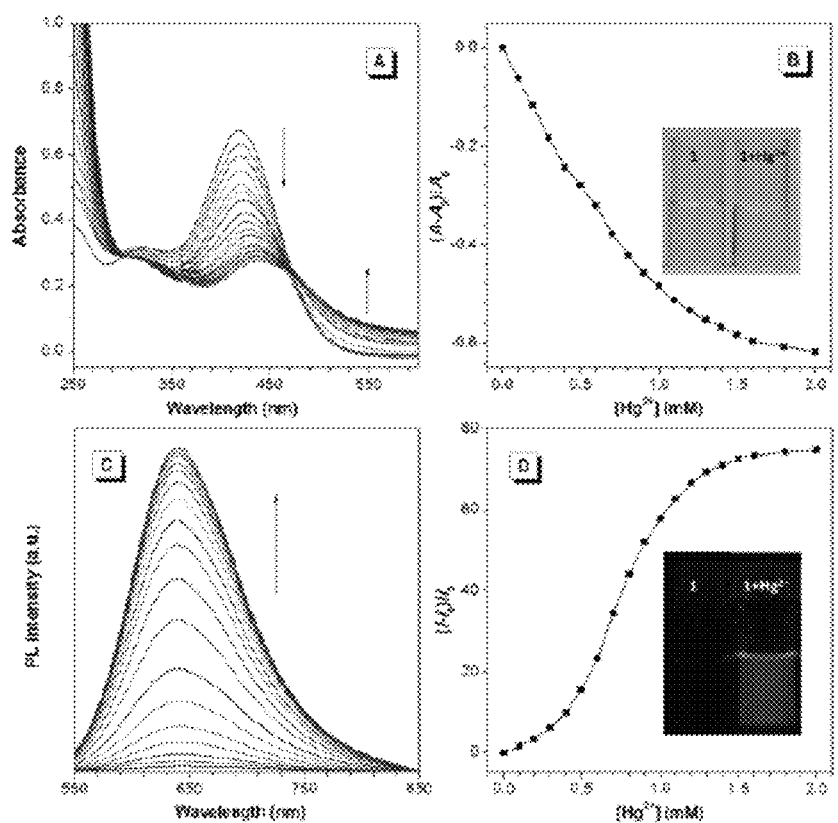
FIG. 16a shows the changes of UV-Vis spectra of TPEBe-I in the aqueous buffer (pH 7.4, 20 mM HEPES buffer with 1% DMSO) in the presence of different concentrations of Hg$^{2+}$ (0-2.0 mM).
FIG. 16b shows a plot of (A−A$_0$)/A$_0$ value versus concentration of Hg$^{2+}$ in the aqueous buffer (pH 7.4, 20 mM HEPES buffer with 1% DMSO). A$_0$=absorbance at 420 nm in absence of Hg$^{2+}$. Inset: photographs of TPEBe-I in the aqueous buffer (pH 7.4, 20 mM HEPES buffer with 1% DMSO) with [Hg$^2$] of 0 and 2.0 mM taken under daylight.
FIG. 16c shows the changes of photoluminescence spectra of TPEBe-I in the aqueous buffer (pH 7.4, 20 mM HEPES buffer with 1% DMSO) in the presence of different concentrations of Hg$^{2+}$ (0-2.0 mM).
FIG. 16d shows a plot of (I−I$_0$)/I$_0$ value versus concentration of Hg$^{2+}$ in the aqueous buffer (pH 7.4, 20 mM HEPES buffer with 1% DMSO). I$_0$=the emission intensity at 640 nm in absence of Hg$^{2+}$. Inset: photographs of TPEBe-I in aqueous buffer with [Hg$^{2+}$] of 0 and 2.0 mM taken under 365 nm UV illumination. Solution concentration: 20 μM; excitation wavelength: 480 nm.

It is well-known that $Hg^{2+}$ possesses a high binding affinity for iodine ions, thereby forming $HgI_2$. Accordingly, in one embodiment, the present subject matter relates to the use of $Hg^{2+}$ to bind to iodine ions in TPEBe-I in order to restore the emission of the cationic luminogen. As shown in FIG. 16, upon the addition of $Hg^{2+}$ into the aqueous solution of TPEBe-I, the lowest energy absorption peak at 420 nm decreased gradually. In addition, the spectrum slightly red-shifted with increasing concentration of $Hg^{2+}$. At the same time, the presence of well-define points at about 300 and 480 nm indicated that only two species coexisted in the equilibrium. Notably, the absorption tails appear in the long wavelength region after addition of $Hg^{2+}$, which indicates increased aggregation based on the Mie effect of particles. In addition, the solution color of TPEBe-I is changed from yellow to colorless, demonstrating that TPEBe-I shows colorimetric sensing for $Hg^{2+}$. Furthermore, the emission intensity of TPEBe-I obviously increased after the addition of $Hg^{2+}$ (FIG. 16c) when it is photoexcited at the isobestic point (480 nm). When the concentration of $Hg^{2+}$ is 2.0 mM, the emission intensity of TPEBe-I is enhanced 80-fold. Moreover, the emission color also changes from dark into bright red under 365 nm UV illumination. Accordingly, another embodiment of the present subject matter relates to the use of TPEBe-I luminogens as an "off-on" sensor for $Hg^{2+}$ in aqueous solution.

Figure 17:
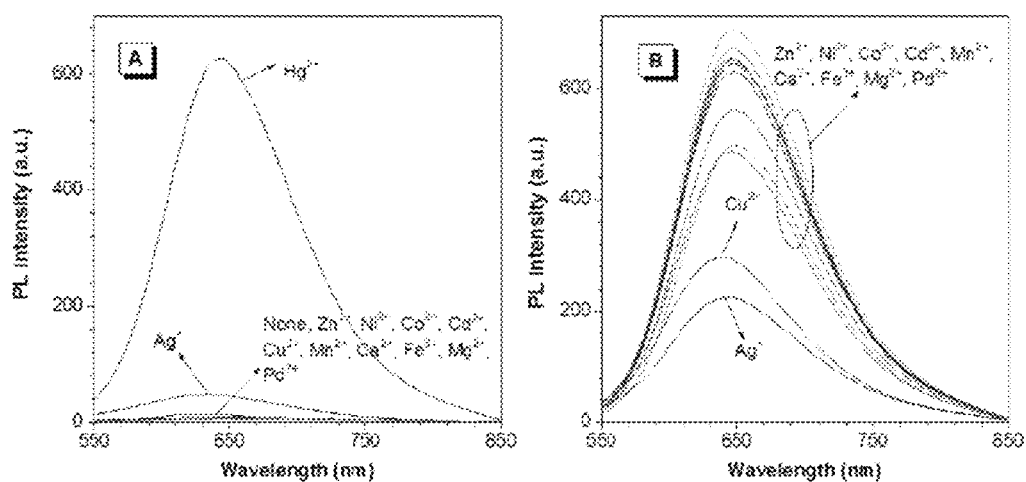
FIG. 17a shows the change of photoluminescence spectra of TPEBe-I in the aqueous buffer (pH 7.4, 20 mM HEPES buffer with 1% DMSO) in the presence of different concentrations of varies metal ions (2.0 mM).
FIG. 17b shows the change of photoluminescence spectra of TPEBe-I in the aqueous buffer (pH 7.4, 20 mM HEPES buffer with 1% DMSO) in the presence of both different concentrations of varies metal ions (2.0 mM) and Hg$^{2+}$ (2.0 mM).
Figure 18:
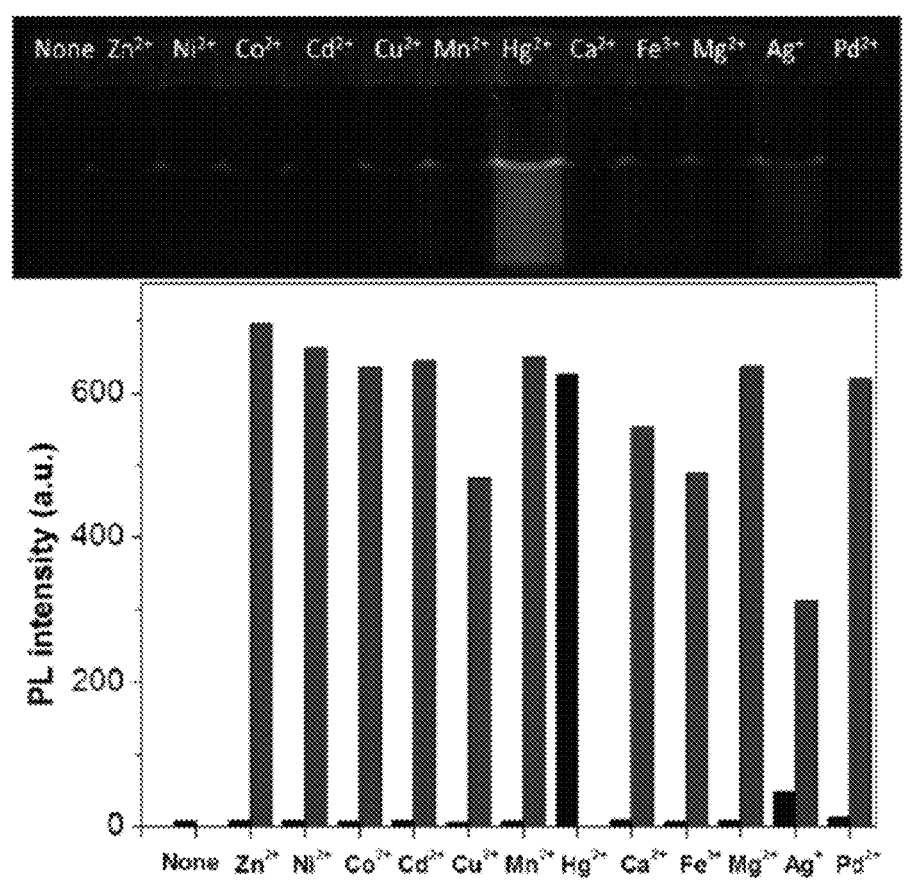
FIG. 18 shows photographs of TPEBe-I in aqueous buffer (pH 7.4, 20 mM HEPES buffer with 1% DMSO) with various metal ions (2.0 mM) taken under 365 nm UV illumination.

In addition, the present subject matter relates to using the TPEBe-I luminogen as a fluorescent sensor for $Hg^{2+}$. FIGS. 17 and 18 demonstrate TPEBe-I's selectivity and sensitivity for detecting $Hg^{2+}$ over other metal ions, including $Zn^{2+}$, $Ni^{2+}$, $Co^{2+}$, $Cd^{2+}$, $Cu^{2+}$, $Mn^{2+}$, $Hg^{2+}$, $Ca^{2+}$, $Fe^{3+}$, $Mg^{2+}$, $Ag^+$ and $Pd^{2+}$. As shown in FIGS. 17 and 18, only $Hg^{2+}$ showed remarkable emission enhancement, whereas the other metal ions showed only negligible changes in the emission of TPEBe-I. Furthermore, the presence of other metal ions in the same amount as that of $Hg^{2+}$ does not interfere with TPEBe-I's response to $Hg^{2+}$. As shown in FIG. 18, TPEBe-I still exhibits enhanced emission due to the presence of $Hg^{2+}$ even in the presence of other metal ions in the same amount as $Hg^{2+}$ (2.0 mM). Therefore, in one embodiment, TPEBe-I can be used as a highly selective fluorescent sensor for $Hg^{2+}$ over other competitive metal ions in aqueous solution.

Figure 19:
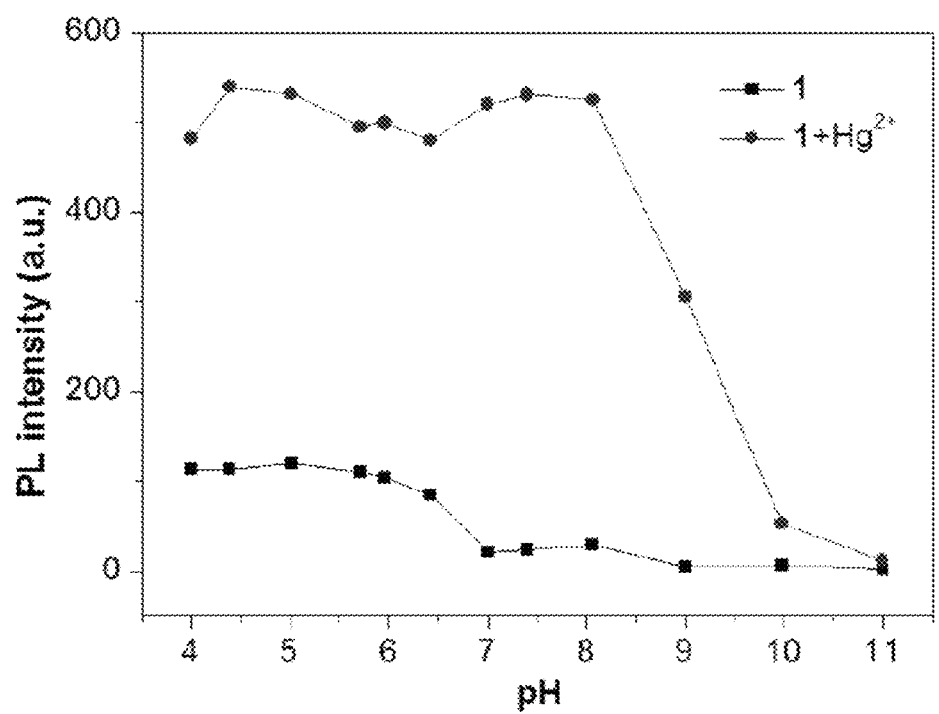
FIG. 19 shows variation in photoluminescence intensity of TPEBe-I (20 μM) in aqueous solutions with and without Hg$^{2+}$ (100 equiv), as a function of pH at λ$_{em}$=640 nm.

Since pH can affect the emission intensity of fluorescent sensors, FIG. 19 shows the photoluminescence emission spectra of TPEBe-I in the presence and absence of $Hg^{2+}$ (2.0 mM) at various pH values. As shown in FIG. 19, TPEBe-I in the absence of $Hg^{2+}$ exhibits relatively higher emission intensity under acidic conditions (pH<7). This is likely due to protons combining with iodine ions, leading to a faint increase in emission. In contrast, under basic conditions (pH≥7), TPEBe-I in the absence of $Hg^{2+}$ is weakly emissive due to the quenching effect of the iodine ions. In the presence of $Hg^{2+}$, the emission intensity of TPEBe-I is greatly enhanced in acidic and neutral conditions. Specifically, the emission intensity of TPEBe-I is greatly enhanced at a pH ranging from 4 to 8. The emission intensity decreases at a pH greater than 8, but is still higher than the emission intensity of TPEBe-I in the absence of $Hg^{2+}$. When the pH is 11, the emission intensity is barely enhanced by addition of $Hg^{2+}$. The lower emission intensity of TPEBe-I under more basic conditions is attributed to the formation of $Hg(OH)_2$, thereby reducing the amount of free $Hg^{2+}$. In addition, the hydroxyl group (OH) in basic conditions can destroy the structure of TPEBe-I, resulting in inactivation of its sensing ability.

Accordingly, the present subject matter in one aspect is directed to the use of a TPEBe-I luminogen as a fluorescent sensor for $Hg^{2+}$ in both neutral and acidic conditions. In one embodiment, the fluorescent TPEBe-I can be used as a fluorescent sensor for $Hg^{2+}$ in a solution at a pH of 4 to 11, preferably 4 to 9, more preferably 4 to 8.

Figure 20:
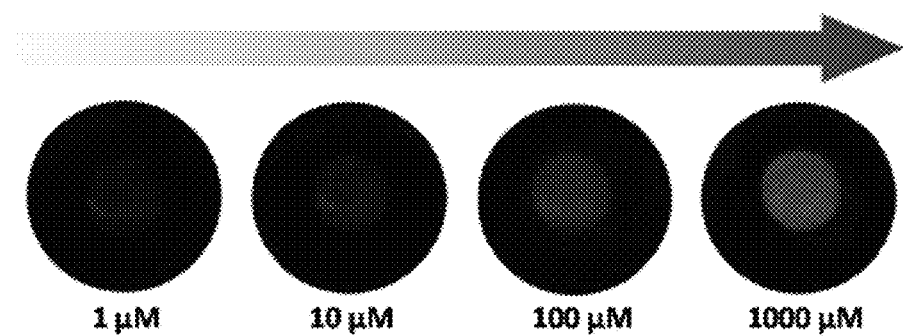
FIG. 20 shows photographs of TPEBe-I in solid film in the presence of different concentration of Hg$^{2+}$ (5 μL) in water taken under 365 nm UV illumination.

In another embodiment, a solid-state fluorescent probe for the detection of $Hg^{2+}$ was developed using the TPEBe-I luminogen. FIG. 20 shows photographs of TPEBe-I in solid film in the presence of different concentrations of $Hg^{2+}$ (5 µL) in water taken under 365 nm UV illumination. As shown, the spots of film polluted by the aqueous solution containing $Hg^{2+}$ changed to a red color with varying degrees while the untreated surrounding areas show the initial dark color. This illustrates that the solid-state film of TPEBe-I has a very sensitive response to $Hg^{2+}$ in a pure aqueous solution. Therefore, one embodiment of the present subject matter relates to the use a TPEBe-I solid-state fluorescent probe for detecting and tracking the amount of $Hg^{2+}$ in an aqueous solution. In one embodiment, the detection amount can reach 1 µM (~220 ppm).

Figure 21:
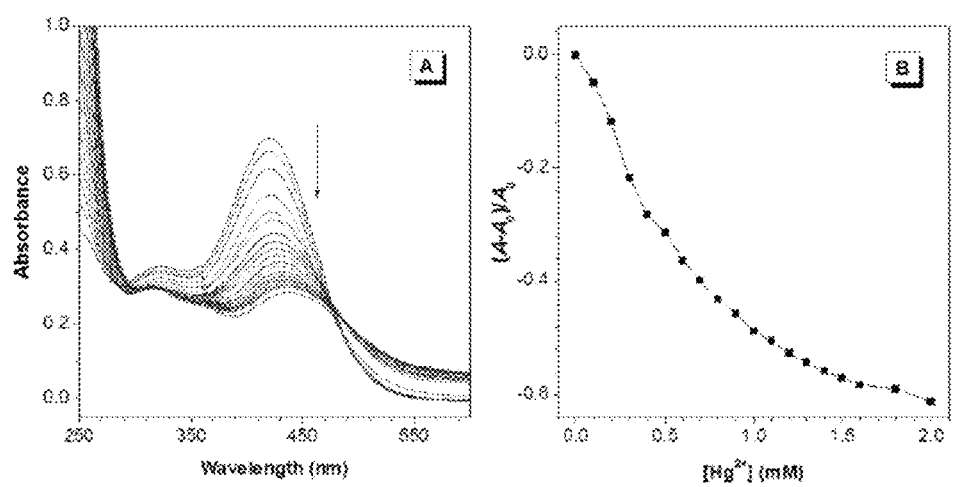
FIG. 21a shows the change of UV-Vis spectra of TPEBe-ClO$_4$ in the aqueous buffer (pH 7.4, 20 mM HEPES buffer with 1% DMSO) in the presence of different concentrations of Hg$^{2+}$ (0-2.0 mM).
FIG. 21b shows a plot of $(A-A_0)/A_0$ value versus concentration of $Hg^{2+}$ in 99% aqueous buffer (pH 7.4, 20 mM HEPES buffer with 1% DMSO). $A_0$=the absorbance at 420 nm in absence of $Hg^{2+}$.
Figure 22:
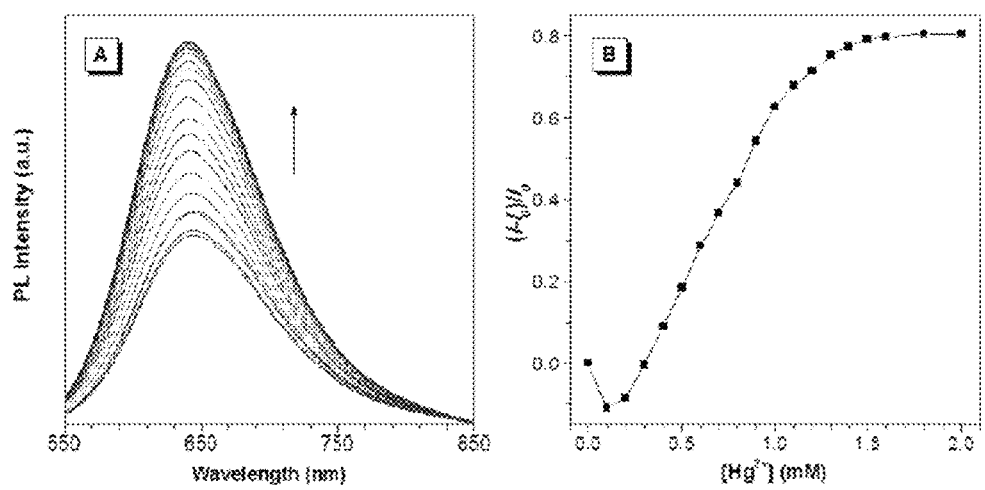
FIG. 22a shows the change of photoluminescence spectra of TPEBe-$ClO_4$ in the aqueous buffer (pH 7.4, 20 mM HEPES buffer with 1% DMSO) in the presence of different concentrations of $Hg^{2+}$ (0-2.0 mM).
FIG. 22b a plot of $(I-I_0)/I_0$ value versus concentration of $Hg^{2+}$ in aqueous buffer (pH 7.4, 20 mM HEPES buffer with 1% DMSO). $I_0$=the emission intensity at 640 nm in absence of $Hg^{2+}$. Solution concentration: 20 µM; excitation wavelength: 480 nm.

In another embodiment, TPEBe-$ClO_4$ can also be used as a fluorescent sensor for $Hg^{2+}$. As shown in FIGS. 21 and 22, the addition of $Hg^{2+}$ into the aqueous solution of TPEBe-$ClO_4$ generated a similar change in the UV-vis spectra as compared to that of TPEBe-I. Therefore, aggregation of TPEBe-$ClO_4$ increased because of the addition of $Hg^{2+}$. Accordingly, due to the aggregation-induced emission of the TPEBe-$ClO_4$ luminogen, the emission intensity of TPEBe-$ClO_4$ also increased upon the addition of $Hg^{2+}$. The results shown in FIGS. 21 and 22 indicate that the cationic unit for both TPEBe-I and TPEBe-$ClO_4$ luminogens is the same, which includes an S atom in the benzothiazolium unit. $Hg^{2+}$ is a well-known thiophilic metal ion and interacts preferentially with S atoms, which are soft bases in view of Pearson's hard-soft acid-base theory. So, in addition to interacting with iodine ions in TPEBe-I, $Hg^{2+}$ also interacts with the S atom in the benzothiazolium unit. The solubility of the resultant coordination complex becomes poorer, and therefore, more aggregation is formed in aqueous solution.

Figure 23:
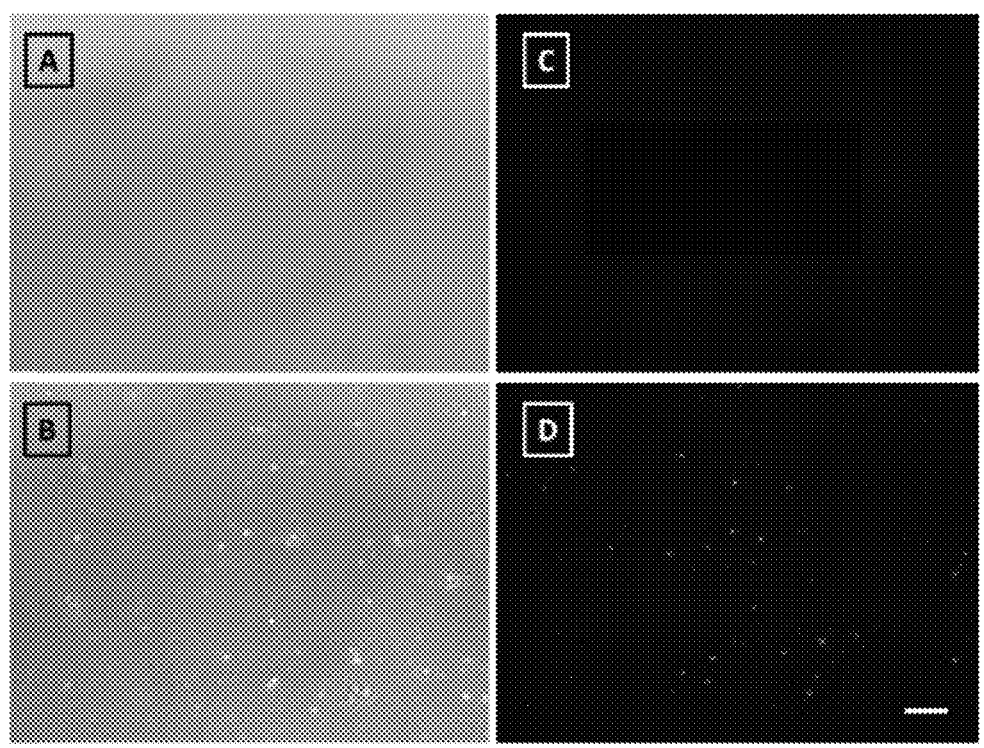
FIG. 23a shows bright field images of TPEBe-I (20.0 µM) in the absence of $Hg^{2+}$; the scale bar represents 10 µm.
FIG. 23b shows bright field images of TPEBe-I (20.0 µM) after addition of $Hg^{2+}$ (2.0 mM); the scale bar represents 10 µm.
FIG. 23c shows fluorescent images of TPEBe-I (20.0 µM) in the absence of $Hg^{2+}$; the scale bar represents 10 µm.
FIG. 23d shows fluorescent images of TPEBe-$ClO_4$ (20.0 µM) after addition of $Hg^{2+}$ (2.0 mM); the scale bar represents 10 µm.
Figure 24:
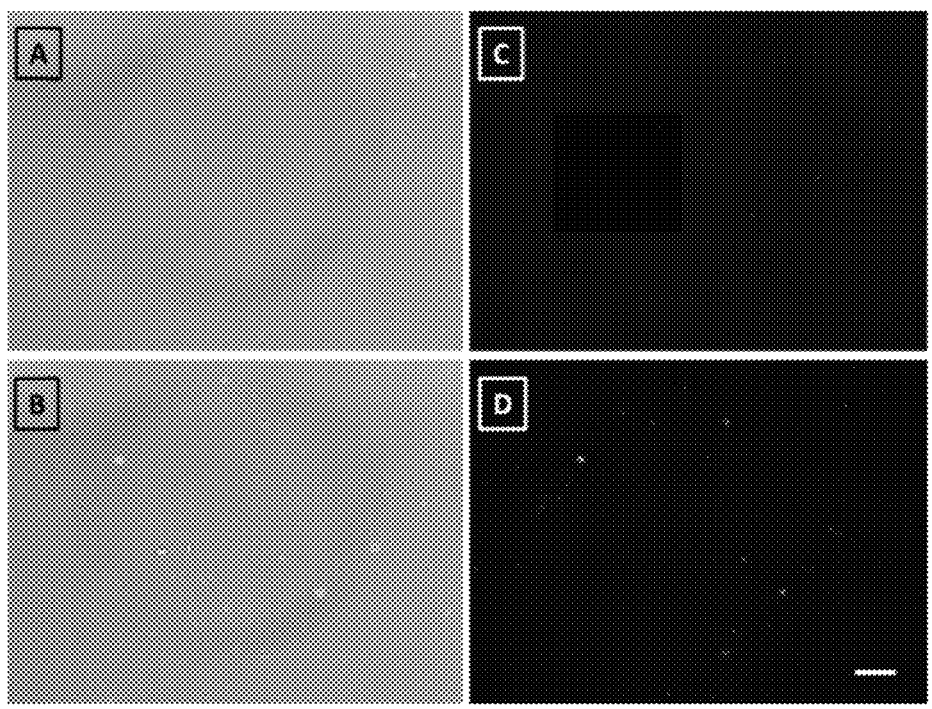
FIG. 24a shows bright field images of TPEBe-$ClO_4$ (20.0 µM) in the absence of $Hg^{2+}$; the scale bar represents 10 µm.
FIG. 24b shows bright field images of TPEBe-$ClO_4$ (20.0 µM) after addition of $Hg^{2+}$ (2.0 mM); the scale bar represents 10 µm.
FIG. 24c shows fluorescent images of TPEBe-$ClO_4$ (20.0 µM) in the absence of $Hg^{2+}$; the scale bar represents 10 µm.
FIG. 24d shows fluorescent images of TPEBe-$ClO_4$ (20.0 µM) after addition of $Hg^{2+}$ (2.0 mM); the scale bar represents 10 µm.

FIGS. 23 and 24 show the effect of $Hg^{2+}$ on the emission of both TPEBe-I and TPEBe-$ClO_4$. FIGS. 23a and 23c show pure TPEBe-I in aqueous solution in the absence of $Hg^{2+}$. As shown, only tiny particles, which are nearly non-emissive under the UV light, can be seen. In contrast, FIGS. 23b and 23d show TPEBe-I in aqueous solution in the presence of $Hg^{2+}$ (2.0 mM). As shown, many larger particles, which emit bright red under the UV light, can be seen. TPEBe-$ClO_4$ exhibits similar phenomena (FIG. 24). FIGS. 24a and 24c show pure TPEBe-$ClO_4$ in aqueous solution in the absence of $Hg^{2+}$, where only tiny particles, which are nearly non-emissive under the UV light, can be seen. In contrast, FIGS. 24b and 24d show TPEBe-$ClO_4$ in aqueous solution in the presence of $Hg^{2+}$ (2.0 mM), where many larger particles, which emit bright red under the UV light, can be seen. Therefore, $Hg^{2+}$ yields more aggregation of both TPEBe-I and TPEBe-$ClO_4$, which induces higher emission intensities thereof. Accordingly, the present subject matter relates to the use of a fluorescent sensor for the detection of $Hg^{2+}$ comprising one or more of TPEBe-I and/or TPEBe-$ClO_4$.

Figure 25:
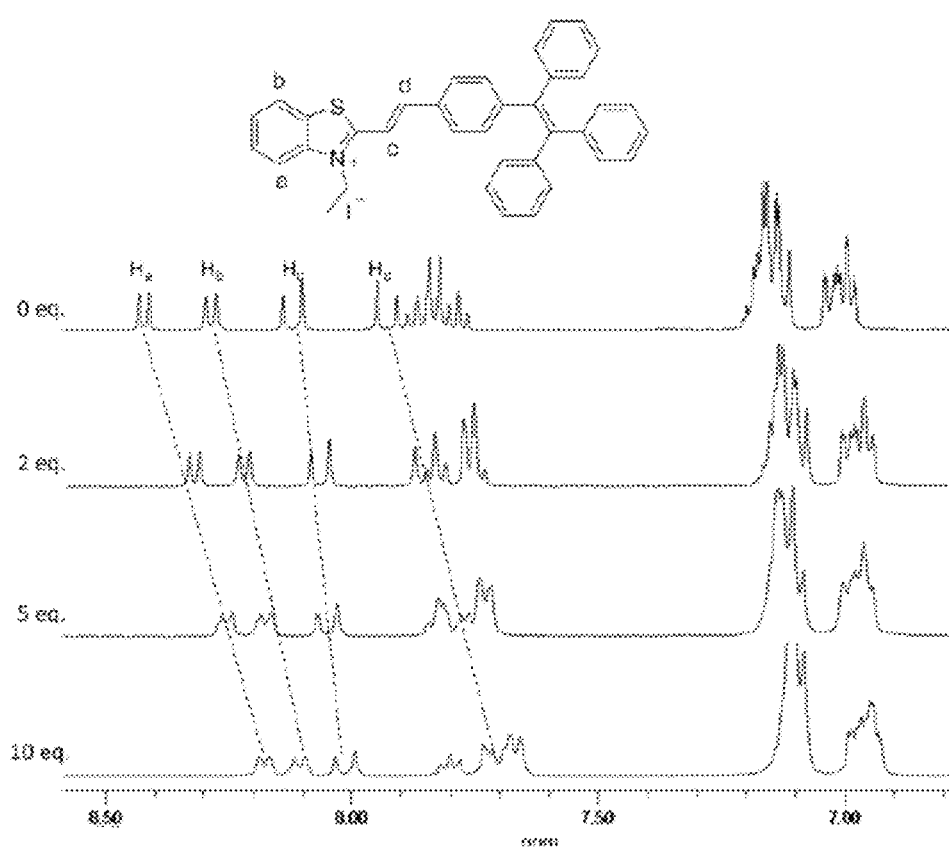
FIG. 25 shows a partial $^1$H NMR spectra of TPEBe-I and TPEBe-I with different concentration of $HgCl_2$ in $D_2O$/DMSO-$d_6$.

FIG. 25 shows partial $^1HNMR$ spectra of TPEBe-I at different concentrations of $HgCl_2$ in $D_2O/DMSO$-$d_6$. After treatment with $Hg^{2+}$ from 0 equiv. to 10 equiv., all the characteristic aromatic signals of TPEBe-I in low areas corresponding to protons (Ha, Hb, Hc, Hd) near the S atom were prominently shifted upfield by about 0.2 ppm. This appearance is distinctly caused by the reduced shielding effect of the thiazole ring ascribed to the formation of a complex between the TPEBe cationic unit and $Hg^{2+}$. Accordingly, $Hg^{2+}$ does interact with the S atom of the benzothiazolium unit of the TPEBe-I luminogen.

Figure 26:
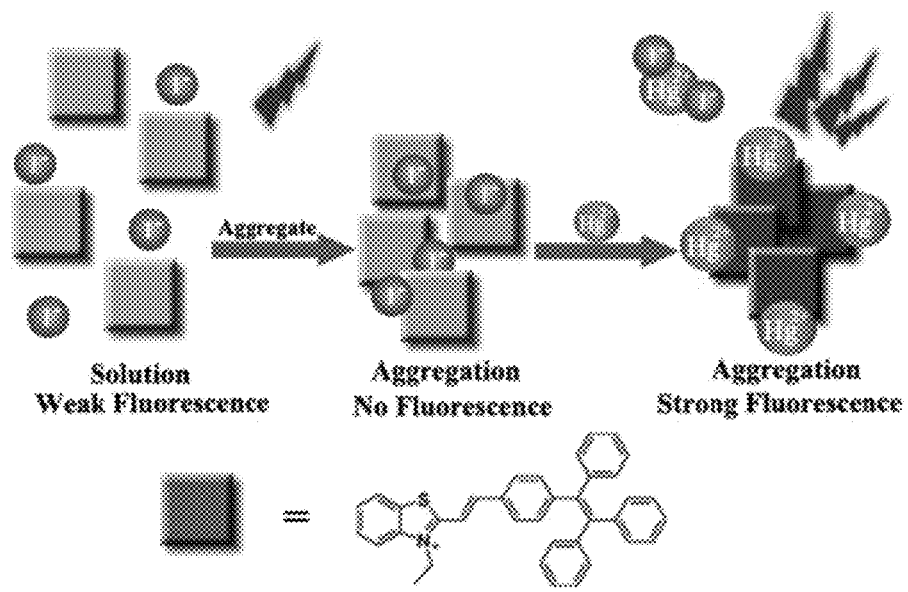
FIG. 26 shows a schematic illustration of the mechanism for detecting $Hg^{2+}$.

Accordingly, FIG. 26 shows a schematic illustration of the mechanism for detecting $Hg^{2+}$ using the TPEBe-I luminogen as a fluorescent sensor. TPEBe-I shows weak fluorescence in a solution due to the partial rotation of TPE unit. However, upon the addition of a large amount of water, TPEBe-I aggregates due to its highly hydrophobic nature. In the aggregate state, the iodine ion causes quenching because of the formation of close contact ion pairs in the aggregate state, resulting in TPEBe-I being non-emissive. However, the addition of $Hg^{2+}$ eliminates the quenching effect caused by the iodine ion due to the formation of $HgI_2$. Moreover, the addition of $Hg^{2+}$ can induce a more drastic aggregation of the remaining luminogen in the aqueous solution through the coordination of the S atom with the benzothiazolium unit. Therefore, the present subject matter is directed to using the TPEBe-I luminogen as an "off-on" fluorescent sensor for $Hg^{2+}$. In addition, the TPEBe-I luminogen can be used as a solid-state fluorescent probe for the detection of $Hg^{2+}$.

Figure 51:
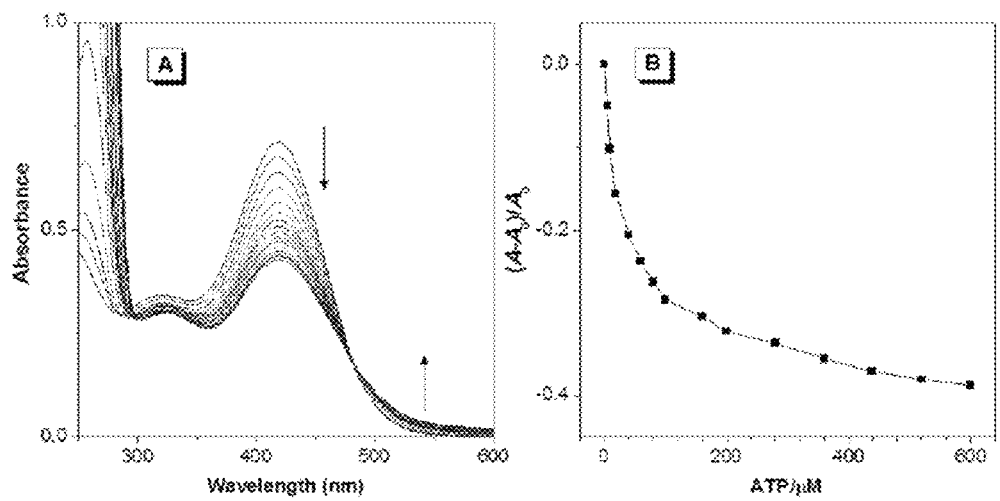

In another embodiment, the present subject matter relates to the use of TPEBe-I as a fluorescent sensor for ATP. As shown in FIG. 51, upon addition of ATP into the aqueous solution of TPEBe-I, the lowest energy absorption peak at 420 nm decreases gradually. In addition, there is a slight red shift with increasing of concentration of ATP. The presence of well-defined points at about 480 nm indicates that only two species coexisted in the equilibrium. Notably, the absorption tails appear in the long wavelength region after the addition of ATP. This implies that more aggregation is formed based on the Mie effect of particles.

Figure 52:
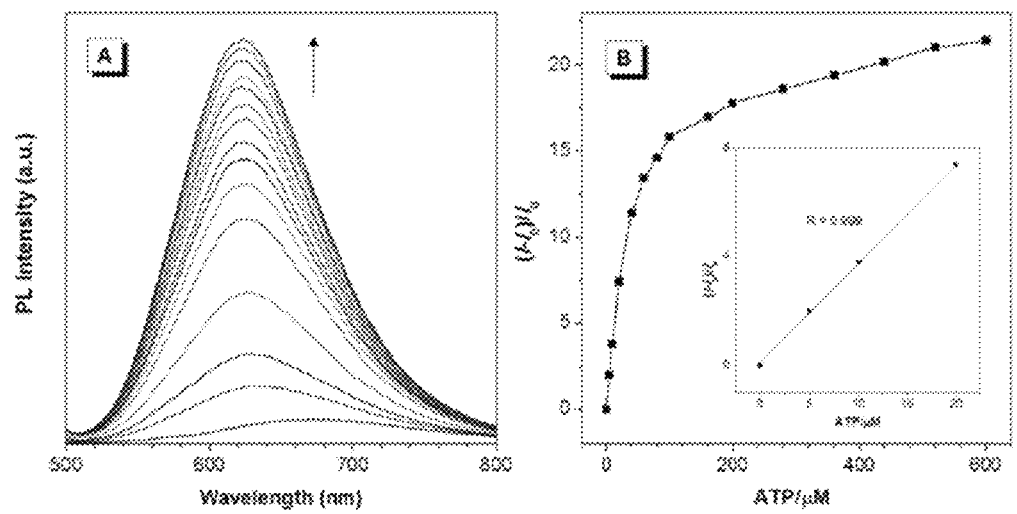

As shown in FIG. 52, the emission intensity of TPEBe-I increases upon the addition of ATP when it is photoexcited at the isobestic point (480 nm). When the concentration of ATP is 600 μM, the emission intensity of TPEBe-I increases 20-fold. Moreover, the emission color also changes from dark into bright red under 365 nm UV illumination (FIG. 53b). This indicates that TPEBe-I can act as "off-on" sensor for ATP in aqueous solutions. Obviously, the value of $(I-I_0)/I_0$ has a linear relationship with ATP from 0 to 20 μM.

Figure 53:
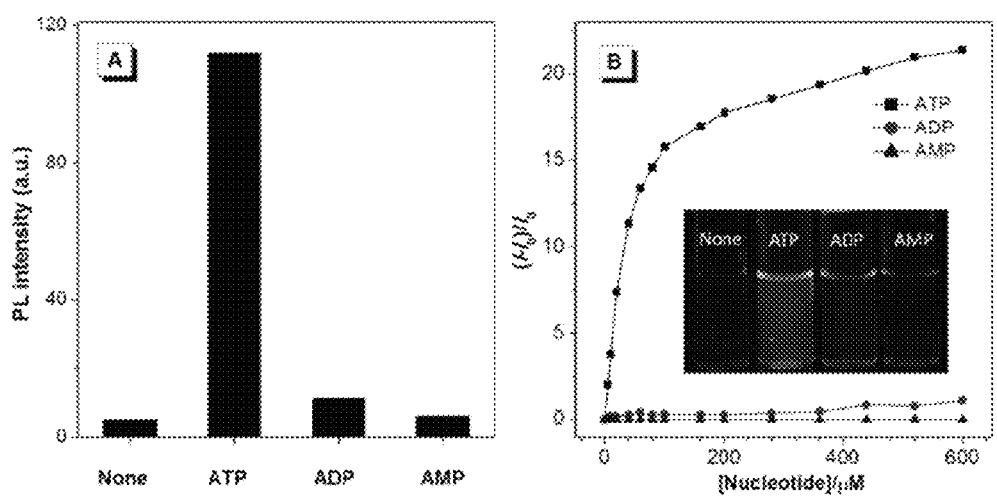

FIG. 53 demonstrates the selectivity and sensitivity of TPEBe-I as a fluorescent sensor for detecting ATP over other nucleotides. The fluorescence response of TPEBe-I was carried out using ATP, ADP and AMP. As depicted in FIG. 53, only ATP induced remarkable emission enhancement, whereas ADP and AMP led to negligible changes for the emission of TPEBe-I. The results confirm that TPEBe-I shows excellent selectivity towards the ATP over other competitive nucleotides, which clarifies that TPEBe-I possesses high sensitivity and selectivity towards ATP in aqueous solution. Accordingly, one embodiment relates to the use of TPEBe-I as a highly sensitive and selective fluorescent sensor for ATP.

Figure 54:
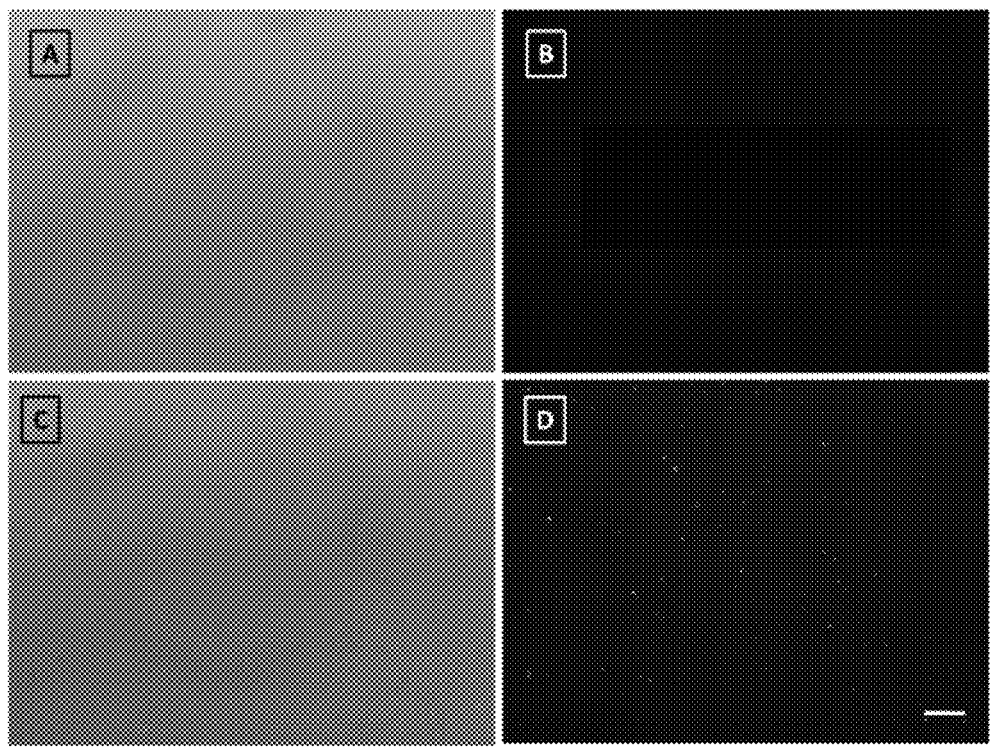

FIG. 54 demonstrates that the increased aggregation of TPEBe-I luminogens is caused by addition of ATP. Fluorescence images of luminogens in the absence and presence of ATP were tested by a fluorescence microscope. As shown in FIG. 54, pure TPEBe-I in an aqueous solution shows tiny particles, which are nearly non-emissive under the UV light. But in the presence of ATP (600 μM), several larger particles, which emit bright red under the UV light, can be seen. Therefore, the addition of ATP clearly causes increased aggregation of TPEBe-I.

In another embodiment, the present subject matter relates to the TPEPy-$PF_6$, the chemical structure of which is shown below.

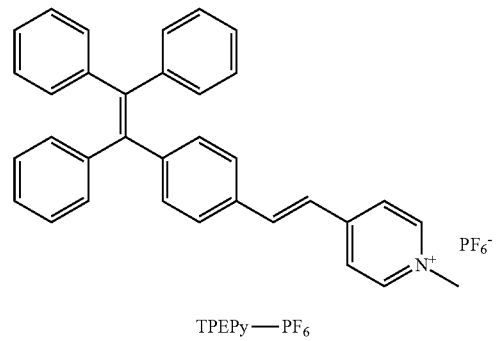

TPEPy—$PF_6$

The TPEPy-$PF_6$ luminogen is formed through simple multistep reactions shown in the reaction scheme below.

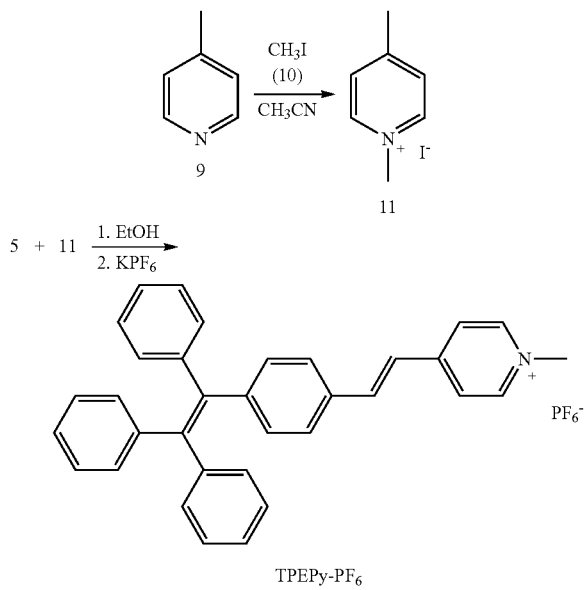

TPEPy-$PF_6$

Figure 27:
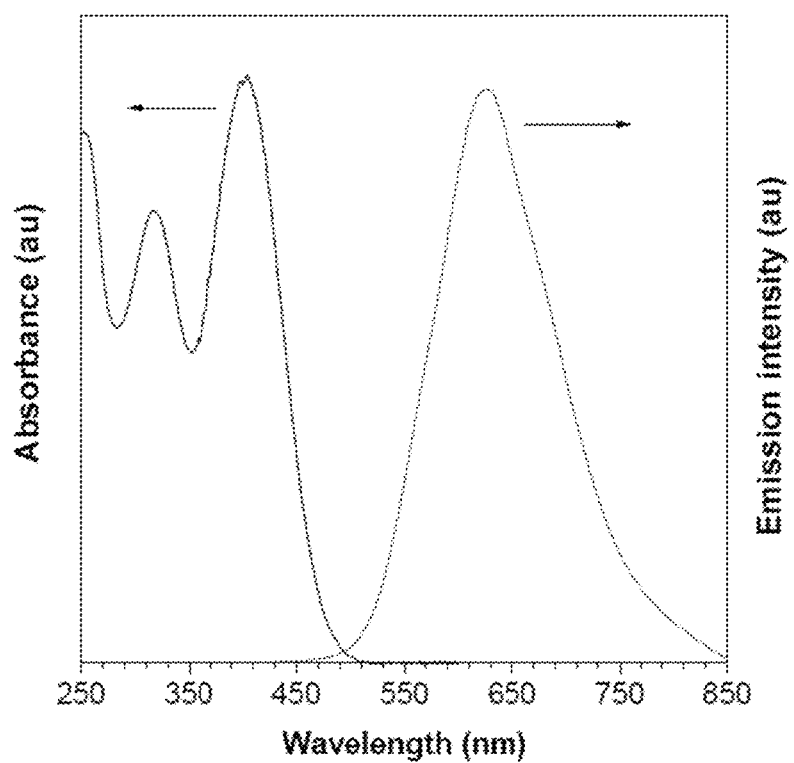
FIG. 27 shows absorption and emission spectra of TPEPy-PF6 in THF solutions.

FIG. 27 shows the UV spectrum of TPEPy-$PF_6$ in a diluted THF solution (20 uM), The lowest energy absorption band is located at about 386 nm, which is mainly attributable to the intramolecular charge transfer (ICT) from the electron-donating TPE unit to the electron-accepting pyridinium unit. In addition, TPEPy-$PF_6$ emits weakly red light peaking at 625 nm. Furthermore, the TPEPy-$PF_6$ luminogen possesses a large Stoke shift of about 222 nm, which can avoid the interference from self-absorption.

Figure 28:
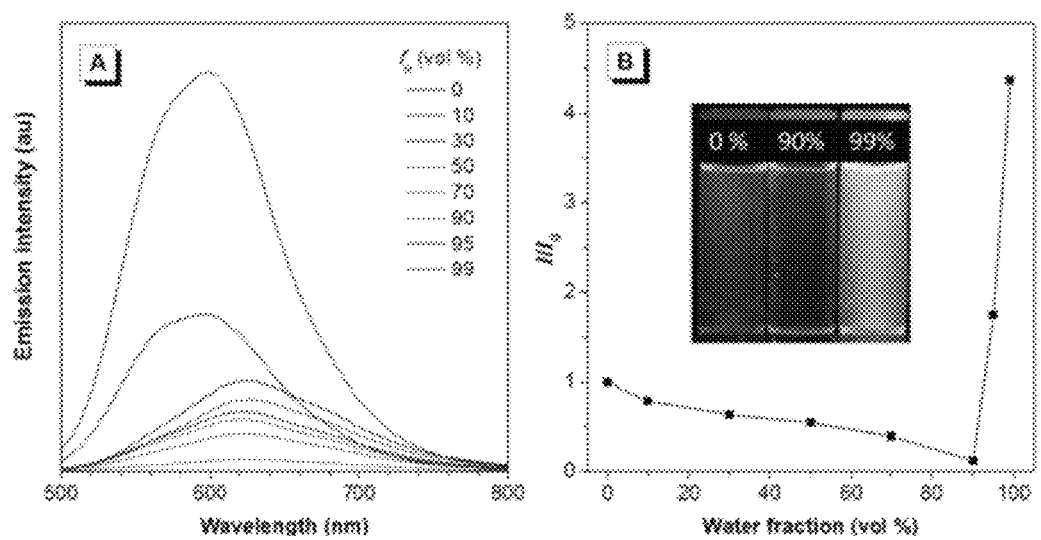
FIG. 28a shows a photoluminescence spectra of TPEPy-$PF_6$ in THF/water mixtures with different water fractions ($f_w$).
FIG. 28b shows a plot of $(I/I_0)$ value versus the compositions of the aqueous mixtures of TPEPy-$PF_6$. $I_0$=PL intensity in pure THF solution. Inset: Photographs of TPEPy-$PF_6$ in THF/Water mixtures with $f_w$ values of 0, 90 and 99% taken under 365 nm UV irradiation. Solution concentration: 20 µM; excitation wavelength: 386 nm.

FIG. 28 demonstrates the AIE of the TPEPy-$PF_6$ luminogen. Since TPEPy-$PF_6$ is not soluble in water, water was added to the THF solution of the TPEPy-$PF_6$ luminogen. As show in FIG. 28, when a small amount of water is added into the THF solution, the emission intensity decreases gradually, which is mainly due to the ICT effect. However, when the water fraction is greater than 90%, the emission intensity increases. At 99% water content, the emission intensity is more than 6-fold higher than that in pure THF solution. Moreover, the emission wavelength is blue-shifted about 25 nm as compared to that in pure THF solution. Water is a poor solvent for luminogen TPEPy-$PF_6$. Therefore, TPEPy-$PF_6$ aggregates in aqueous mixtures with high water content. When aggregated, the restriction of intramolecular rotation (RIR) is activated and the radiative decay channel of the excitons becomes populated, leading to the enhancement of emission intensity. The polarity inside the aggregate is lower than the medium outside due to the tight packing of hydrophobic molecules. This gives rise to the blue shifted emission in the aggregate state as compared to that in pure THF solution.

Figure 29:
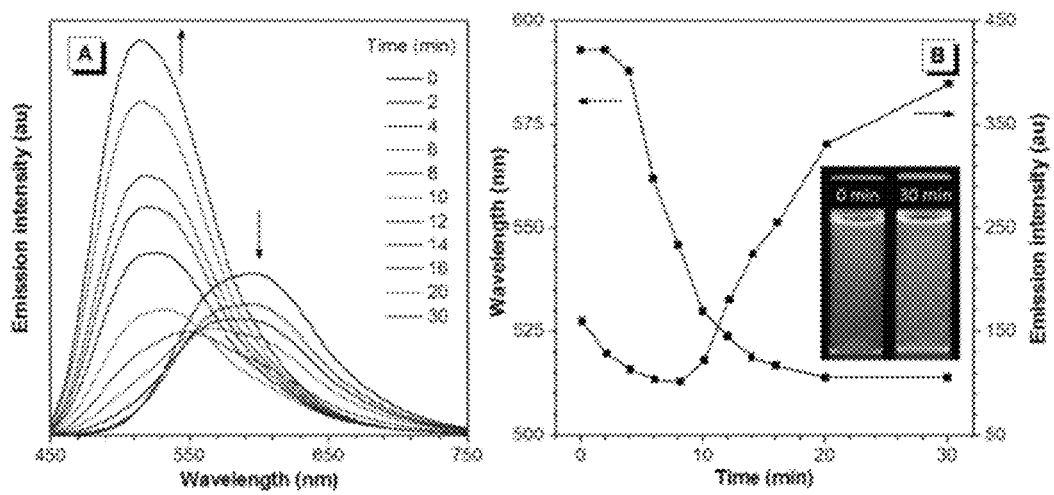
FIG. 29a shows a change in the photoluminescence spectra of TPEPy-$PF_6$ in 95% aqueous mixtures with standing time at room temperature.
FIG. 29b shows a plot of wavelength and photoluminescence intensity values versus the standing time from 0 to 30 min. Inset: photographs of TPEPy-$PF_6$ in 95% aqueous mixture at different time intervals (0 and 30 min) taken under 365 nm UV illuminations. Solution concentration: 20 µM; excitation wavelength: 386 nm.

FIG. 29 shows the emission intensity and color of a 95% aqueous mixture of TPEPy-$PF_6$ when standing at room temperature. From 0 to 30 min., the initial emission peak at 600 nm in 95% aqueous mixture decreases, and a new peak appears at 512 nm with greatly increased emission intensity. After standing about 30 min, the peak at 600 nm completely disappears and the emission spectrum is dominated by the emission peaked at 512 nm. At the same time, the emission color is completely changed from yellow to green under UV irradiation as depicted in the inset of FIG. 29.

Figure 31:
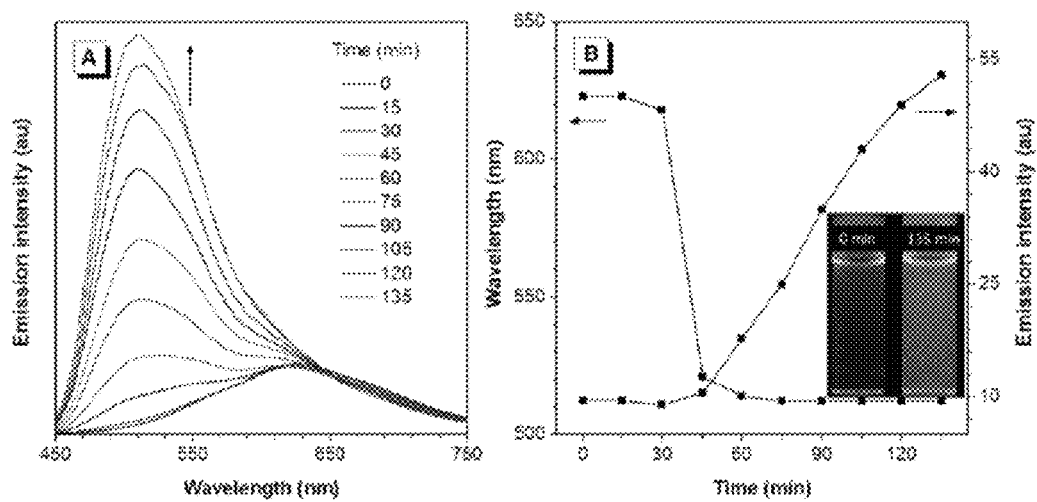
FIG. 31a shows the change in the photoluminescence spectra of TPEPy-$PF_6$ in 90% aqueous mixture with standing time at room temperature.
FIG. 31b shows a plot of the wavelength and photoluminescence intensity values versus the standing time from 0 to 135 min. Inset: Photographs of TPEPy-$PF_6$ in 90% aqueous mixture at different time intervals (0 and 135 min) taken under 365 nm UV illuminations. Solution concentration: 20 µM; excitation wavelength: 386 nm.

A similar change is seen with the 90% aqueous mixture of TPEPy-$PF_6$ (FIG. 31). Only the time (135 min.) for equilibrium and emission intensity is different for the 90% aqueous mixture of TPEPy-$PF_6$. These changes in emission for the 90% and 95% aqueous mixtures of TPEPy-$PF_6$ are caused by the crystallization process.

Figure 30:
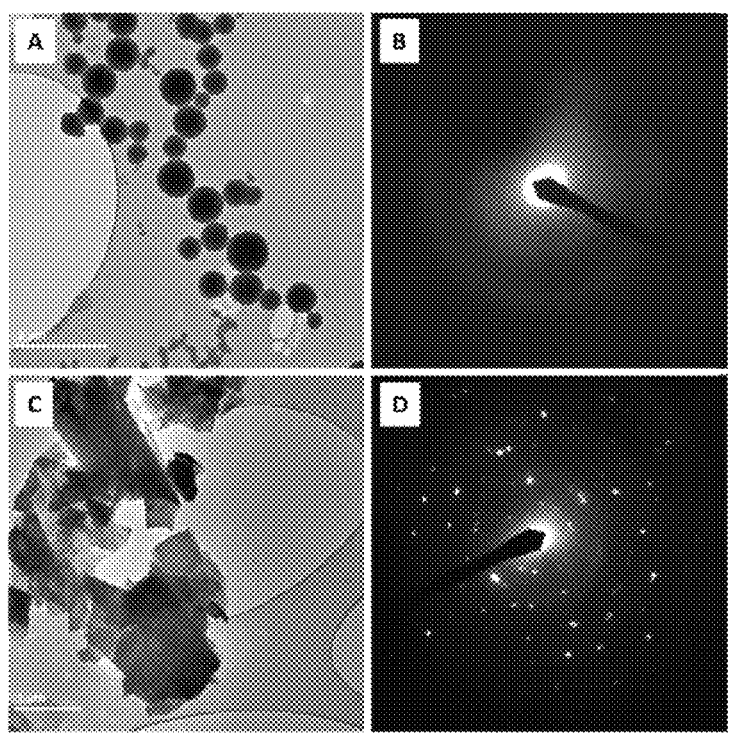
FIG. 30a shows a TEM image of amorphous aggregates of TPEPy-$PF_6$ formed in 95% aqueous mixture before the solution stood at room temperature for 30 min.
FIG. 30b shows an ED pattern of amorphous aggregates of TPEPy-$PF_6$ formed in 95% aqueous mixture after the solution stood at room temperature for 30 min.
FIG. 30c shows a TEM image of crystalline aggregates of TPEPy-$PF_6$ formed in 95% aqueous mixture before the solution stood at room temperature for 30 min.
FIG. 30d shows an ED pattern of crystalline aggregates of TPEPy-$PF_6$ formed in 95% aqueous mixture after the solution stood at room temperature for 30 min.

FIG. 30a shows a TEM image of freshly prepared 95% aqueous mixture of TPEPy-$PF_6$, wherein distinct spherical nanoparticles can be observed. As shown in FIG. 30b, there are nearly no diffraction points for those nanoparticles. This suggests that the strong yellow emission in the 95% aqueous mixture is attributed to the formation of abundant amorphous nanoaggregates. However, as shown in FIG. 30c, after standing at room temperature for 30 min, the 95% aqueous mixture of TPEPy-$PF_6$ has a flaky pattern and looks entirely different. In addition, FIG. 30d shows clear electronic diffraction points which are characteristic of the crystalline state. Therefore, the crystallization process leads to the change of emission in the 95% aqueous mixture.

Figure 32:
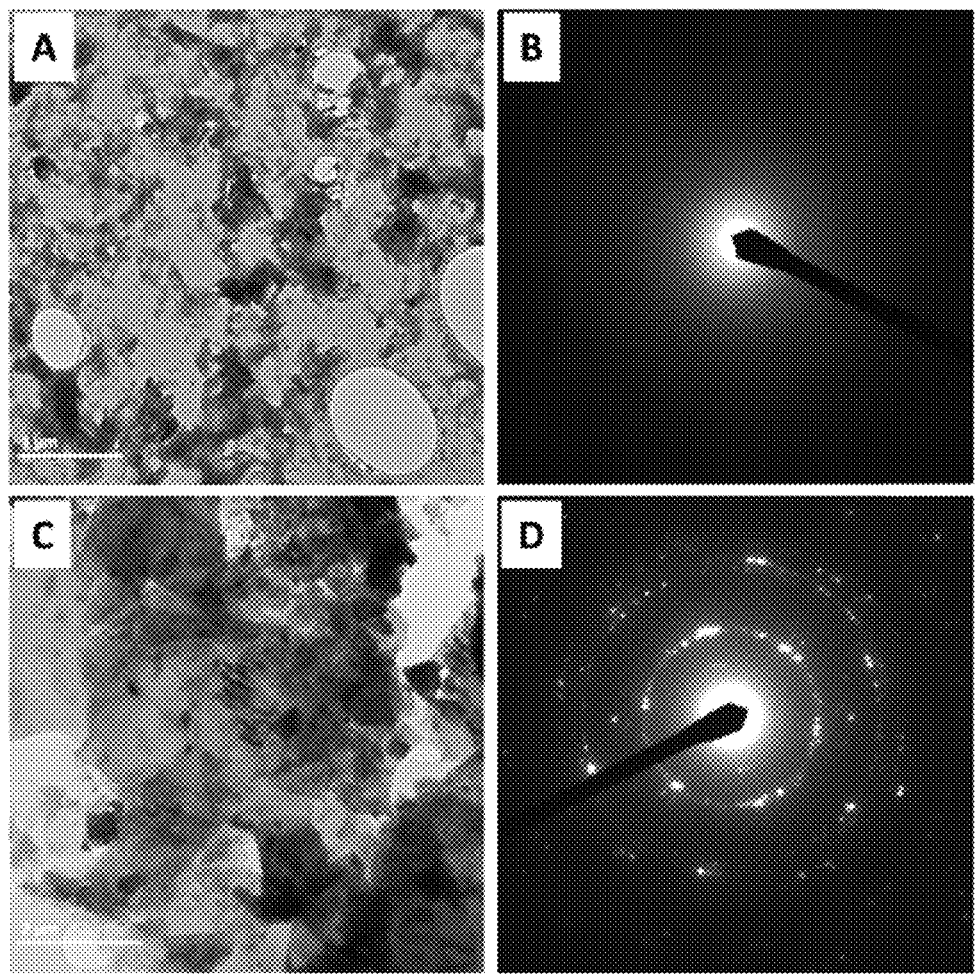
FIG. 32a shows a TEM image of amorphous aggregates of TPEPy-$PF_6$ formed in 90% aqueous mixture before the solution stood at room temperature for 135 min.
FIG. 32b shows an ED pattern of amorphous aggregates of TPEPy-$PF_6$ formed in 90% aqueous mixture after the solution stood at room temperature for 135 min.
FIG. 32c shows a TEM image of crystalline aggregates of TPEPy-$PF_6$ formed in 90% aqueous mixture before the solution stood at room temperature for 135 min.
FIG. 32d shows an ED pattern of crystalline aggregates of TPEPy-$PF_6$ formed in 90% aqueous mixture after the solution stood at room temperature for 135 min.

The TEM image of freshly prepared 90% aqueous mixture of TPEPy-$PF_6$ shows an amorphous pattern rather than nano-aggregates (FIG. 32a), which results in very weak emission in the 90% aqueous mixture. Likewise, the ED pattern also shows no signal of electronic diffraction points (FIG. 32b). However, after standing for 135 min, the TEM image of the 90% aqueous mixture of TPEPy-$PF_6$ looks flaky (FIG. 32c) and is similar to that of the 95% aqueous mixture after 30 minutes (FIG. 30c). Likewise, the ED pattern of the 90% aqueous mixture after standing for 135 minutes shows clear electronic diffraction points which are characteristic of the crystalline state (FIG. 32d). This suggests that the crystallization process also occurs in the 90% aqueous solution. Moreover, other water fraction mixtures, including 99%, do not exhibit this phenomenon.

Therefore, the 95% aqueous mixture provides a more suitable microenvironment for the molecules to reorient and pack in a more ordered fashion. The blue-shift observed in the crystalline state is mainly due to the conformation twisting of the whole TPEPy-$PF_6$ molecule in order to fit into the crystalline lattice, which is in line with that reported in AIE molecules.

Figure 33:
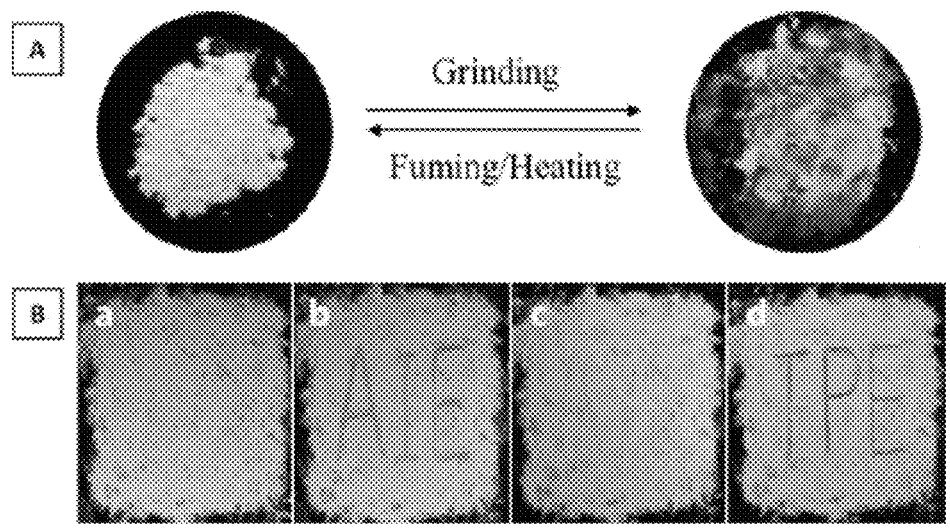
FIG. 33a shows switching the solid-state emission of TPEPy-$PF_6$ by grinding-fuming/heating process.
FIG. 33b shows fluorescent images of TPEPy-$PF_6$ (a) adsorbed in the filter paper, (b) after writing "AIE" using a metal spatula, (c) background emission restored by fuming the film with acetone vapour for 10 min, and (d) rewritable mechanochromic fluorescence demonstrated by the "TPE" generated with a metal spatula. The photographs were taken under 365 nm UV irradiation.
Figure 34:
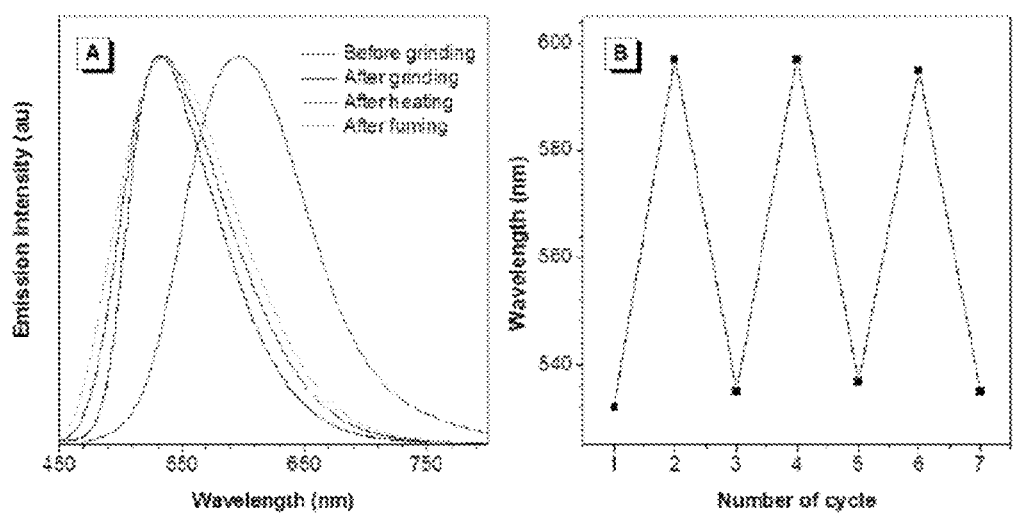
FIG. 34a shows the change in the photoluminescence spectra of TPEPy-$PF_6$ by grinding-fuming/heating process.
FIG. 34b shows repeated switching of the solid-state fluorescence of TPEPy-$PF_6$ by repeated grinding and fuming/heating cycles.

In another embodiment, the TPEPy-$PF_6$ luminogens exhibit mechanochromic luminescence. The microcrystals of TPEPy-$PF_6$ are easily formed through slow evaporation from a DCM/hexane mixture, which shows a strong green emission peak at about 515 nm. After gentle grinding using a pestle and a mortar, a yellow emission powder is formed with an emission peak at 600 nm. After fuming with acetone vapor for 10 min or heating at 150° C. for 10 min, the initial green emission color reappears (FIGS. 33 and 34). The conversion between green and orange emission colors as well as their corresponding photoluminescence spectra can be repeated many times without fatigue because these external stimuli are nondestructive to the nature of the molecule.

In FIG. 33b, crystalline powders were smeared on a slice of filter paper as a thin film. Under the 365 nm UV irradiation, the filter paper exhibits green color. After writing the letters "AIE" using a metal spatula on the filter paper, the letters "AIE" emitted the yellow color (FIG. 33b). Fuming with the acetone vapour erases the letters by converting the emission into the background emission. When the letters of "TPE" are written again, distinct yellow color for the letters can be detected. The results demonstrate the TPEPy-$PF_6$ luminogen can serve as a recyclable optical storage media. Accordingly, one embodiment of the present subject matter is directed to the use of the TPEPy-$PF_6$ luminogen as a recyclable optical storage media.

Figure 35:
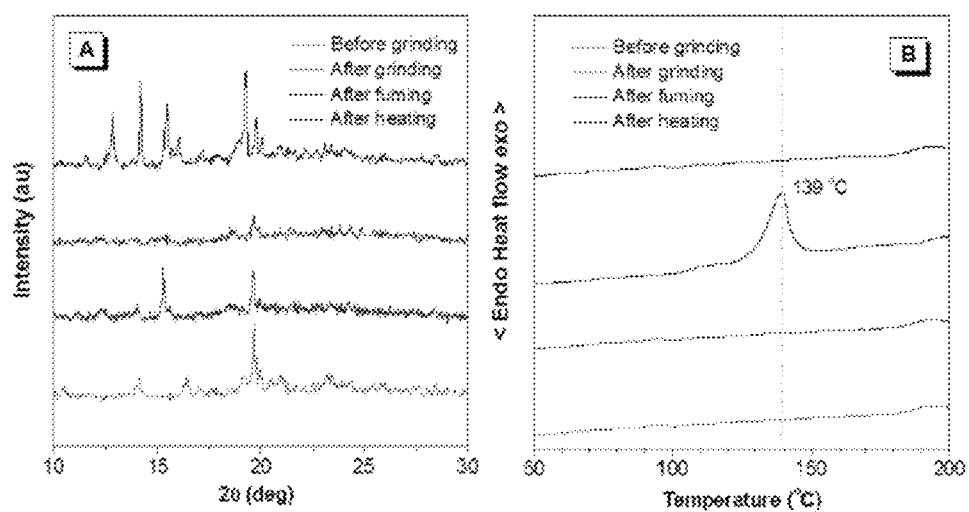
FIG. 35a shows XRD diffractograms of TPEPy-$PF_6$ at different aggregated phases recorded at a heating rate of 10° C./min.
FIG. 35b shows DSC thermograms of TPEPy-$PF_6$ at different aggregated phases recorded at a heating rate of 10° C./min.

In FIG. 35a, the powder XRD of the different aggregated states of the TPEPy-$PF_6$ luminogen were analyzed. Before grinding, the crystalline sample show many sharp diffraction peaks, indicative of its well-ordered crystalline nature (FIG. 35a). After grinding, nearly no peaks can be observed for its diffractogram, suggesting it is amorphous. When the ground powders are treated by heating or fuming with solvent vapor, similar profiles of the diffractogram with sharp diffraction peaks appear again. However, they are not much different from that of an unground sample, which means that the thermal and fuming treatment can return the amorphous state of the TPEPy-$PF_6$ TPEPy-$PF_6$ luminogen into the crystalline state.

FIG. 35b shows analysis via DSC of the different aggregation states of the TPEPy-$PF_6$ luminogen. During the only heating scan, only the ground sample shows an endothermic peak at 139° C., which is caused by the recrystallization process, because the decomposition temperature of TPEPy-$PF_6$ is more than 200° C., as indicated by the TGA analysis. No signals were detected in the unground sample or the thermal, fume treated samples, as they are in the crystalline state. Due to the propeller shape of TPE, the packing of the TPEPy-$PF_6$ molecule is relatively loose in the crystalline state, which can be easily destroyed in response to external force. Meanwhile, the destroyed packing can be recovered into a stable state through a recrystallization process via the thermal or fume treatment. Therefore, the mechanochromism property observed in TPEPy-$PF_6$ is associated with the morphology change between the crystalline and the amorphous states.

Figure 36:
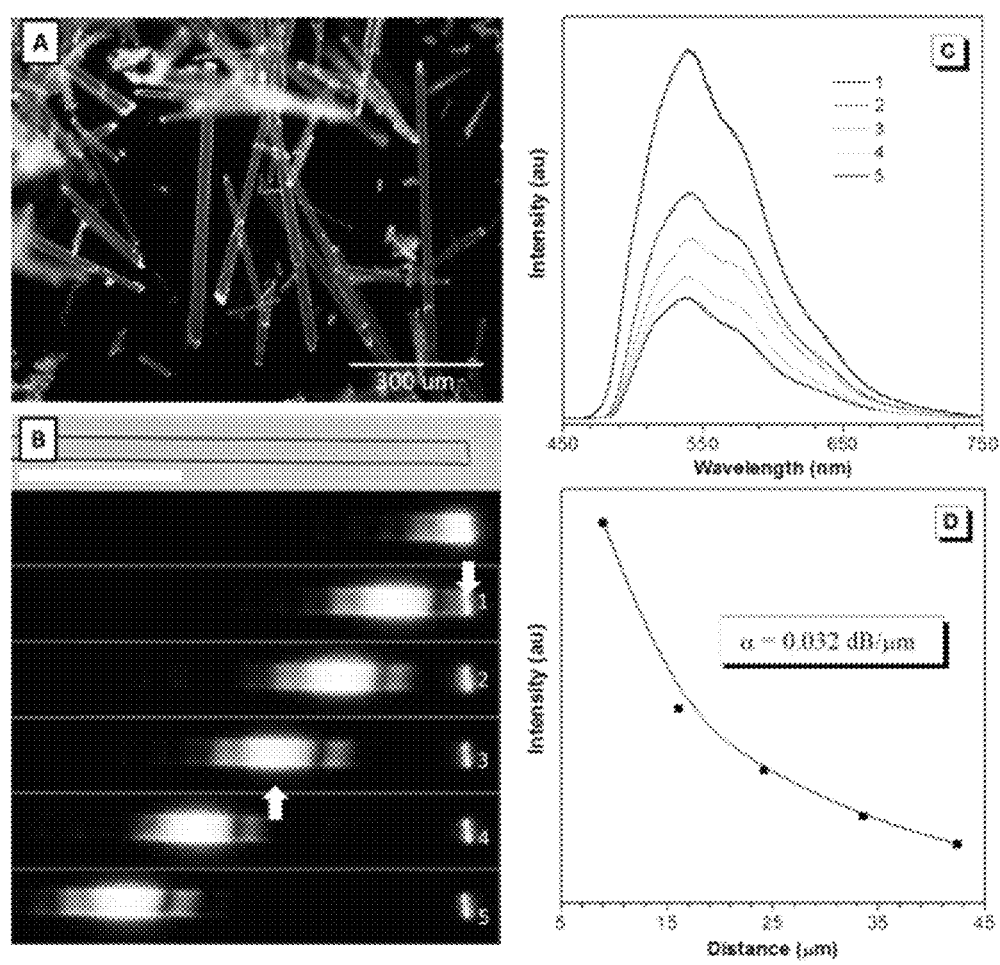
FIG. 36a shows a fluorescent image of crystalline microrods of TPEPy-$PF_6$ taken under UV irradiation on a fluorescence microscope.
FIG. 36b shows Microarea photoluminescence images obtained by exciting an identical microrod at different positions, up arrow (excited site) and down arrow (emitted tip). Scale bar is 20 µm.
FIG. 36c shows the corresponding photoluminescence spectra to the Microarea photoluminescence images in FIG. 36b.
FIG. 36d shows a plot of photoluminescence intensity value versus distance.

In one embodiment, the crystal of TPEPy-$PF_6$ exhibits an excellent optical waveguide. FIG. 36a shows a fluorescent image of crystalline microrods of TPEPy-$PF_6$ taken under UV irradiation on a fluorescence microscope. As shown in FIG. 36b, the distance-dependent photoluminescence image of a single microrod was measured through a near-field scanning optical microscope. A chosen microrod on the glass coverslip is excited with a uniform focused laser (351 nm) at five different local positions along the length of the microrods. The green emission appears at one end of the microrod in addition to the local area of the excited position (labelled with 1, 2, 3, 4 and 5). This phenomenon indicates that the microrod of TPEPy-$PF_6$ absorbs the excitation light and propagates the photoluminescence emission toward the end of the microrod. The appearance of the outcoupling light at the end of each microrod is a typical characteristic of strong waveguide behaviour. Accordingly, microrods of TPEPy-$PF_6$ can be classified as active waveguides since the waveguided light is generated from the photoluminescence. The corresponding photoluminescence spectra collect at the fixed end of a single microrod where the excitation position is varied (FIG. 36b). By increasing the distance of the excitation position, the emission intensity at the end of the microrod decreased without any red shift of emission wavelength (FIGS. 36c and 36d). This is mostly caused by the optical loss during the propagation process.

The optical loss coefficient is an important parameter (a) to determine the property of waveguide materials. The emission intensity at the fixed end (Iend) and the excited site of a microrod ($I_{body}$) are recorded. The optical loss coefficient (a) can be calculated by a single exponential fitting [$I_{end}/I_{body}$=Aexp$^{-\alpha x}$, where x is the distance between the exciting site and the emitting end, and A is the ratio of the light escaping from the excitation spot and that of the light propagating along the fiber]. Herein, α value of TPEPy-PF$_6$ is determined to be 0.032 dB/μM. This explains why the optical loss of the microrod of TPEPy-PF$_6$ is low as an organic waveguide material. A large Stokes shift of the TPEPy-PF$_6$ luminogen helps it to refrain from re-absorption, which is the main factor for optical loss in a propagation process. Moreover, the smooth surface and well-ordered arrangement in the crystalline state also contributed to this excellent optical waveguide behaviour.

Figure 37:
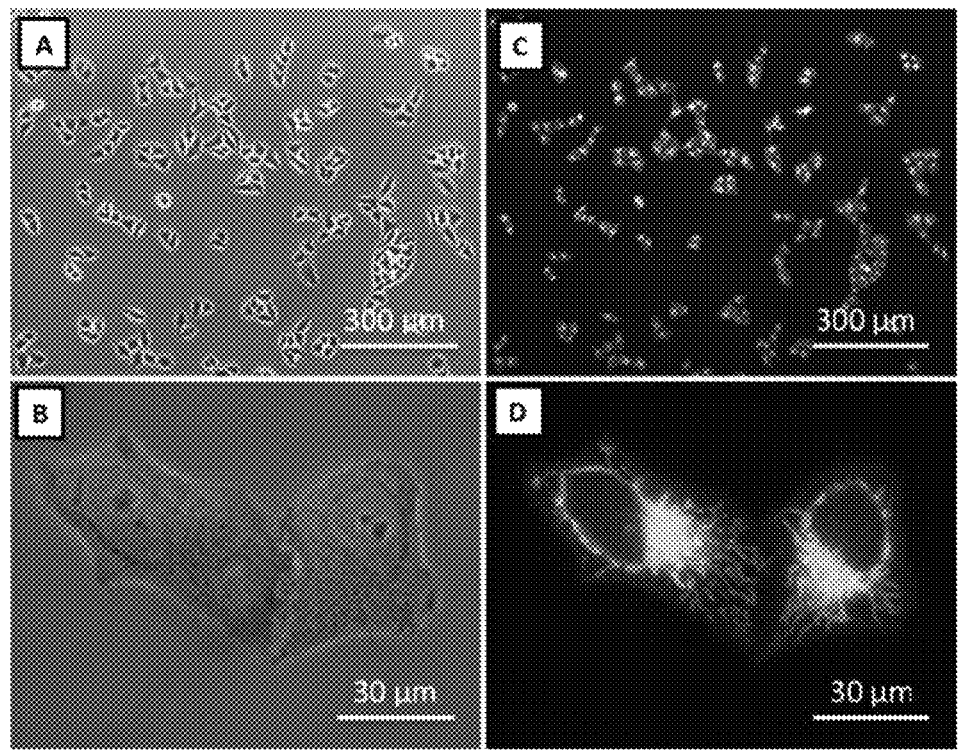
FIG. 37a shows a bright field image of HeLa cells stained by TPEPy-$PF_6$ (5 µM) for 15 min.
FIG. 37b shows a bright field image of HeLa cells stained by TPEPy-$PF_6$ (5 µM) for 15 min.
FIG. 37c shows a fluorescent image of HeLa cells stained by TPEPy-$PF_6$ (5 µM) for 15 min.
FIG. 37d shows a fluorescent image of HeLa cells stained by TPEPy-$PF_6$ (5 µM) for 15 min.

In a further embodiment, the present subject matter is directed to the use of the TPEPy-PF$_6$ luminogen as a fluorescent stain for living cell imaging. Nanoaggregates of TPEPy-PF$_6$ were prepared in minimum essential medium/DMSO mixtures and the HeLa cells were imaged using a standard cell-staining protocol. The living cells were incubated with TPEPy-PF$_6$ (5 μM) for 15 min and then washed three times with phosphate buffered saline solution. Normal morphology of the living cells even in the presence of TPEPy-PF$_6$ indicates that TPEPy-PF$_6$ shows low toxicity to living cells. As shown in FIG. 37, under the wide-field fluorescent microscope, there is a distinct yellow emission, which likely originated from the mitochondria in view of its morphological character. This demonstrates that the TPEPy-PF$_6$ luminogen can label cellular mitochondria.

Figure 38:
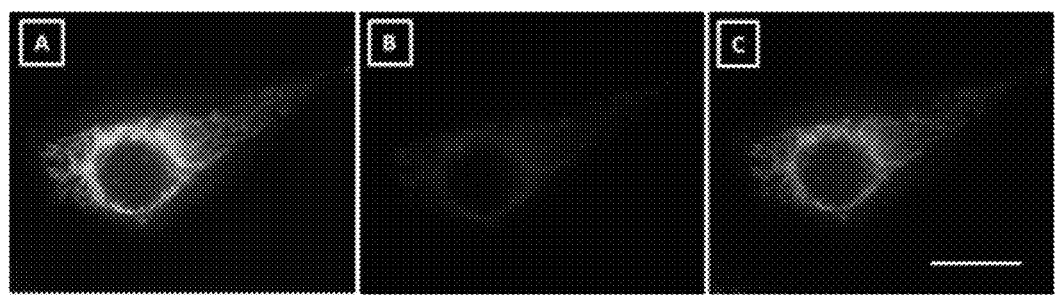
FIG. 38a shows a wide-field fluorescence image of a Hela cell incubated with TPEPy-$PF_6$ (5 µM) for 15 min.
FIG. 38b shows a wide-field fluorescence image of a Hela cell incubated with MitoTracker Red (100 nM) for 15 min.
FIG. 38c shows the merged fluorescence image picture. Scale bar is 20 μm.

Living cells were incubated with both mitochondria-targeted dye MitoTracker Red (100 nM) and TPEPy-PF$_6$ (5 μM) for 15 min at 37° C. by the above procedure. As shown in FIG. 38, the yellow and red emission channels from the cell indicate the TPEPy-PF$_6$ and MitoTracker Red, respectively. As shown in FIG. 38c, the merged fluorescence image picture exhibits orange color and reveals the position, shape, and amounts of the mitochondria stained by the TPEPy-PF$_6$ luminogen are the same as for MitoTracker Red. Therefore, one embodiment of the present subject matter relates to the use of the TPEPy-PF$_6$ luminogen to exclusively stain the mitochondria of living cells.

Figure 39:
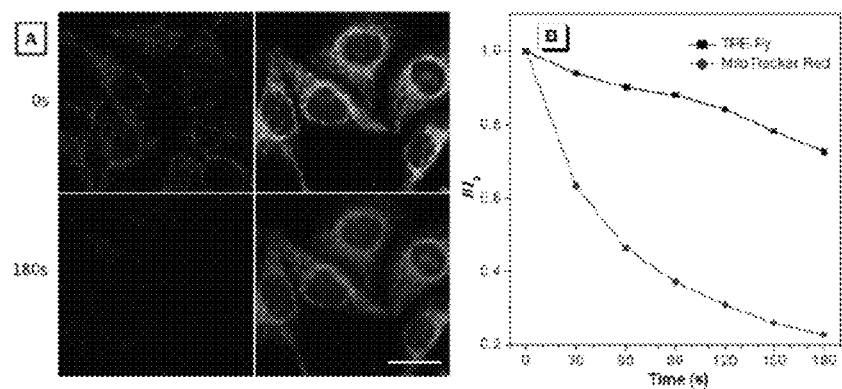
FIG. 39a shows confocal luminescence images of fixed HeLa cells stained with TPEPy-PF$_6$ and MitoTracker Red under continuous excitation at 405 nm and 560 nm with 0.6 mW, respectively (0, 180 s). Scale bar is 20 μm.
FIG. 39b shows luminescence decay curves of TPEPy-PF$_6$ and MitoTracker Red during the same period.

As shown in FIG. 39, after continuous excitation using a laser at 588 nm (0.6 mW) for 180 seconds, the emission of the MitoTracker Red in living cells nearly disappears in the fluorescent image. However, the emission intensity is decreased to about 20% of its initial value due to photobleaching (FIG. 39b). In contrast, during the same power period of excitation (405 nm, 0.6 mW), the emission in the fluorescent image of living cells incubated with TPEPy-PF$_6$ is still clear. In addition, the luminescence intensity of TPEPy-PF$_6$ is maintained at essentially 70% of its original intensity. This clearly establishes that the TPEPy-PF$_6$ luminogen shows reduced photobleaching and higher photostability than MitoTracker Red in living cells.

Mitochondria possess large membrane potential with a net negative charge on the matrix side of the membrane. Thus, mitochondria-targeted fluorescent dyes should be lipophilic and cationic. In view of this, the lipophilic nature and positive charge of the TPEPy-PF$_6$ luminogen makes the TPEPy-PF$_6$ luminogen excellent for staining mitochondria.

Another embodiment of the present subject matter relates to the N$_3$-PyTPE luminogen, the chemical structure of which is shown below.

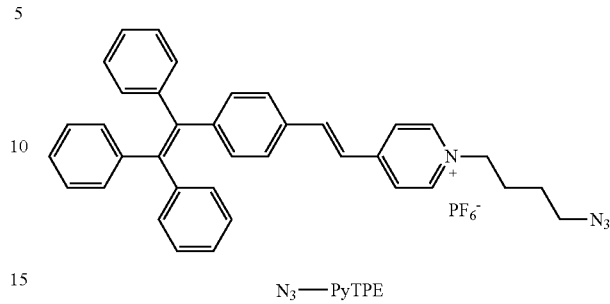

The N$_3$-PyTPE luminogen was synthesized in four steps via the reactions shown in the below reaction scheme.

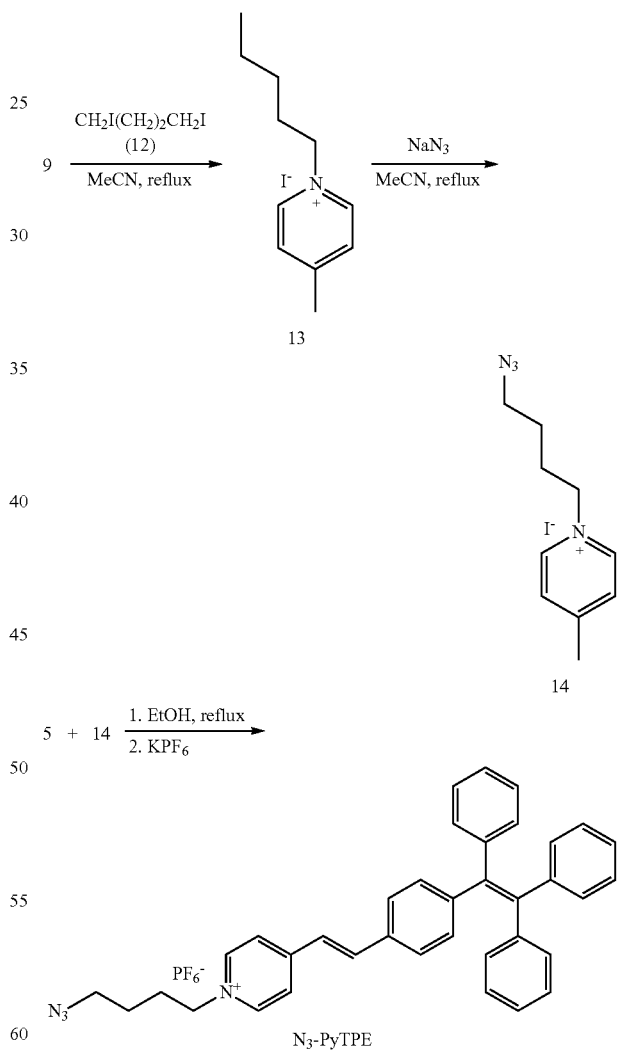

Figure 40:
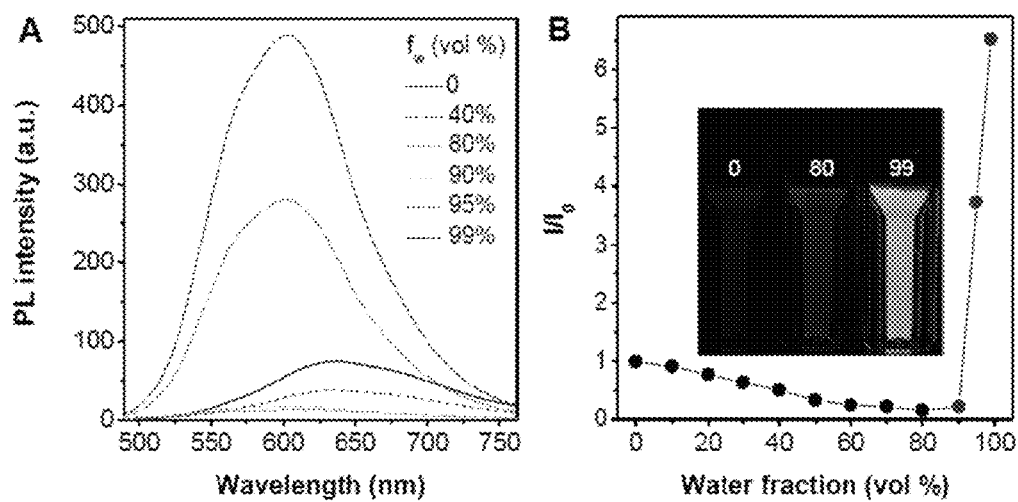
FIG. 40a shows a photoluminescence spectra of N$_3$-PyTPE in DMSO/water mixtures with different water fractions ($f_w$).
FIG. 40b shows a plot of ($N_0$) values versus the compositions of the aqueous mixtures. $I_0$=emission intensity in pure DMSO solution. [N$_3$-PyTPE]=10 μM; $\lambda_{ex}$=405 nm. Inset: Photographs of N$_3$-PyTPE in DMSO/water mixtures with $f_w$ values of 0, 80 and 99% aqueous mixtures taken under 365 nm UV illumination.

As shown in FIG. 40, the N$_3$-PyTPE luminogen absorbs at 405 nm in diluted DMSO solution, and shows weak red emission at 636 nm when the solution of N$_3$-PyTPE is excited under a UV lamp. The emission intensity decreases as the amount of water is increased, due to the intramolecular charge transfer (ICT) effect from the electron-donating TPE unit to the electron-accepting pyridinium unit. However, when the fraction of water ($f_w$) is more than 80%, the emission intensity begins to increase with an increasing water content. $N_3$-PyTPE emits strong orange fluorescence as nanoaggregates in a mixture of DMSO/$H_2O$ (1:99 by vol) (FIG. 40b). The aggregate formation was confirmed by laser light scattering (LLS) measurements. In the aqueous mixture, the hydrophobic $N_3$-PyTPE molecules cluster into aggregates with an average diameter of 42.1 nm (FIG. 41b). Clearly, the $N_3$-PyTPE luminogen is AIE-active.

In another embodiment, the present subject matter relates to the Ac-DEVD-PyTPE probe, which was synthesized via the reaction shown in the reaction scheme below. Specifically, the Ac-DEVD-PyTPE probe was synthesized by a copper catalyzed "click" reaction of $N_3$-PyTPE and an alkyne-functionalized DEVD peptide in a DMSO/water mixture.

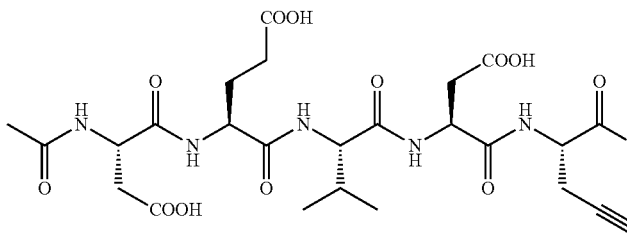

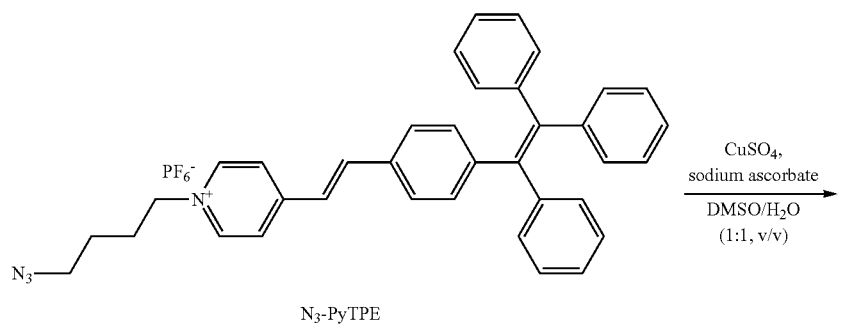

N₃-PyTPE

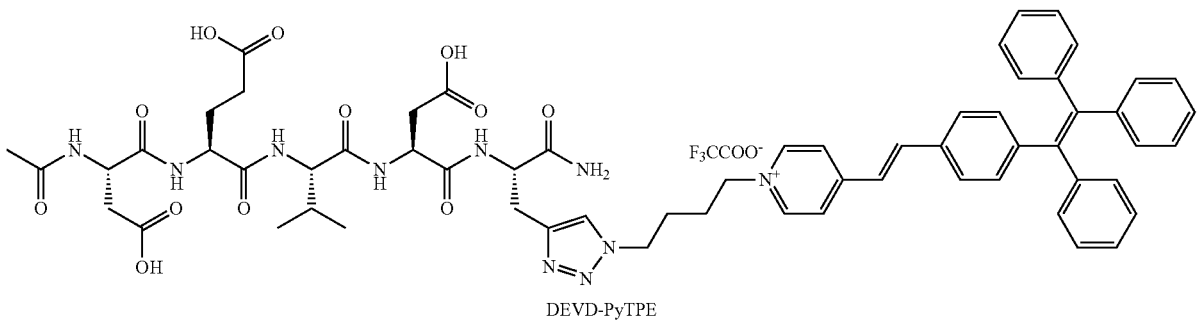

DEVD-PyTPE

Figure 41:
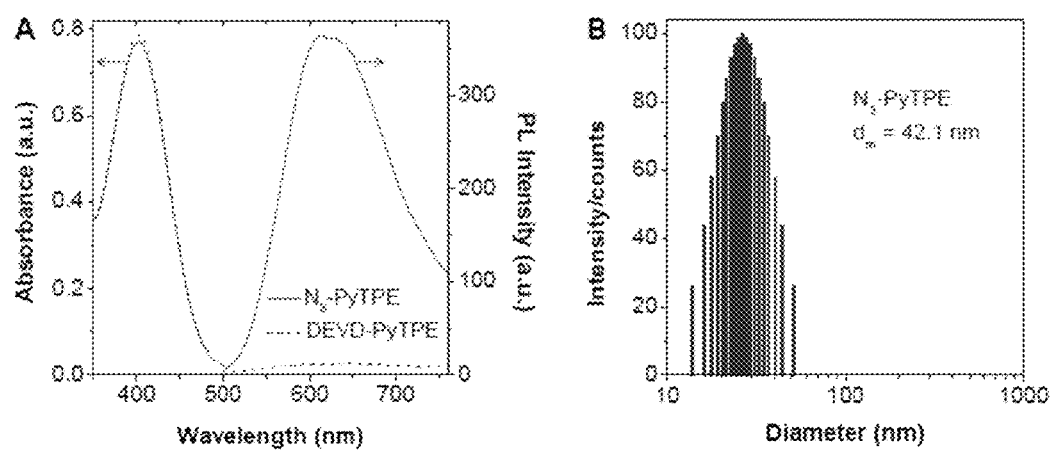
FIG. 41a shows the UV-vis absorption and photoluminescence spectra of N$_3$-PyTPE (red, solid) and Ac-DEVD-PyTPE (blue, dash) in DMSO/water (v/v=1/199). [N$_3$-PyTPE]=[Ac-DEVD-PyTPE]=10 μM. $\lambda_{ex}$=405 nm.
FIG. 41b shows the hydrodynamic diameters of N$_3$-PyTPE in DMSO/water (v/v=1/199).

FIG. 41 shows the optical properties of Ac-DEVD-PyTPE. Ac-DEVD-PyTPE shows similar absorption spectral profiles as those of N₃-PyTPE. N₃-PyTPE emits strong fluorescence in aqueous solution, whereas Ac-DEVD-PyTPE does not fluoresce in the same buffer due to its good solubility in water.

In one embodiment, the present subject matter relates to the use of Ac-DEVD-PyTPE as a probe for caspase activity. Specifically, the present subject matter relates to the use of Ac-DEVD-PyTPE as a probe for caspase-3 and caspase-7. In another embodiment, the present subject matter relates to the use of the Ac-DEVD-PyTPE probe for live-cell imaging of caspase-3 activation. In a further embodiment, the Ac-DEVD-PyTPE probe has low cytotoxicity in living cells.

Figure 42:
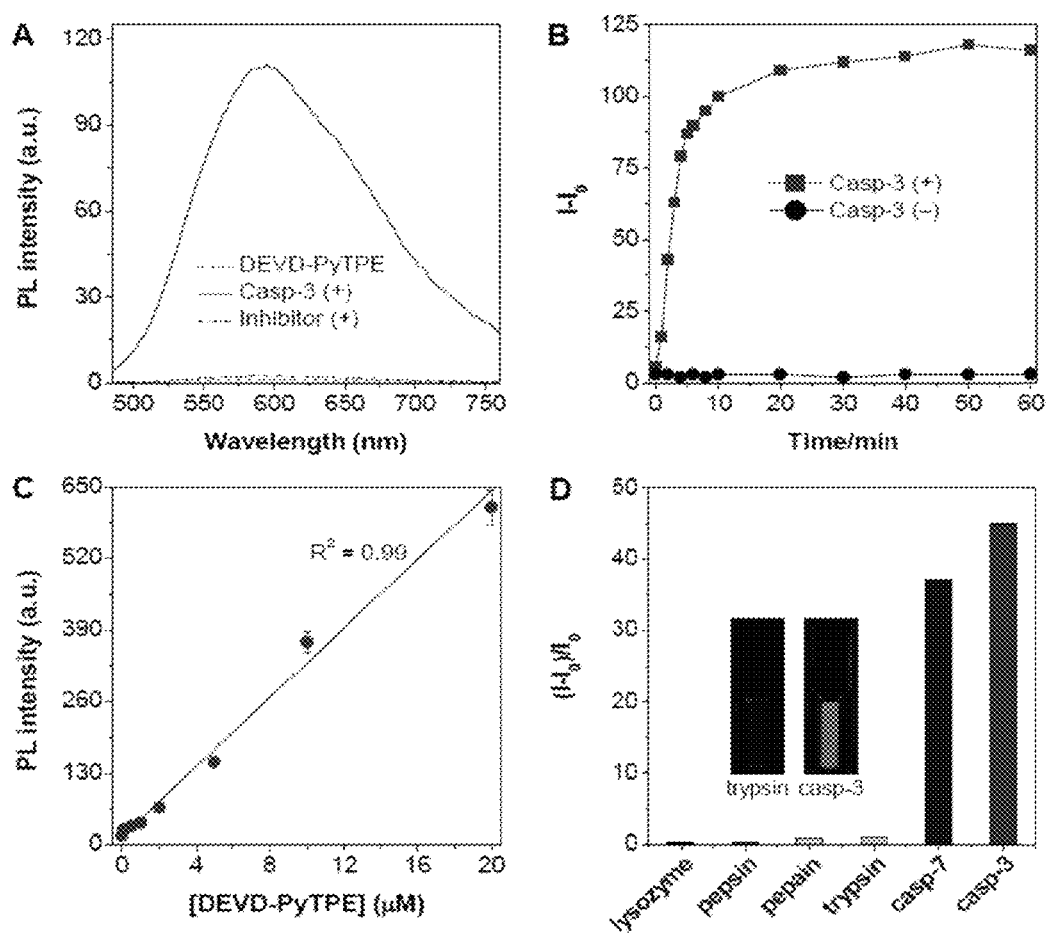
FIG. 42a shows the photoluminescence spectra of Ac-DEVD-PyTPE treated with caspase-3 in the presence and absence of inhibitor MPS (10 μM) in PIPES buffer.
FIG. 42b shows a plot of I–$I_0$ versus time of Ac-DEVD-PyTPE with and without treatment of caspase-3 from 0 to 60 min. [caspase-3]=5 μg mL$^{-1}$, [Ac-DEVD-PyTPE]=10 μM.
FIG. 42c shows a plot of photoluminescence intensity versus concentrations of Ac-DEVD-PyTPE in RIPES buffer. [caspase-3]=5 μg mL$^{-1}$.
FIG. 42d shows a plot of (I–$I_0$)/$I_0$ versus different proteins, where I and h are the photoluminescence intensities at protein concentrations of 20 and 0 μg mL$^{-1}$, respectively. Inset: photographs taken under UV illumination. $\lambda_{ex}$=405 nm; $\lambda_{em}$=610 nm.
Figure 43:
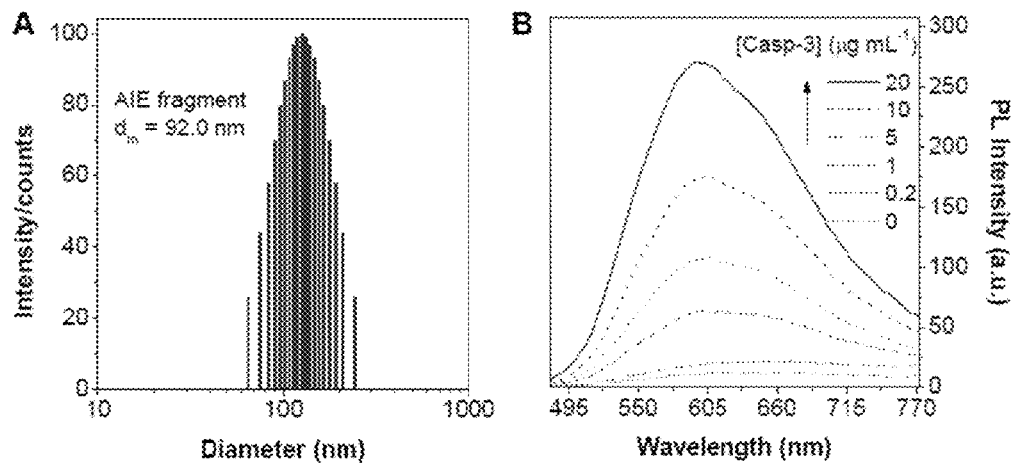
FIG. 43a shows the hydrodynamic diameters of the AIE fragment of Ac-DEVD-PyTPE after caspase-3 cleavage in PIPES buffer obtained from LLS.
FIG. 43b shows the photoluminescence spectra of Ac-DEVD-PyTPE in the presence of different amounts of caspase-3 (0, 0.2, 1, 5, 10 and 20 μg mL$^{-1}$), [Ac-DEVD-PyTPE]=10 μM, $\lambda_{ex}$=405 nm.
Figure 44:
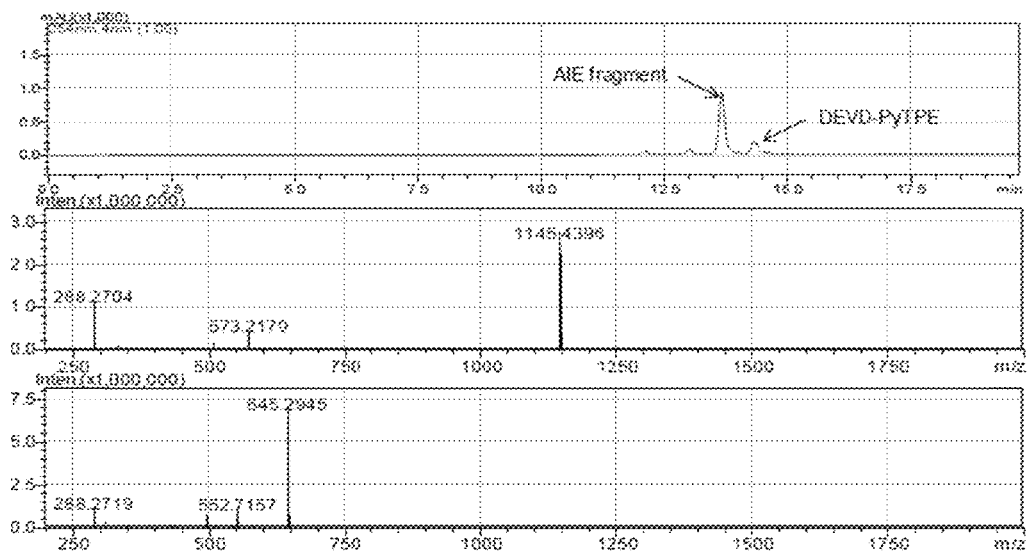
FIG. 44 shows the caspase-catalyzed hydrolysis of Ac-DEVD-PyTPE monitored by LC-MS.

As shown in FIG. 42a, strong fluorescence signals were recorded for the assay in which Ac-DEVD-PyTPE was treated with caspase-3 in PIPES buffer (50 mM PIPES, 100 mM NaCl, 1 mM ethylenediaminetetraacetic acid, 0.1% w/v 3-[(3-cholamidopropyl)dimethylammonio]propanesulfonic, 25% w/v sucrose, pH=7.2). Particles with an average diameter of 92 nm formed in addition to the increase of fluorescence in the solution (FIG. 43a). Most of the fluorescence was readily competed away when the probe was pre-treated with 5-[(S)-(+)-2-(methoxymethyl)pyrrolidino]sulfonylisatin (MPS), a highly specific inhibitor of caspase-3, indicating that specific cleavage of DEVD from Ac-DEVD-PyTPE was inhibited. This was further confirmed by LC-MS as shown in FIG. 44. The caspase-3/7 catalyzed hydrolysis of Ac-DEVD-PyTPE is shown in the reaction scheme below.

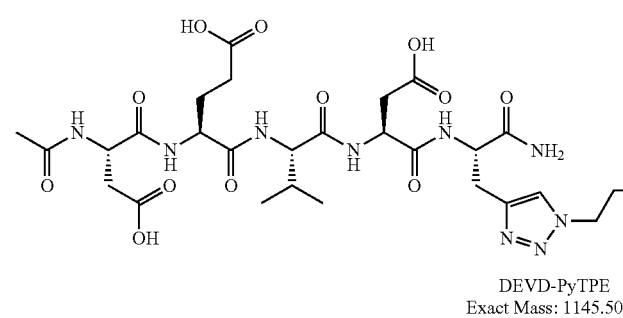

DEVD-PyTPE
Exact Mass: 1145.5091

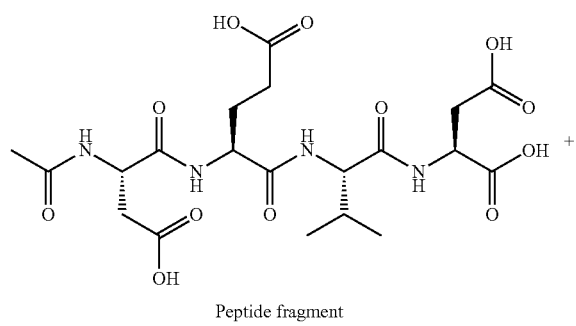

Peptide fragment

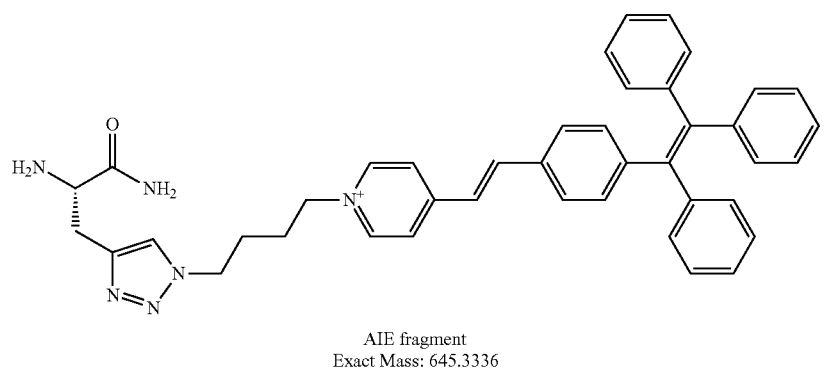

AIE fragment
Exact Mass: 645.3336

As shown in FIG. 43b, there is a significant increase in fluorescence over the background for caspase-3. In the absence of caspase-3, nearly no change in fluorescence is observed, confirming that Ac-DEVD-PyTPE is specifically recognized and cleaved by caspase-3. Additionally, when recombinant caspase-3 (5 μg mL$^{-1}$) was treated with Ac-DEVD-PyTPE at different concentrations (0-20 μM), a linear fluorescence increase at 610 nm was observed (FIG. 43c), which suggests the Ac-DEVD-PyTPE can be easily quantified based on the photoluminescence intensity changes.

FIG. 43d demonstrates the selectivity of the Ac-DEVD-PyTPE probe, which was treated with several enzymes, such as caspase-3, caspase-7, pepsin, trypsin, papain and lysozyme, under identical conditions. The fluorescence change of assays was detected using a standard spectrofluorometer and is shown in FIG. 43d. As shown, caspase-3 and caspase-7 display respectively about 43- and 36-fold higher changes in $(I-I_0)/I_0$ than the other four enzymes. This clearly indicates that Ac-DEVD-PyTPE can be used as a specific probe for caspase-3 and caspase-7.

Figure 45:
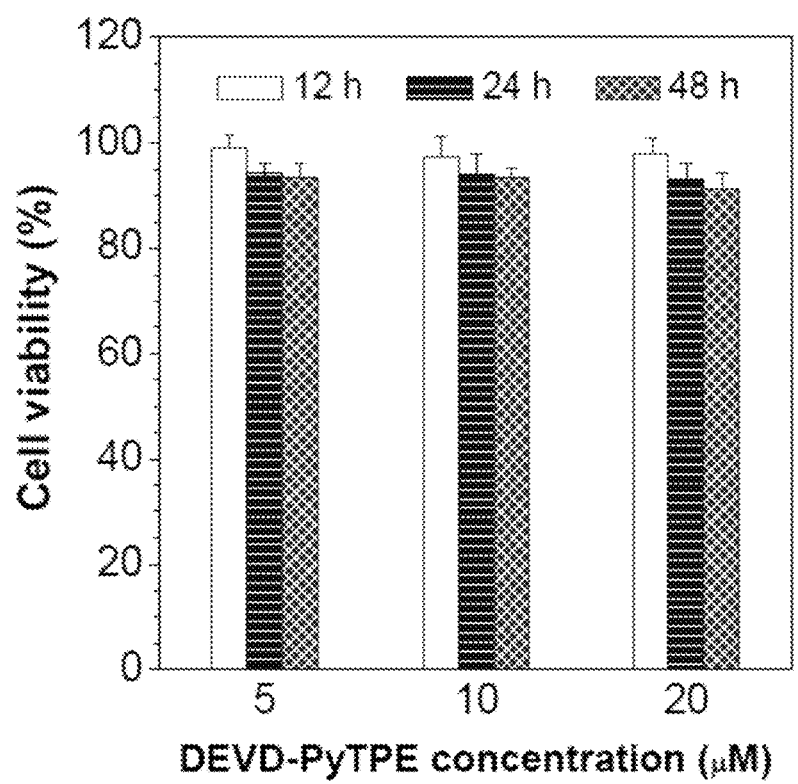
FIG. 45 shows the metabolic viability of MCF-7 cancer cells after incubation with Ac-DEVD-PyTPE at concentration of 5, 10 and 20 IM for 12, 24 and 48 h.

As shown in FIG. 45, after being incubated with Ac-DEVD-PyTPE at 5, 10, and 20 μM for 12, 24, and 48 h, the cell viabilities are close to 100% under the testing conditions. This is indicative of the low cytotoxicity of the Ac-DEVD-PyTPE probe.

Figure 46:
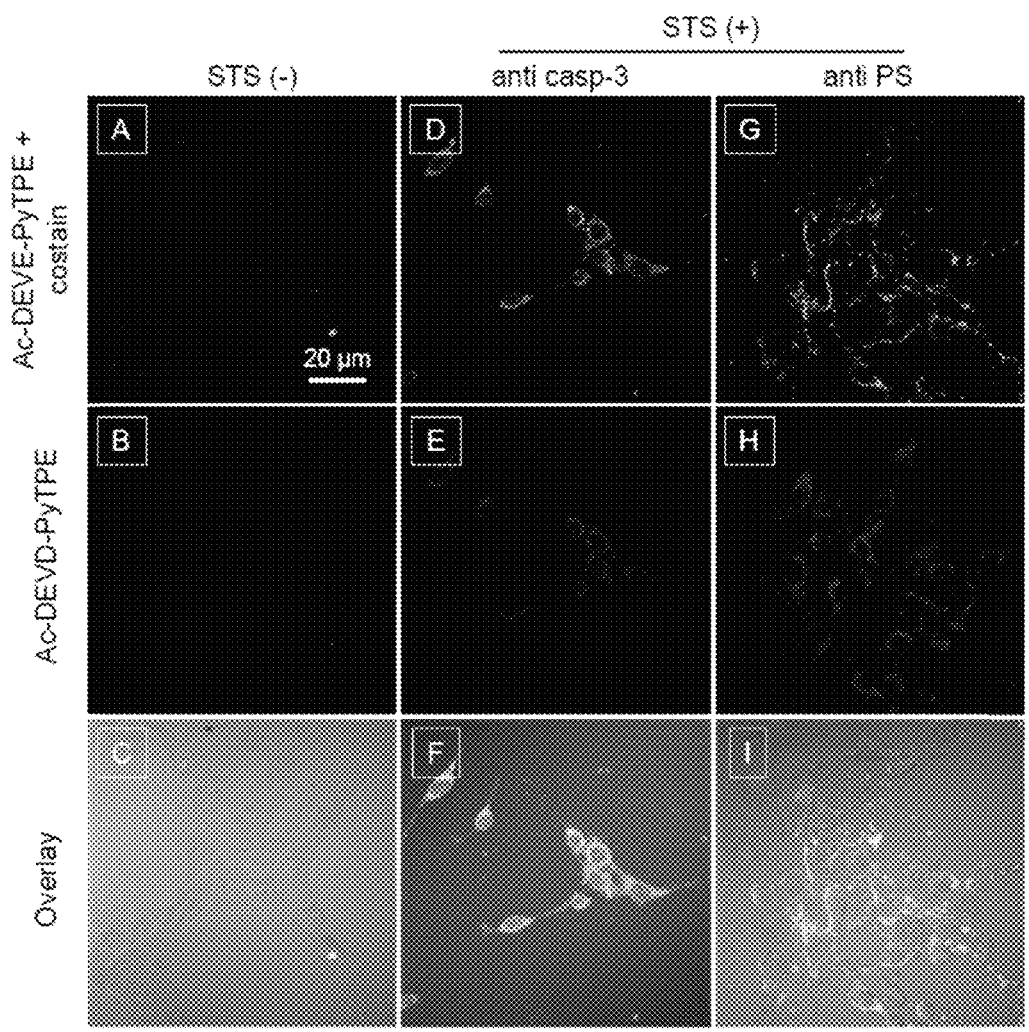
FIG. 46 shows confocal laser scanning microscopy (CLSM) images of live cell apoptosis. All images share the same scale bar (20 μm).
Figure 47:
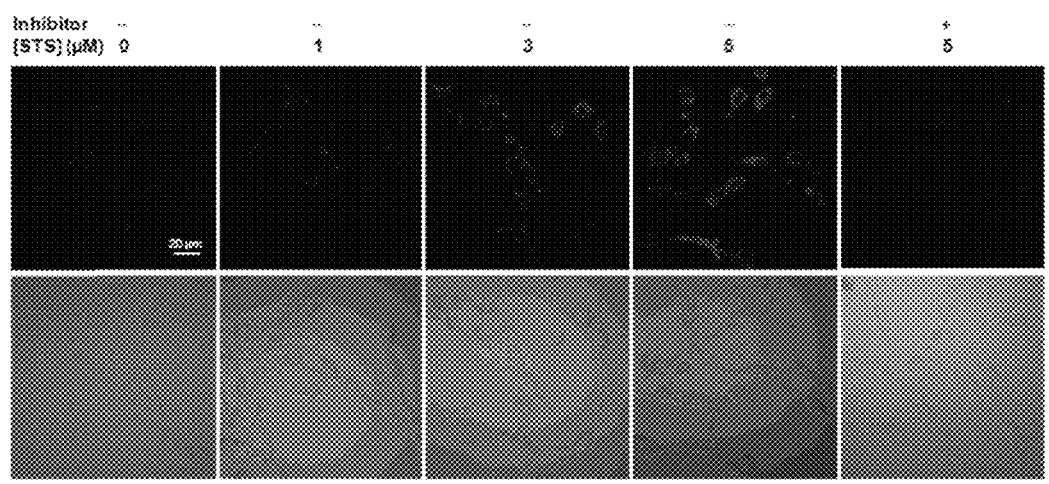
FIG. 47 shows CLSM images of MCF-7 live cell treated with different amounts of staurosporine and 3 μM Ac-DEVD-PyTPE as well as fluorescence imaging of apoptotic MCF-7 cells treated with Ac-DEVD-PyTPE (3 μM, 1% DMSO) and inhibitor (10 μM). All images were acquired in the same way.

As shown in FIG. 46b, normal and un-induced MCF-7 cells treated with Ac-DEVD-PyTPE show an extremely low fluorescence signal, indicative of little or no caspase-3 activity. In sharp contrast, strong fluorescence signals are collected from the MCF-7 cells treated with Ac-DEVD-PyTPE, wherein staurosporine (STS) was used to induce cell apoptosis (FIG. 46e). The fluorescence signals are greatly reduced when STS-induced cells are pre-treated with the inhibitor MPS, before incubation with Ac-DEVD-PyTPE (FIG. 46h).

Furthermore, excellent overlap is observed between the fluorescence images of the probe and immunofluorescence signals generated from anti-caspase-3 primary antibody and a Texas Red labeled secondary antibody (FIG. 46f). Additionally, apoptotic MCF-7 cells were treated with both Ac-DEVD-PyTPE and commercial Annexin V-Alexa Fluor. As expected, Annexin V-Alexa Fluor is localized on the cell surface, but Ac-DEVD-PyTPE shows strong fluorescence inside the cells (FIG. 46i). Collectively, these results provide direct evidence for intracellular delivery and caspase-specific activation of the imaging probe. Undoubtedly, Ac-DEVD-PyTPE is a suitable probe for detection of caspase-3 activity and apoptosis imaging in live cells.

Figure 48:
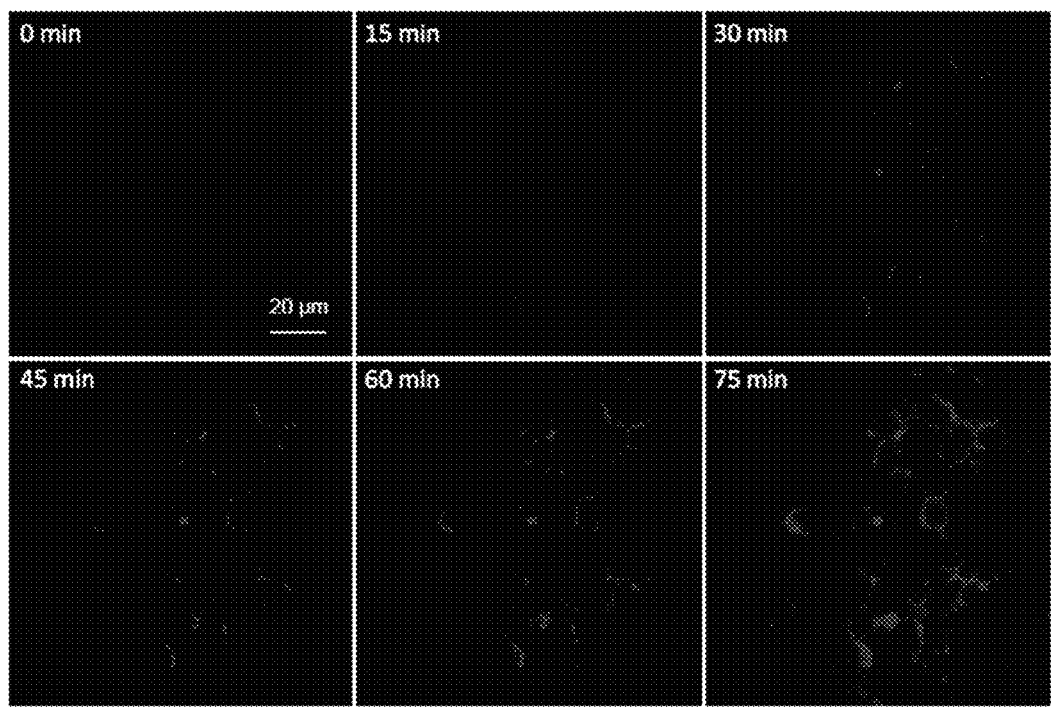
FIG. 48 shows real-time fluorescence images showing the cell apoptotic process of MCF-7 cells with Ac-DEVD-PyTPE (3 μM) at room temperature. STS (3 μM) was used to induce cell apoptosis. The images were acquired using CLSM under excitations at 405 nm using optical filters with band passes of 575-635 nm. All images have the same scale bar (10 μm).

Real-time imaging experiments were performed in FIG. 48. Ac-DEVD-PyTPE (3 μM) was incubated with MCF-7 cells at 37° C. After 2 h incubation, the cells were treated with STS (3 μM) and monitored with confocal microscopy to obtain real-time fluorescence images. The dark background in each image shown in FIG. 48 indicates that the probe is non-fluorescent in the cell culture media. As the incubation time elapses, the fluorescence intensity increases gradually with the cellular apoptotic progress. These results clearly demonstrate that Ac-DEVD-PyTPE not only can be used for detection of caspase-3 activity but also can be used for real-time monitoring of cell apoptosis.

Figure 49:
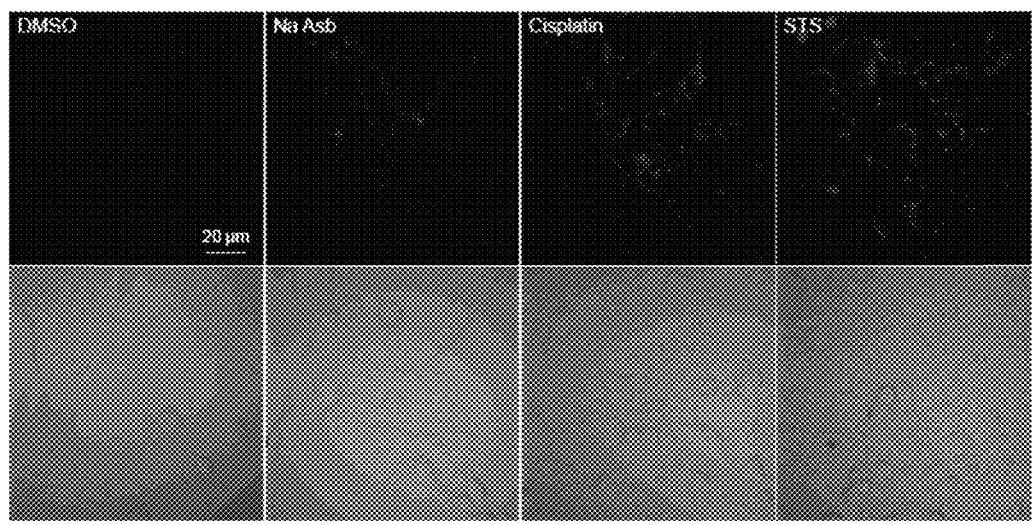
FIG. 49 shows CLSM images of Ac-DEVD-PyTPE pre-incubated MCF-7 cells upon treatment with 3 μM each of DMSO, sodium ascorbate (Na asb), cisplatin, and staurosporine (STS). [Ac-DEVD-PyTPE]=3 μM. All images were acquired in the same way.

FIG. 49 illustrates the capability of the Ac-DEVD-PyTPE probe for in situ screening of compounds that can induce cell apoptosis. Three known apoptosis inducers, sodium ascorbate, cisplatin and STS, were used to treat MCF-7 cells. After the cells were incubated with Ac-DEVD-PyTPE for 2 h, each compound (3 μM in DMSO) was added into the chamber for an additional 2 h incubation. The apoptosis-inducing capabilities of these agents were evaluated by monitoring the cell fluorescence increase with a confocal microscopy. As shown in FIG. 49, the strongest fluorescence enhancement is observed for the STS-treated cells compared to the sodium ascorbate- and cisplatin-treated cells. As is known in the art, STS has a relatively high inducing efficacy for apoptosis. Therefore, in one embodiment the Ac-DEVD-PyTPE probe can be used for screening apoptosis-inducing agents in living cells.

Figure 50:
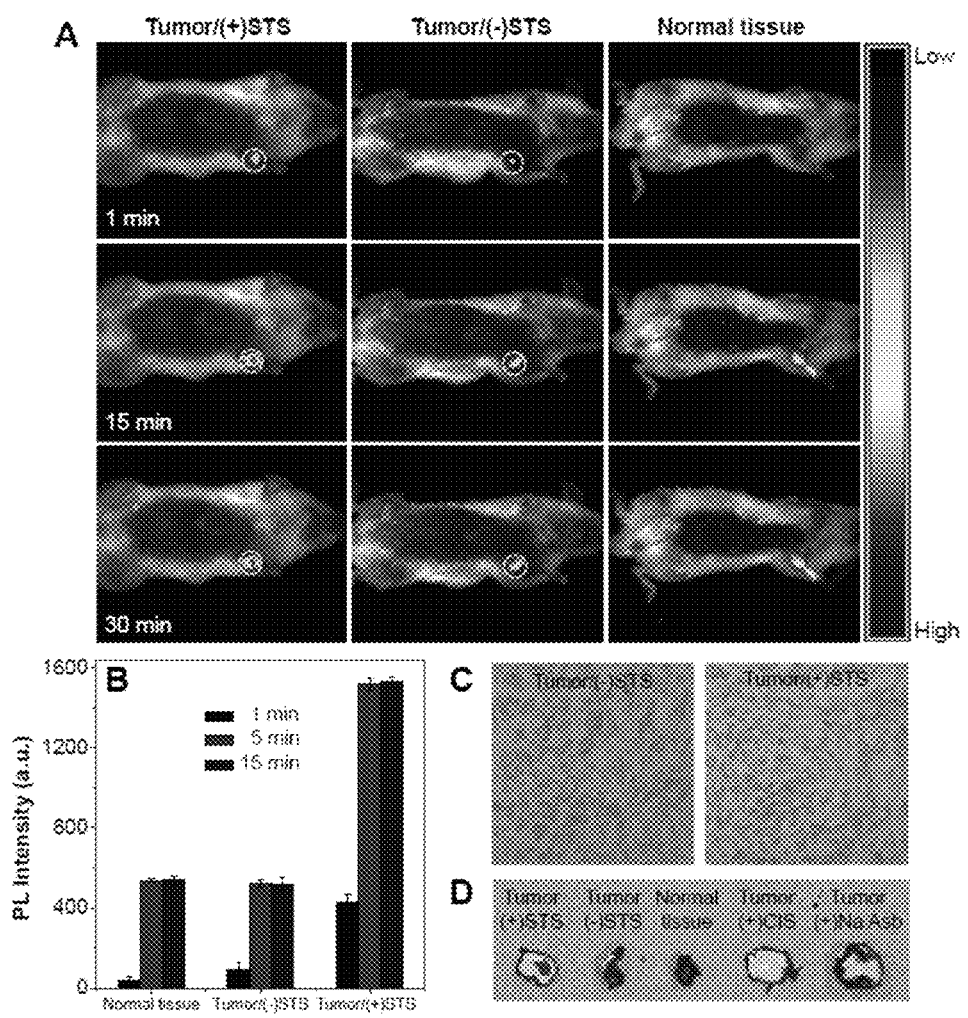
FIG. 50a shows in vivo fluorescence images of subcutaneous C6 tumor-bearing mice after intratumoral injection of Ac-DEVD-PyTPE with or without pretreatment of staurosporine (STS) (12 h before the probe injection). Only apoptotic tumors were clearly visualized.
FIG. 50b shows quantitative image analysis by fluorescence intensity in the probe-treated tissues as corresponding time.
FIG. 50c shows fluorescence images of excised Ac-DEVD-PyTPE-treated tissues.
FIG. 50d shows ex vivo screening of apoptosis inducers. STS, CIS and Na Asb.

FIG. 50a shows the utility of the Ac-DEVD-PyTPE probe for in vivo imaging of apoptosis. Subcutaneous C6 tumor-bearing mice with and without intravenous injection of STS were imaged for 30 min using an IVIS spectrum imaging system. As shown in FIG. 50a, induction of apoptosis using STS results in a gradual fluorescence increase from in vivo tumors with increasing time. In contrast, the fluorescence signals from the tumor-bearing animals without treatment of STS and normal tissues are very weak. This is consistent with the confocal laser scanning microscopy (CLSM) images shown in FIG. 46, indicating that Ac-DEVD-PyTPE can be used for in vivo visualization of apoptosis. Additionally, the fluorescence changes in tumoral and normal tissues as a function of time for each experiment are shown in FIG. 50b. A 3-fold fluorescence enhancement of the apoptotic tumoral tissues relative to normal tissues is observed as early as 5 min after injection of Ac-DEVD-PyTPE, but only a slight fluorescence increase is observed over 15 min. The non-apoptotic tumoral tissue showed similar fluorescence with normal tissues. The results suggest that the DEVE-PyTPE probe can be used to rapidly and sensitively respond to cell apoptosis in vivo.

FIG. 50c show IVIS spectrum analysis of apoptotic and non-apoptotic tumors that were excised immediately after in vivo imaging. A high fluorescence signal was specifically detected in the tumor/(+)STS tissues. However, almost no fluorescence was observed for tumor/(−)STS tissues, which closely matched the images obtained in live mice (FIG. 50a). Overall, these results demonstrated that the Ac-DEVD-PyTPE probe can be used for fluorescence light-up imaging of apoptosis in a living animal.

FIG. 50b demonstrates that the Ac-DEVD-PyTPE probe can be used to quantify the efficacy of apoptosis inducing agents in vivo. C6 tumor-bearing mice were treated with several compounds, namely DMSO, STS, cisplatin (CIS), and sodium ascorbate (Na asb), overnight, and Ac-DEVD-PyTPE was subsequently injected into the tumor directly. After 15 min incubation, the mice were imaged using an IVIS spectrum imaging system. As shown in FIG. 50b, STS shows the strongest fluorescence compared with the three other compounds. Collectively, these results demonstrate that the Ac-DEVD-PyTPE probe can also be used for quantitative analysis of the efficacy of apoptosis-related drugs in animals.

EXAMPLES

Having described the subject matter, the following examples are given to illustrate various embodiments and specific applications of the present subject matter. These specific examples are not intended to limit the scope of the subject matter described in this application.

Example 1

Synthesis of TPEBe-I

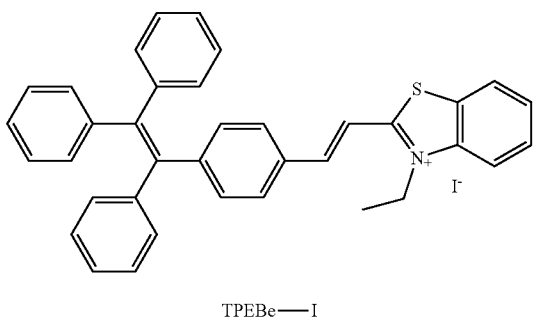

TPEBe—I

A solution of 5 (200 mg, 0.55 mmol) and an iodide salt of 8 (169 mg, 0.55 mmol) in dry EtOH (15 mL) was refluxed under nitrogen for 48 h. After cooling to an ambient temperature, the solvent was evaporated under reduced pressure. The residue was purified by a silica gel column chromatography using dichloromethane and acetone mixture (5:1 v/v) as eluent to give a yellow product in 80% yield.

$^1$H NMR (400 MHz, DMSO-$d_6$), δ (ppm): 8.42 (d, J=7.2 Hz, 1H), 8.28 (d, J=8.8 Hz, 1H), 8.12 (d, J=15.6 Hz, 1H), 7.93 (d, J=16.0 Hz 1H), 7.76-7.89 (m, 4H), 7.11-7.19 (m, 11H), 6.97-7.04 (m, 6H), 4.92 (q, 2H), 1.43 (t, J=7.2 Hz, 3H). $^{13}$C NMR (100 MHz, DMSO-$d_6$): δ (ppm): 171.4, 148.4, 147.5, 142.6, 142.4, 142.0, 140.8, 139.6, 131.3, 130.6, 130.5, 130.4, 129.5, 129.3, 128.2, 127.8, 127.7, 126.9, 126.7, 124.3, 116.5, 112.9, 44.4, 14.0. HRMS (MALDI-TOF): m/z 520.2103 [(M-I)$^+$, calcd 520.2099].

Example 2

Synthesis of TPEBe-ClO$_4$

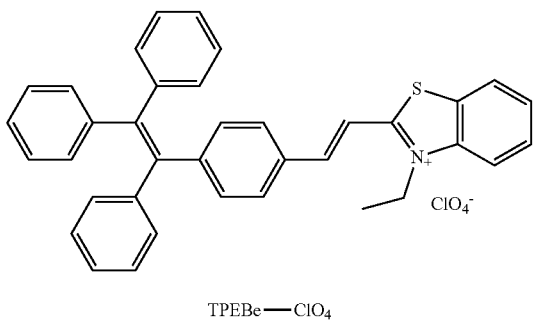

TPEBe—ClO$_4$

TPEBe-ClO$_4$ was prepared by a metathesis reaction. A saturated aqueous solution (10 mL) of a sodium salt of the anion was added to a solution of TPEBe-I in acetone solution (1.0 mmol, 10 mL). After stirring at room temperature for 30 min, the acetone was vapored under the reduced pressure. The product was isolated by filtration, washed with water and diethyl ether, and then dried in air.

$^1$H NMR (400 MHz, DMSO-$d_6$), δ (ppm): 8.42 (d, J=7.2 Hz, 1H), 8.28 (d, J=8.8 Hz, 1H), 8.12 (d, J=15.6 Hz, 1H), 7.92 (d, J=16.0 Hz, 1H), 7.76-7.89 (m, 4H), 7.11-7.18 (m, 11H), 6.96-7.04 (m, 6H), 4.92 (q, 2H), 1.43 (t, J=7.2 Hz, 3H). $^{13}$C NMR (100 MHz, DMSO-$d_6$): δ (ppm): 171.4, 148.4, 147.5, 142.6, 142.4, 142.0, 140.8, 139.6, 131.3, 130.6, 130.5, 130.4, 129.5, 129.3, 128.2, 127.8, 127.7, 126.9, 126.7, 124.3, 116.5, 112.9, 44.4, 14.0. HRMS (MALDI-TOF): m/z 520.2113 [(M-PF$_6$)$^+$, calcd 520.2099].

Table 1, below, summarizes the crystal data and intensity collection parameters for TPEBe-ClO$_4$.

TABLE 1

Summary of crystal data and intensity collection parameters for TPEBe—ClO$_4$.

| | |
|---|---|
| Empirical formula | C$_{39}$H$_{36}$ClNO$_5$S |
| Formula weight | 666.20 |
| Crystal dimensions, mm | 0.35 × 0.3 × 0.06 |
| Crystal system | Monoclinic |
| Space group | P2(1)/c |
| a, Å | 24.1796 (6) Å |
| b, Å | 8.8773 (2) |
| c, Å | 16.6170 (4) |
| α, deg | 90 |
| β, deg | 98.386 (2) |
| γ, deg | 90 |
| V, Å$^3$ | 3528.70 (15) |
| Z | 4 |
| D$_{calcd}$, gcm$^3$ | 1.254 |
| F$_{000}$ | 1400 |
| Temp. (K) | 173.1 (5) |
| Radiation (λ), Å | 1.5418 |
| μ (Cu Kα) mm$^{-1}$ | 1.863 |
| 2θ$_{max}$, deg (completeness) | 66.50 (97.8%) |
| No. of collected reflns. | 23215 |
| No. of unique reflns, (R$_{int}$) | 6156 (0.0512) |
| Data/restraints/parameters | 11388/132/855 |
| R$_1$, wR$_2$ [obs I > 2σ (I)] | 0.0760, 0.1892 |
| R$_1$, wR$_2$ (all data) | 0.0878, 0.1987 |
| Residual peak/hole e. Å$^{-3}$ | 0.558/−0.31 |
| Transmission ratio | 1.00/0.48545 |
| Goodness-of-fit on F$^2$ | 1.013 |

Example 3

Synthesis of TPEBe-PF$_6$

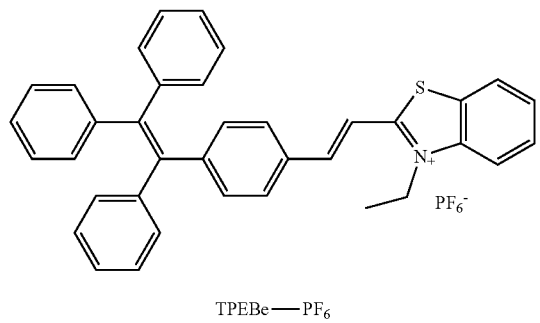

TPEBe—PF$_6$

TPEBe-PF$_6$ was prepared by metathesis reaction. A saturated aqueous solution (10 mL) of a potassium salt of the anion was added to a solution of TPEBe-I in acetone solution (1.0 mmol, 10 mL). After stirring at room temperature for 30 min, the acetone was vapored under the reduced pressure. The product was isolated by filtration, washed with water and diethyl ether, and then dried in air.

$^1$H NMR (400 MHz, DMSO-$d_6$), δ (ppm): 8.41 (d, J=8.0 Hz, 1H), 8.27 (d, J=8.4 Hz, 1H), 8.13 (d, J=15.6 Hz, 1H), 7.94 (d, J=16 Hz 1H), 7.75-7.88 (m, 4H), 7.02-7.15 (m, 11H), 6.96-7.00 (m, 6H), 4.91 (q, 2H), 1.42 (t, J=7.2 Hz, 3H). $^{13}$C NMR (100 MHz, DMSO-$d_6$): δ (ppm): 171.4, 148.4, 147.5, 142.6, 142.4, 142.0, 140.8, 139.6, 131.3, 130.6, 130.5, 130.4, 129.5, 129.3, 128.2, 127.8, 127.7, 126.9, 126.7, 124.3, 116.5, 112.9, 44.4, 14.0. HRMS (MALDI-TOF): m/z 520.2281 [(M-PF$_6$)$^+$, calcd 520.2099].

TPEBe-PF$_6$ crystals were obtained by slow evaporation of its DCM/ethanol, THF/hexane, and DCM/ethyl acetate (EtOAc) mixtures and analyzed by crystal X-ray diffraction, the data of which are provided in Table 2 below.

TABLE 2

Summary of crystal data and intensity collection parameters for TPEBe—PF$_6$, TPEBe—PF$_6$•2/3 THF, and TPEBe—PF$_6$•EtOAc.

| | TPEBe—PF$_6$ | TPEBe—PF$_6$•2/3 THF | TPEBe—PFs•EtOAc |
|---|---|---|---|
| Empirical formula | C$_{37}$H$_{30}$F$_6$NPS | C$_{43}$H$_{42}$F$_6$NO$_{1.50}$PS | C$_{41}$H$_{38}$F$_6$NO$_2$PS |
| Formula weight | 665.65 | 773.81 | 753.75 |
| Crystal dimensions, mm | 0.38 × 0.35 × 0.15 | 0.38 × 0.29 × 0.06 | 0.40 × 0.15 × 0.04 |
| Crystal system | Triclinic | Triclinic | Triclinic |
| Space group | P-1 | P-1 | P-1 |
| a, Å | 9.6816 (4) | 9.7467 (4) | 9.6552 (4) |
| b, Å | 17.8079 (10) | 17.3887 (8) | 17.4019 (11) |
| c, Å | 20.1801 (10) | 23.8490 (10) | 23.8103 (11) |
| α, deg | 73.460 (5) | 72.962 (4) | 72.469 (5) |
| β, deg | 76.508 (4) | 85.952 (3) | 84.653 (4) |
| γ, deg | 84.393 (4) | 83.053 (4) | 82.064 (4) |
| V, Å$^3$ | 3241.4 (3) | 3833.6 (3) | 3772.6 (3) |
| Z | 4 | 4 | 4 |
| D$_{calcd}$, gcm$^3$ | 1.364 | 1.341 | 1.327 |
| F$_{000}$ | 1376 | 1616 | 1568 |
| Temp, (K) | 173.1 (5) | 173.00 (14) | 172.9 (3) |
| Radiation (λ), Å | 1.5418 | 1.5418 | 1.5418 |
| μ (Cu Kα) mm$^{-1}$ | 1.895 | 1.707 | 1.731 |
| 2θ$_{max}$, deg (completeness) | 66.50 (98.5%) | 66.50 (97.5%) | 66.50 (97.7%) |
| No. of collected reflns. | 20032 | 22938 | 22017 |
| No. of unique reflns. (R$_{int}$) | 11388 (0.0505) | 13263 (0.0469) | 13132 (0.0462) |
| Data/restraints/parameters | 11388/132/855 | 13263/78/984 | 13132/165/1025 |
| R$_1$, wR$_2$ [obs I > 2σ (I)] | 0.0751, 0.2030 | 0.0680, 0.1762 | 0.0597, 0.1583 |
| R$_1$, wR$_2$ (all data) | 0.0895, 0.2193 | 0.0859, 0.1897 | 0.0824, 0.1760 |
| Residual peak/hole e. Å$^{-3}$ | 0.895/−0.652 | 0.549/−0.456 | 0.696/−0.387 |
| Transmission ratio | 1.00/0.92 | 1.00/0.74 | 1.00/0.84 |
| Goodness-of-fit on F$^2$ | 1.035 | 1.041 | 1.028 |
| CCDC number | 883789 | 883790 | 883791 |

In addition, Table 3, below, summarizes the photophysical properties, torsion angels, and energy gaps of crystals of TPEBe-PF$_6$.

TABLE 3

Photophysical properties, torsion angles and energy gaps of crystals of TPEBe—PF$_6$[a]

| Crystal | λ$_{em}$ (nm) | Φ$_F$ (%) | θ$_1$ (deg) | ΔE (eV) |
|---|---|---|---|---|
| TPEBe—PF$_6$ | 565 | 18.0 | 70.42 | 1.89 |
| TPEBe—PF$_6$•2/3 THF | 578 | 28.2 | 70.37 | 1.83 |
| TPEBe—PF$_6$•EtOAc | 591 | 43.6 | 67.94 | 1.79 |

[a]Abbreviation: λ$_{em}$ = emission maximum, Φ$_F$ = fluorescence quantum yield determined using a calibrated integrating sphere, ΔE = energy band gap determined using B3LYP/6-31G(d) basis set.

Example 4

Synthesis of TPEPy-PF$_6$

A solution of 5 (200 mg, 0.55 mmol) and iodide salt of 11 (130 mg, 0.55 mmol) in dry EtOH (15 mL) was refluxed under nitrogen for 48 h. After cooling to an ambient temperature, the solvent was evaporated under reduced pressure. The solid was dissolved in acetone (5 mL). Then, a saturated aqueous solution of KPF$_6$ (5 mL) was added. After stirring for 30 min, the solution was evaporated to dryness. The residue was purified by a silica gel column chromatography using dichloromethane and acetone mixture (5:1 v/v) as eluent to give a yellow product in 53% yield.
$^1$H NMR (400 MHz, CDCl$_3$), δ (TMS, ppm): 8.40 (d, J=6.4 Hz, 2H), 7.80 (d, J=5.6 Hz, 2H), 7.51 (d, J=16 Hz, 1H), 7.31 (d, J=8 Hz, 2H), 7.13 (m, 19H), 6.95 (d, J=16 Hz, 1H), 4.27 (s, 3H). $^{13}$C NMR (100 MHz, d$_6$-DMSO), δ (ppm): 152.36, 145.45, 145.01, 142.84, 142.68, 141.55, 140.06, 139.87, 133.22, 131.37, 130.65, 130.55, 127.91, 127.79, 127.58, 126.80, 126.73, 123.37, 123.11, 46.83. HRMS (MALDI-TOF): m/z 450.2123 [(M-PF$_6$)', calcd 450.2222].

Example 5

Synthesis of N$_3$-PyTPE

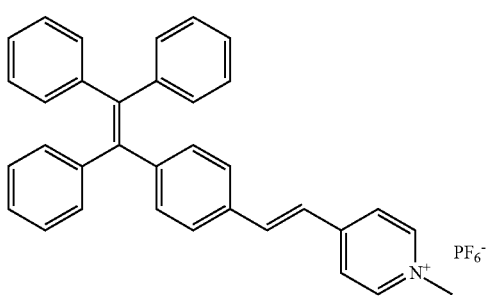

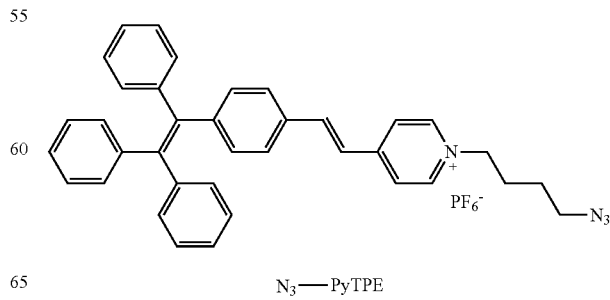

N$_3$—PyTPE

A solution of 5 (200 mg, 0.55 mmol) and an iodide salt of 14 (169 mg, 0.55 mmol) in dry EtOH (15 mL) was refluxed under nitrogen for 48 h. After cooling to an ambient temperature, the solvent was evaporated under reduced pressure. The solid was dissolved in acetone (5 mL). Then, a saturated aqueous solution of $KPF_6$ (5 mL) was added. After stirring for 30 min, the solution was evaporated to dryness. The residue was purified by a silica gel column chromatography using dichloromethane and acetone mixture (5:1 v/v) as eluent to give a yellow product $N_3$-PyTPE (119 mg, 32%).

$^1$H NMR (400 MHz, DMSO-$d_6$), δ (ppm): 8.92 (t, J=6.8 Hz, 2H), 8.18 (t, J=6.8 Hz, 2H), 7.90 (t, J=16.4 Hz, 1H), 7.51 (t, J=8.4 Hz, 2H), 7.42 (d, J=16.0 Hz, 1H), 7.11-7.18 (m, 9H), 7.06 (d, J=8.4 Hz, 2H), 6.96-7.02 (m, 6H), 4.50 (t, J=7.2 Hz, 2H), 3.39 (t, J=6.8 Hz, 2H), 1.92-1.99 (m, 2H), 1.50-1.57 (m, 2H). $^{13}$C NMR (100 MHz, DMSO-$d_6$), δ (ppm): 152.70, 145.39, 144.06, 142.79, 142.71, 142.55, 141.43, 140.23, 139.73, 133.09, 131.26, 131.26, 130.53, 130.51, 130.43, 127.78, 127.66, 127.50, 126.68, 126.60, 126.56, 123.63, 122.98, 59.00, 49.82, 27.68, 24.75. HRMS (MALDI-TOF): m/z 533.2691 [(M-$PF_6$)$^+$, calcd 533.2728].

Example 6

Synthesis of DEVD-PyTPE

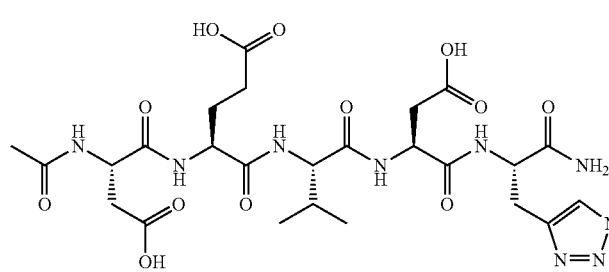
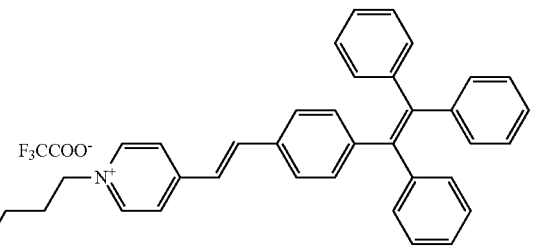

DEVD—PyTPE

Alkyne-functionalized DEVD (9.3 mg, 15 μmol) and $N_3$-PyTPE (12.3 mg, 18 μmol) were dissolved in 50 μL of DMSO. A mixture of DMSO/$H_2O$ solution (v/v=1/1; 1.0 mL) was subsequently added and the reaction was shaken for a few minutes to obtain a clear solution. The "click" reaction was initiated by sequential addition of catalytic amounts of sodium ascorbate (1.2 mg, 6.0 μmol) and $CuSO_4$ (4.8 mg, 3.0 μmol). The reaction was continued by shaking at room temperature for another 24 h. The final product was purified by prep-HPLC and further characterized by NMR and HRMS.

$^1$H NMR (600 MHz, DMSO-$d_6$), δ (TMS, ppm): 12.2 (s, 3H), 8.86 (d, J=6.0 Hz, 2H), 8.20-8.23 (m, 2H), 8.16 (d, J=6.0 Hz, 2H), 7.99-8.01 (m, 2H), 7.88 (d, J=18.0 Hz, 1H), 7.78 (s, 1H), 7.64 (d, J=12.0 Hz, 1H), 7.50 (d, J=6.0 Hz, 2H), 7.39 (d, J=18.0 Hz, 1H), 7.22 (s, 1H), 7.12-7.15 (m, 10H), 7.05 (d, J=6.0 Hz, 2H), 6.96-7.01 (m, 6H), 4.47-4.52 (m, 4H), 4.31-4.35 (m, 3H), 4.23-4.26 (q, J=6.0 Hz, 1H), 4.07 (t, J=6.0 Hz, 2H), 3.58 (t, J=6.0 Hz, 1H), 3.07 (dd, J=6.0 Hz, 1H), 2.89 (dd, J=6.0 Hz, 1H), 2.61-2.70 (m, 2H), 2.52 (dd, J=6.0 Hz, 1H), 2.48 (s, 3H), 2.46 (d, J=6.0 Hz, 1H), 2.17-2.22 (m, 2H), 1.86-1.94 (m, 3H), 1.71-1.74 (m, 2H), 0.77 (t, J=6.0 Hz, 6H). $^{13}$C NMR (100 MHz, DMSO-$d_6$), δ (TMS, ppm): 174.5, 172.7, 172.4, 172.2, 171.6, 170.0, 158.6, 158.4, 153.3, 146.0, 144.6, 143.5, 143.3, 143.2, 142.1, 140.8, 140.4, 133.7, 131.9, 131.2, 131.1, 131.9, 128.4, 128.3, 128.1, 127.3, 127.2, 124.3, 123.6, 123.3, 67.5, 59.5, 58.3, 52.9, 52.5, 50.2, 50.1, 48.9, 36.4, 36.1, 30.8, 30.5, 28.4, 28.1, 27.3, 26.8, 25.6, 22.9, 19.5, 18.4. HRMS (MALDI-TOF): m/z 1145.5104 ([M]$^+$, calcd 1145.5091). The HPLC condition is: 20-100% B for 10 min, then 100% B for 2 min, 20% B for 5 min (Solvent A: 100% $H_2O$ with 0.1% TFA; Solvent B: 100% $CH_3CN$ with 0.1% TFA).

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter, which are obvious to those skilled in chemistry, biochemistry, or related fields are intended to be within the scope of the following claims.

We claim:

1. A cationic fluorescent luminogen exhibiting aggregation-induced/enhanced emission (AIE/AEE) comprising one or more heterocycle units; wherein the luminogen comprises a chemical structure selected from the group consisting of:

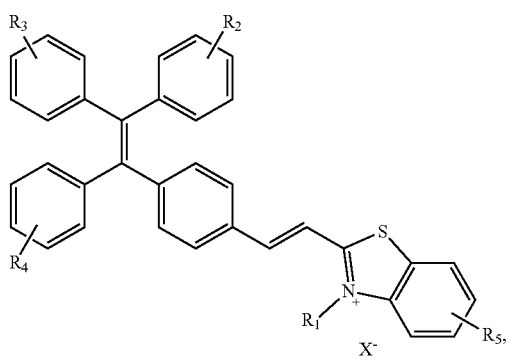

-continued

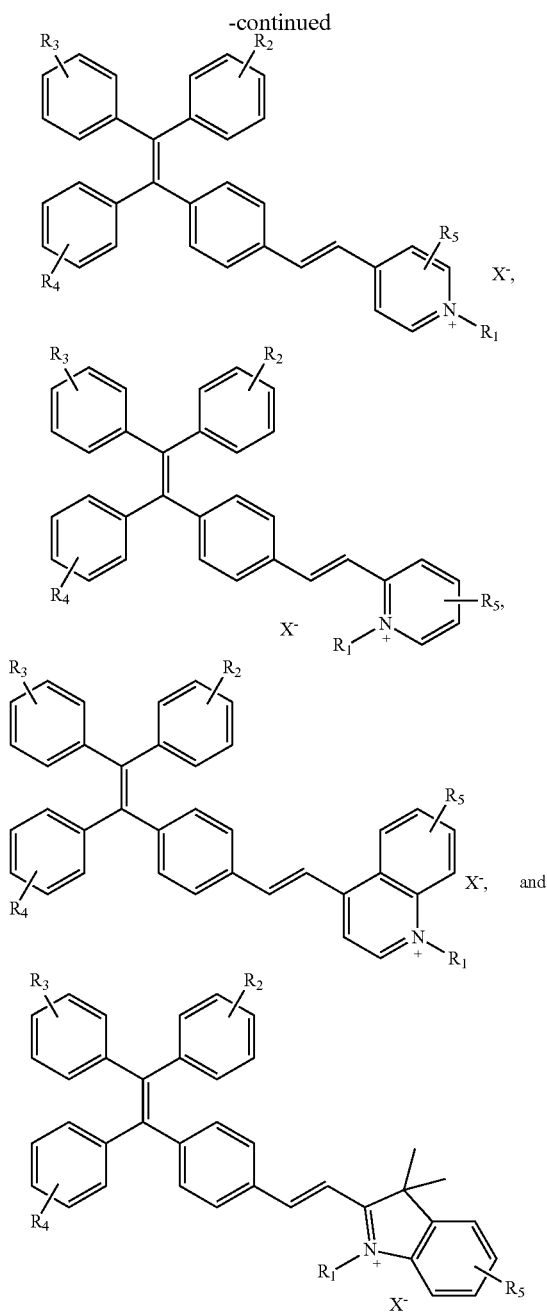

wherein each $R_1$, $R_2$, $R_3$, $R_4$, and $R_5$ is independently selected from the group consisting of H, alkyl, unsaturated alkyl, heteroalkyl, cycloalkyl, heterocycloalkyl, aryl, heteroaryl, $C_nH_{2n+1}$, $C_{10}H_7$, $C_{12}H_9$, $OC_6H_5$, $OC_{10}H_7$, $OC_{12}H_9$, $C_nH_{2n}COOH$, $C_nH_{2n}OH$, $C_nH_{2n}CHO$, $C_nH_{2n}COOC_4O_2N$, $C_nH_{2n}NCS$, $C_nH_{2n}N_3$, $C_nH_{2n}NH_2$, $C_nH_{2n}SH$, $C_nH_{2n}Cl$, $C_nH_{2n}Br$, and $C_nH_{2n}I$; n=0 to 20; and X is a monovalent counterion selected from the group consisting of I, Cl, Br, $PF_6$, $ClO_4$, $BF_4$, $BPh_4$, and $CH_3PhSO_3$.

2. The luminogen of claim 1, further exhibiting a long wave fluorescence emission.

3. The luminogen of claim 1, wherein the luminogen is used to label mitochondria in living cells.

4. The luminogen of claim 1, wherein the luminogen is used as a "turn-on" fluorescent sensor for $Hg^{2+}$.

5. The luminogen of claim 1, wherein the luminogen is used as a "turn-on" fluorescent sensor for ATP.

6. The luminogen of claim 1, wherein the luminogen is used as a fluorescent label for one or more biopolymers.

7. The luminogen of claim 6, wherein the one or more biopolymers are selected from the group consisting of a peptide, an antibody, and a nucleic acid.

8. The luminogen of claim 1, wherein the luminogen is used as a probe for caspase activity.

9. The luminogen of claim 8, wherein the luminogen is used as a specific probe for caspase-3 activity.

10. The luminogen of claim 8, wherein the luminogen is used as a specific probe for caspase-7 activity.

11. The luminogen of claim 8, wherein the luminogen is used as a probe for apoptosis imaging in live cells.

12. The luminogen of claim 1, wherein the luminogen is used for in vivo or in vitro screening of drugs that can induce cell apoptosis.

13. The luminogen of claim 1, wherein the luminogen is used as optical waveguide material.

14. The luminogen of claim 1, wherein the luminogen is used for stimuli-responsive luminescent materials.

15. A method of detecting caspase activity comprising contacting a solution containing cells with caspase enzymes with the luminogen of claim 1 and detecting fluorescence by measuring a change in fluorescence detected, wherein an increase in fluorescence signal is indicative of caspase activity.

16. The method of claim 15, wherein the caspase activity is selected from the group consisting of caspase-3 activity and caspase-7 activity; and wherein the caspase enzymes are selected from the group consisting of caspase-3 and caspase-7.

17. The method of claim 15, wherein the luminogen is specifically cleaved by the caspase enzymes.

18. A method of labeling mitochondria in cells comprising contacting one or more live cells with the luminogen of claim 1, wherein the luminogen of claim 1 is used as a fluorescent stain for living cell imaging after incubating the cells with the luminogen of claim 1.

19. A method of detecting $Hg^{2+}$ comprising contacting a solution comprising $Hg^{2+}$ with the luminogen of claim 1, and detecting $Hg^{2+}$ with the luminogen, wherein the luminogen of claim 1 is a selective and sensitive fluorescent chemosensor for detection of $Hg^{2+}$ in aqueous solution, where the luminogen of claim 1 exhibits enhanced emission due to the presence of $Hg^{2+}$.

20. A method of detecting ATP comprising contacting a solution comprising ATP with the luminogen of claim 1, and detecting ATP with the luminogen, wherein the luminogen of claim 1 is a selective and sensitive fluorescent sensor for detection of ATP in aqueous solution, where the luminogen of claim 1 exhibits enhanced emission due to the presence of ATP.

21. A method for in vitro monitoring of cell apoptosis comprising contacting a sample comprising caspase enzymes with the luminogen of claim 1 and detecting fluorescence by measuring a change in fluorescence detected, wherein an increase in fluorescence signal is indicative of caspase activity.

22. A method for in vivo monitoring of cell apoptosis comprising injecting a subject with the luminogen of claim 1 and detecting fluorescence by measuring a change in fluorescence, wherein an increase of fluorescence signal is indicative of cell apoptosis.

* * * * *